United States Patent
Cravatt et al.

(10) Patent No.: US 9,108,930 B2
(45) Date of Patent: Aug. 18, 2015

(54) N1- AND N2-CARBAMOYL-1,2,3-TRIAZOLE SERINE HYDROLASE INHIBITORS AND METHODS

(75) Inventors: Benjamin Cravatt, La Jolla, CA (US); Alexander Adibekian, Hanover (DE); Katsunori Tsuboi, Osaka (JP); Ku-Lung Hsu, El Cajon, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/009,452

(22) PCT Filed: Apr. 5, 2012

(86) PCT No.: PCT/US2012/032349
§ 371 (c)(1), (2), (4) Date: Oct. 2, 2013

(87) PCT Pub. No.: WO2012/138877
PCT Pub. Date: Oct. 11, 2012

(65) Prior Publication Data
US 2014/0018318 A1    Jan. 16, 2014

Related U.S. Application Data

(60) Provisional application No. 61/586,471, filed on Jan. 13, 2012, provisional application No. 61/472,593, filed on Apr. 6, 2011.

(51) Int. Cl.
| | |
|---|---|
| C07D 249/06 | (2006.01) |
| C07D 401/08 | (2006.01) |
| C07D 249/04 | (2006.01) |
| C07D 401/06 | (2006.01) |
| C07D 403/06 | (2006.01) |
| C07D 471/04 | (2006.01) |
| C07D 495/04 | (2006.01) |
| C07F 5/02 | (2006.01) |

(52) U.S. Cl.
CPC ............ *C07D 249/04* (2013.01); *C07D 249/06* (2013.01); *C07D 401/06* (2013.01); *C07D 403/06* (2013.01); *C07D 471/04* (2013.01); *C07D 495/04* (2013.01); *C07F 5/022* (2013.01)

(58) Field of Classification Search
CPC ........................... C07D 249/06; C07D 401/08
See application file for complete search history.

(56) References Cited

FOREIGN PATENT DOCUMENTS

| | | | |
|---|---|---|---|
| JP | 06049041 | * | 2/1994 |
| WO | WO2010074588 | * | 7/2010 |

OTHER PUBLICATIONS

Adibekain et al, Click-generated triazole ureas as ultrapotent in vivo-active serine hydrolase inhibitors, Nat. Chem. Biol., vol. 7, 2011, p. 469-478.*
STN Reg No. 1361533-95-3, entered into STIC Mar. 22, 2012.*

* cited by examiner

*Primary Examiner* — Rebecca Anderson
*Assistant Examiner* — Karen Cheng
(74) *Attorney, Agent, or Firm* — Olson & Cepuritis, Ltd.

(57) ABSTRACT

The present invention provides inhibitors of a wide variety of serine hydrolase enzymes. The inhibitors of the present invention are N1- and N2-carbamoyl-1,2,3-triazole compounds such as those of Formula (I):

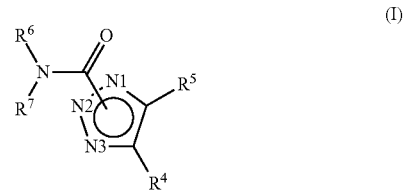

in which N1, N2, and N3 are the nitrogen atoms at positions 1, 2, and 3, respectively, of the triazole ring, and $R^4$, $R^5$, $R^6$ and $R^7$ in Formula (I) are as described herein. Methods of inhibiting serine hydrolase enzymes and methods of preparing carbamoyl-1,2,3-triazole compounds also are described.

11 Claims, 27 Drawing Sheets

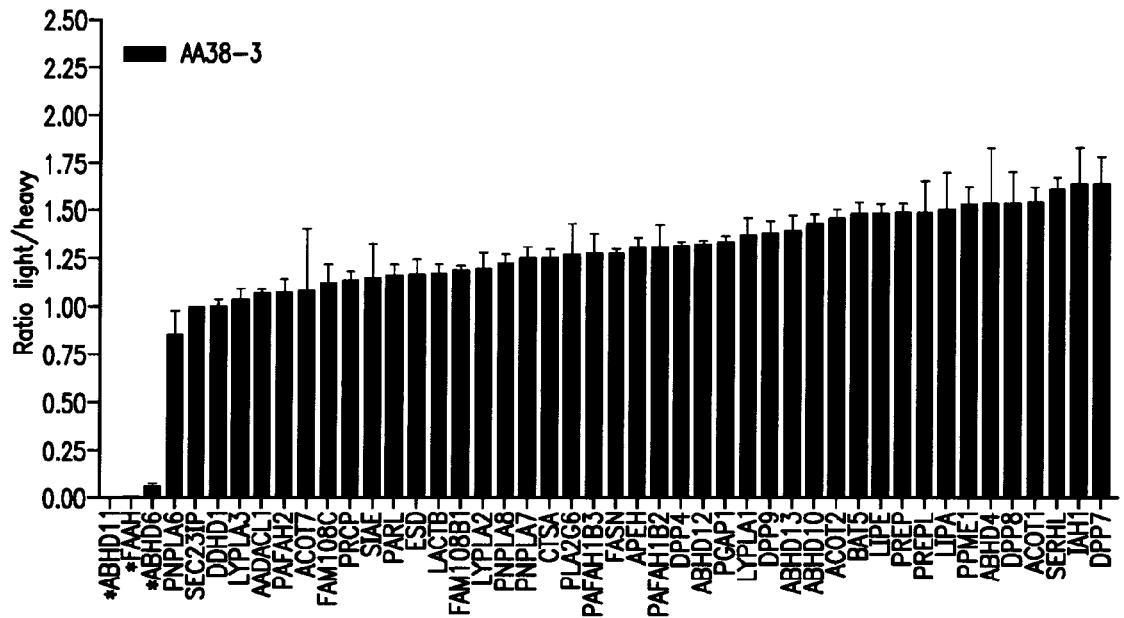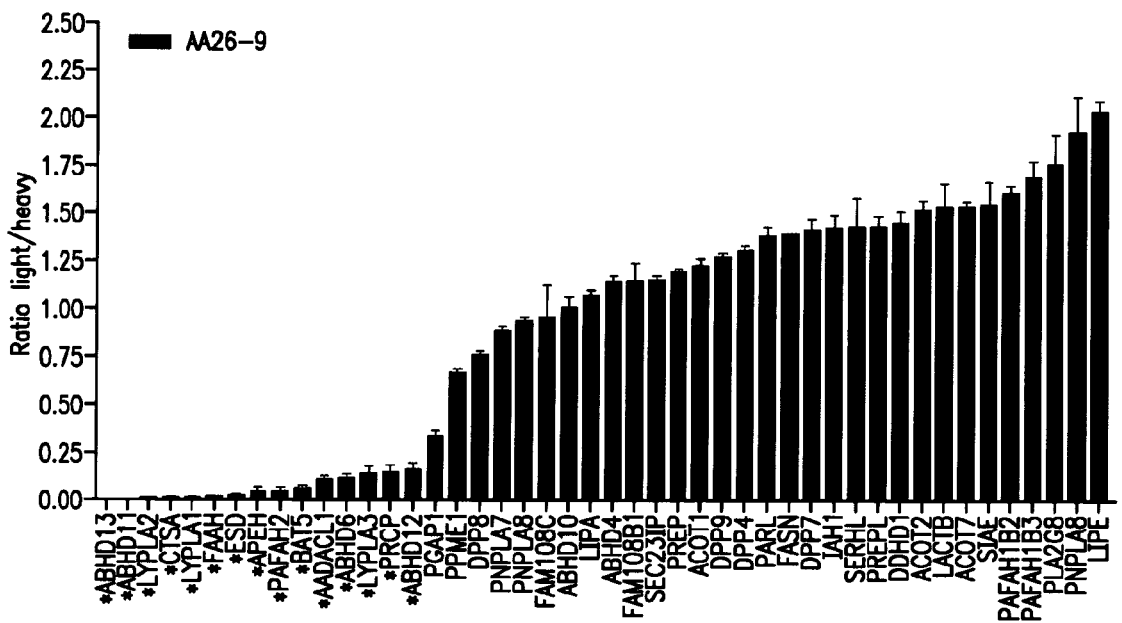
FIG. 2 (cont.)

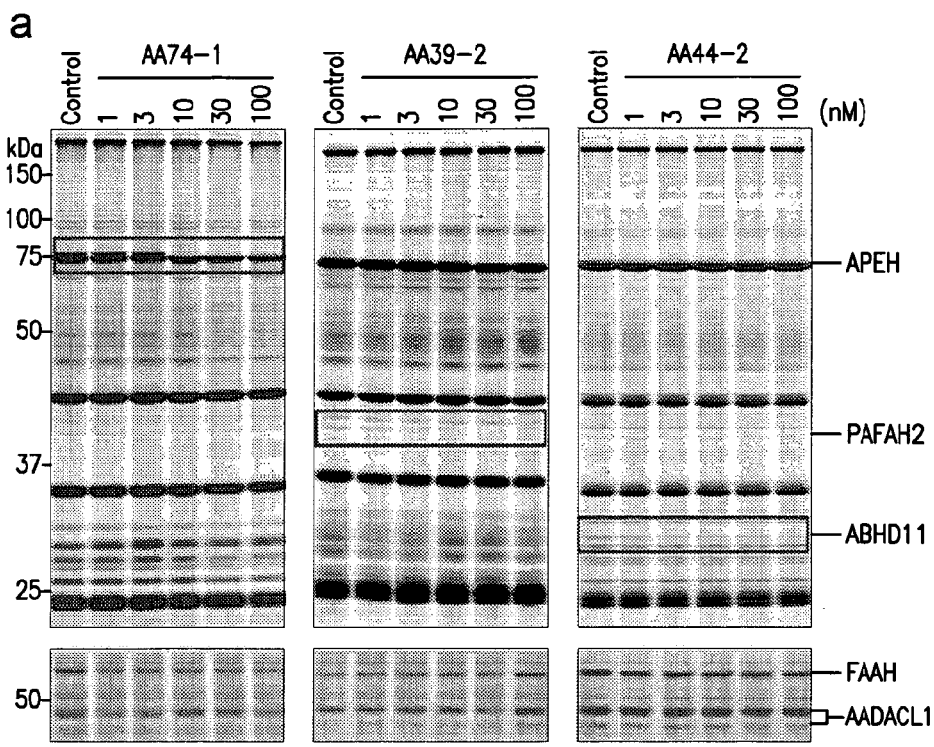
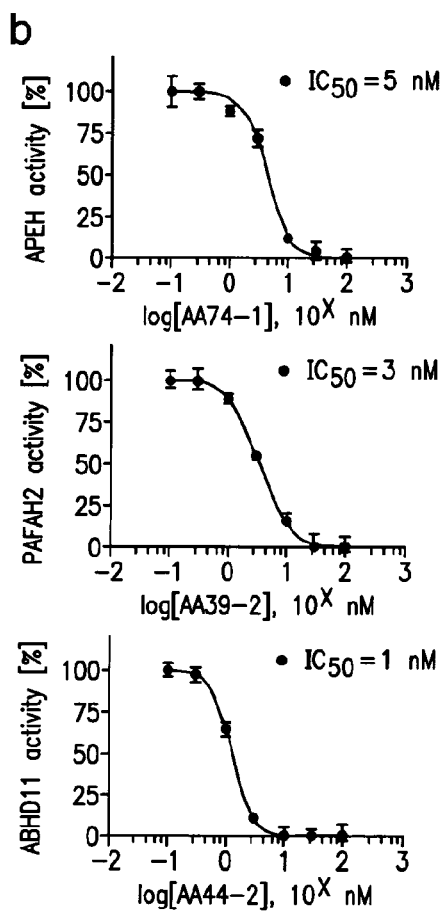
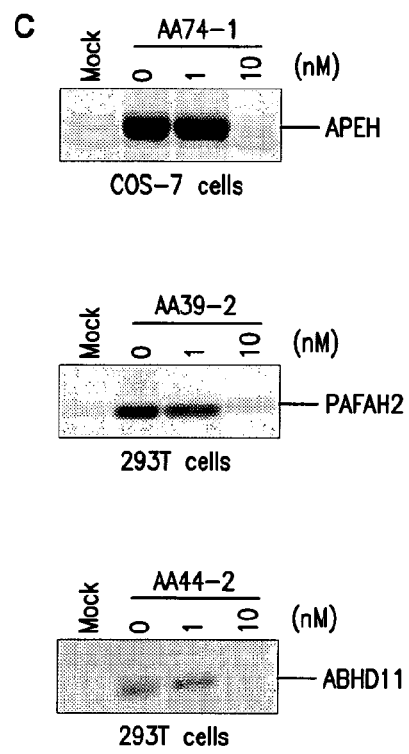
FIG. 4

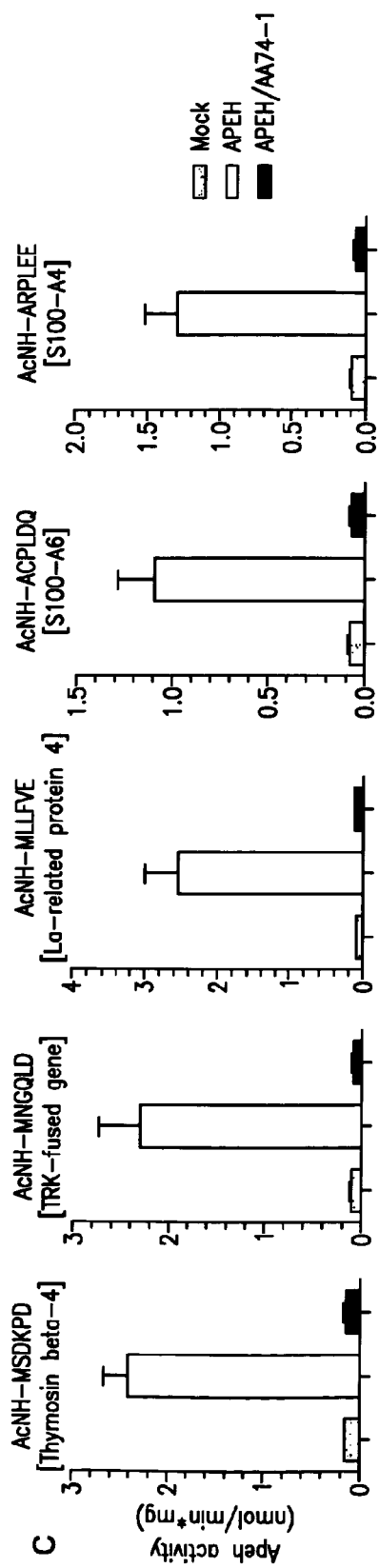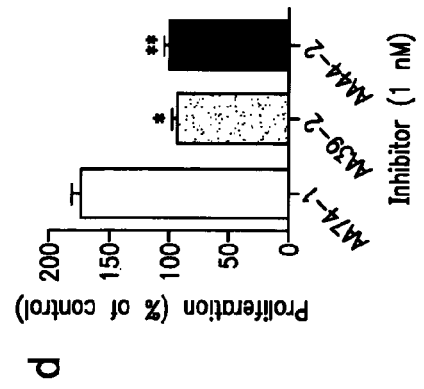
FIG. 6 (cont.)

| Name | Protein Description | Ratio AA74-1 (enriched) | Ratio AA74-1 (unenriched) | Ratio AA39-2 (enriched) |
|---|---|---|---|---|
| NDRG1 | N-myc downstream regulated gene 1 | 9.05 ± 1.5 | 0.98 ± 0.01 | 1.24 ± 0.26 |
| EG665937 | Similar to Ferritin light chain 1 | 7.07 ± 2.15 | 0.94 ± 0.08 | 1.05 ± 0.07 |
| CCDC97* | Coiled-coil domain containing protein 97 | 4.78 ± 0.22 | n.d. | 1.26 ± 0.16 |
| LARP4* | La ribonucleoprotein domain family, member 4 | 4.42 ± 0.23 | n.d. | 0.94 ± 0.05 |
| ARHGEF2 | Rho/Rac guanine nucleotide exchange factor 2 | 4.41 ± 0.55 | 1.08 ± 0.07 | 1.18 ± 0.13 |
| 5830457O10Rik | Chromosome transmission fidelity factor 8 homolog | 4.36 ± 1.17 | 1.26 ± 0.19 | 0.98 ± 0.02 |
| FBXO7 | F-box protein 7 | 4.27 ± 0.11 | 1.1 ± 0.04 | 0.88 ± 0.21 |
| NIBAN | Family with sequence similarity 129, member A | 4.22 ± 0.28 | 1.1 ± 0.04 | 1.30 ± 0.36 |
| S100A4* | S100 calcium binding protein A4 | 4.07 ± 0.3 | 1.01 ± 0.12 | 1.05 ± 0.08 |
| S100A6* | S100 calcium binding protein A6 | 3.93 ± 0.33 | 1.03 ± 0.15 | 1.07 ± 0.11 |
| PTPN18 | Protein tyrosine phosphatase, non-receptor type 18 | 3.58 ± 0.45 | 0.97 ± 0.09 | n.d. |
| NDUFV2 | NADH dehydrogenase (ubiquinone) flavoprotein 2 | 3.09 ± 0.52 | n.d. | 1.12 ± 0.19 |
| SERF2 | Small EDRK-rich factor 2 | 2.86 ± 0.15 | 1.05 ± 0.11 | 1.08 ± 0.08 |
| SKP1A | S-Phase kinase-associated protein 1 | 2.65 ± 0.24 | 1.04 ± 0.01 | 1.18 ± 0.26 |
| TMSB4X* | Thymosin beta 4, X-linked | 2.62 ± 0.12 | 1.19 ± 0.08 | 0.89 ± 0.17 |
| 1200013B08Rik | SAM and SH3 domain containing protein 3 | 2.61 ± 0.21 | 0.99 ± 0.16 | 1.15 ± 0.09 |
| PAIP2B | Poly(A) binding protein interacting protein 2B | 2.61 ± 0.63 | 0.92 ± 0.07 | 0.97 ± 0.01 |
| FDX1 | Adrenodoxin, mitochondrial | 2.6 ± 0.15 | 1.01 ± 0.11 | n.d. |
| PAIP2* | Poly(A) binding protein interacting protein 2 | 2.57 ± 0.29 | 0.9 ± 0.2 | 1.06 ± 0.14 |
| LARP1* | La ribonucleoprotein domain family, member 1 | 2.57 ± 0.44 | 1.08 ± 0.15 | 1.21 ± 0.26 |
| OXSR1 | Oxidative-stress responsive 1 | 2.52 ± 0.21 | 1.07 ± 0.04 | 1.09 ± 0.11 |
| TPI1 | triosephosphate isomerase 1 | 2.42 ± 0.35 | 1.12 ± 0.1 | 1.00 ± 0.07 |
| TFG* | TRK-fused gene | 2.36 ± 0.5 | 0.93 ± 0.15 | 1.13 ± 0.09 |
| UQCRH | Ubiquinol-cytochrome c reductase hinge protein | 2.27 ± 0.06 | 0.9 ± 0.26 | 1.22 ± 0.17 |
| EFHD2* | EF-hand domain family, member D2 | 2.18 ± 0.12 | 0.99 ± 0.14 | 0.97 ± 0.18 |

FIG. 7

| Name | Subclass | Carbamate Leads |
|---|---|---|
| 1. ABHD13 | unknown | no |
| 2. ABHD11 | unknown | yes |
| 3. LYPLA2 | thioesterase | no |
| 4. CTSA | peptidase | no |
| 5. LYPLA1 | thioesterase | no |
| 6. FAAH | amidase | yes |
| 7. ESD | lipase | no |
| 8. APEH | peptidase | no |
| 9. PAFAH2 | lipase | no |
| 10. BAT5 | unknown | no |
| 11. AADACL1 | lipase | yes |
| 12. ABHD6 | lipase | yes |
| 13. LYPLA3 | lipase | yes |
| 14. PRCP | peptidase | yes |
| 15. ABHD12 | lipase | no |

FIG. 8

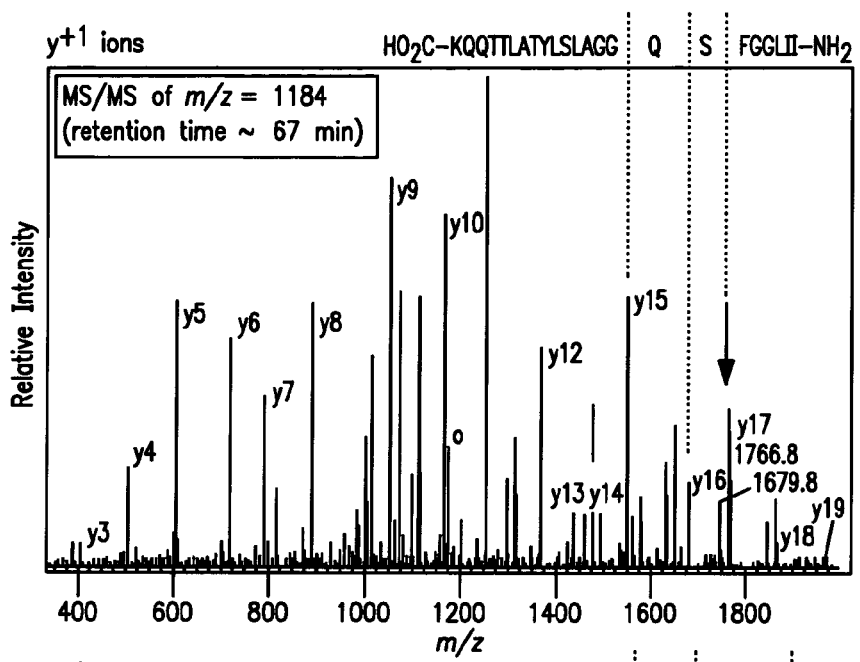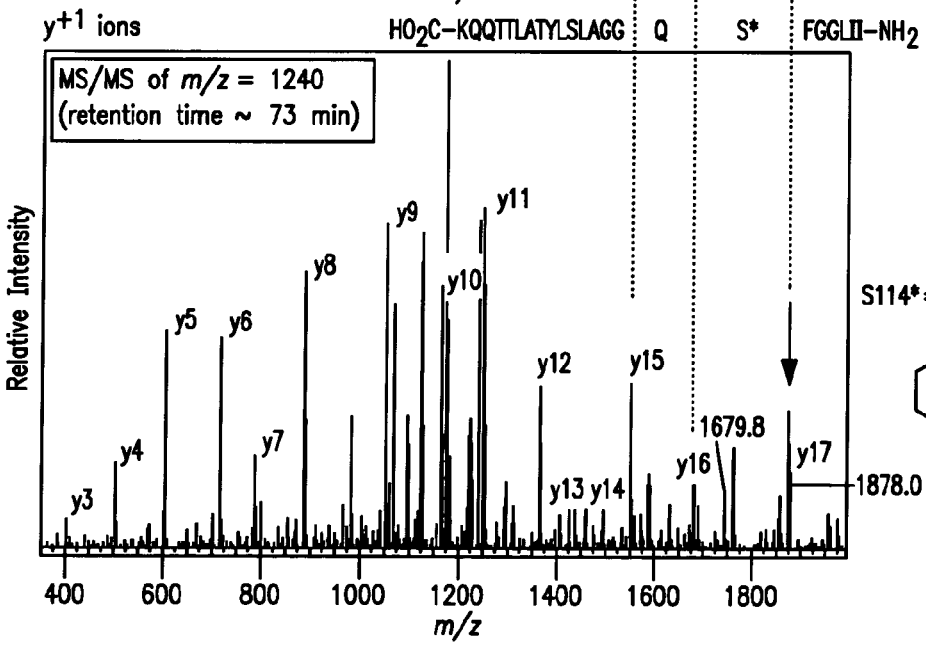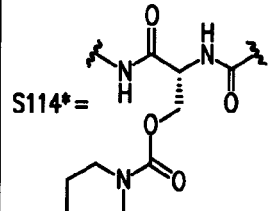
FIG. 11 (cont.)

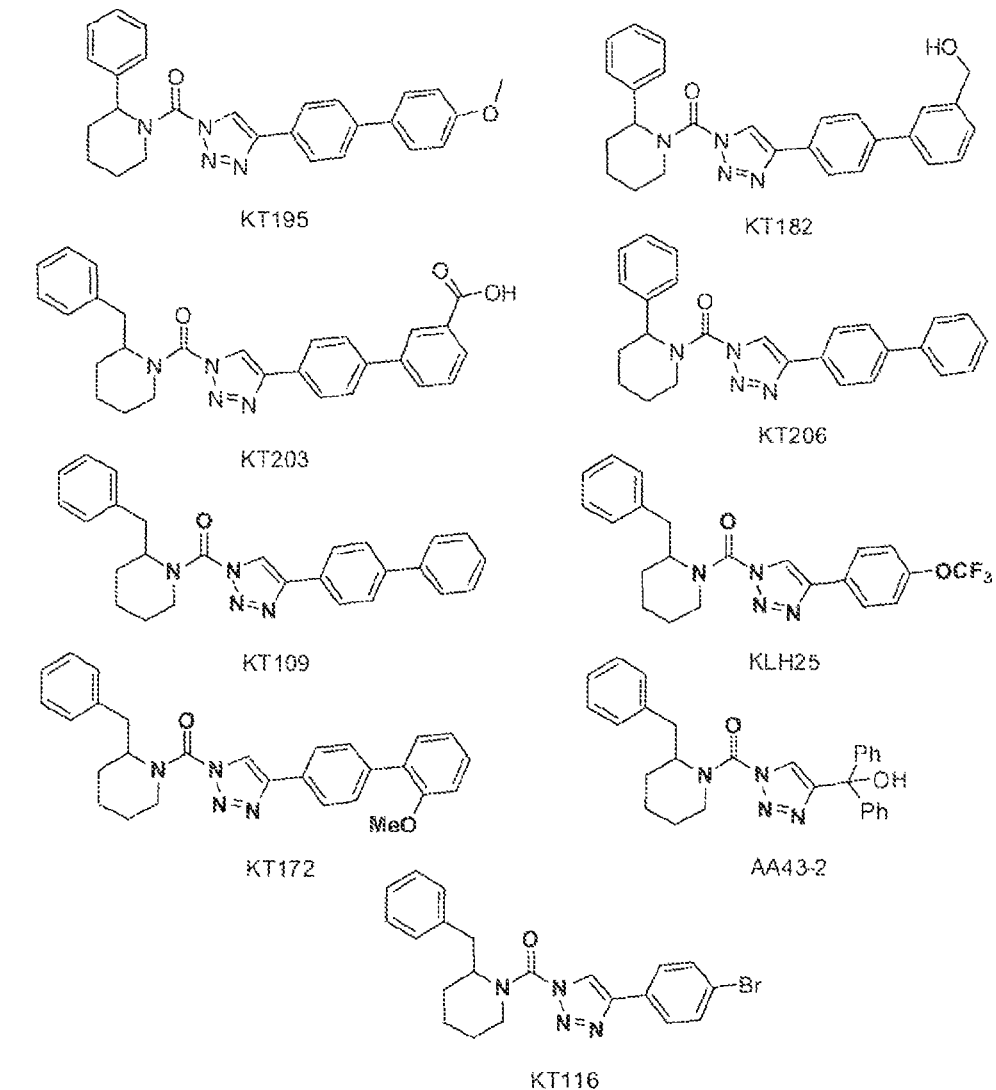
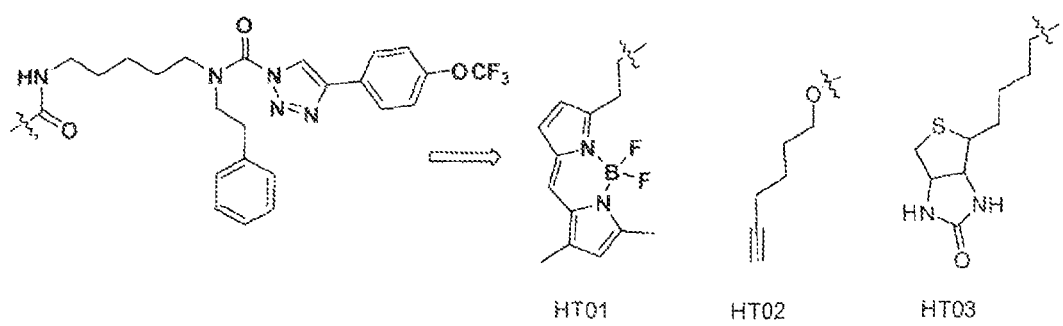
FIG. 21

N1- AND N2-CARBAMOYL-1,2,3-TRIAZOLE SERINE HYDROLASE INHIBITORS AND METHODS

CROSS-REFERENCE TO RELATED APPLICATIONS

This application claims the benefit of U.S. Provisional Application Ser. No. 61/586,471, filed on Jan. 13, 2012, and of U.S. Provisional Application Ser. No. 61/472,593, filed on Apr. 6, 2011, each of which is incorporated herein by reference in its entirety.

STATEMENT OF GOVERNMENT SUPPORT

This invention was made with government support under Contract Nos. CA132630, MH084512, CA151460 and DA025385 awarded by the National Institutes of Health. The Government has certain rights in this invention.

FIELD OF THE INVENTION

The present invention relates to inhibitors of serine hydrolase enzymes. In particular, the present invention relates to N1- and N2-carbamoyl-1,2,3-triazole compounds that are useful for inhibiting serine hydrolase enzymes.

BACKGROUND

Serine hydrolases (SHs) are one of the largest and most diverse enzyme families in the eukaryotic and prokaryotic proteomes, with a membership that includes lipases, esterases, thioesterases, peptidases/proteases, and amidases. The important biological roles played by SHs have led to the development of clinically approved drugs that target members of this enzyme family to treat diseases such as obesity, diabetes, microbial infections, and Alzheimer's disease. Despite these advances, most of the 200+ mammalian SHs remain poorly understood in terms of their biochemical and cellular activities. Pursuit of this knowledge would benefit from the development of selective inhibitors to probe the function of individual SHs in living systems. This constitutes an exciting, but challenging task that has been successfully accomplished for only a handful of SHs to date.

All SHs possess a serine nucleophile required for catalytic activity, opening up the opportunity to develop mechanism-based inhibitors that inactivate these enzymes by covalent modification. Among the classes of inhibitors that have been shown to react with the serine nucleophile of SHs, fluorophosphonates (FPs) and carbamates are exceptional in that they show negligible cross-reactivity with other nucleophilic enzymes such as cysteine hydrolases. FPs are highly reactive and provide broad, nearly complete coverage of the SH superfamily. This feature has promoted the use of reporter-tagged FPs for activity-based protein profiling (ABPP) investigations of SHs, but limits the utility of FPs as pharmacological probes for specific members of this enzyme class. Certain carbamate (R—O—C(O)—NR$_2$) compounds, on the other hand, have been developed that show excellent selectivity for individual SHs. These inhibitors have proven to be valuable research tools and, in certain cases, advanced to the stage of approved drugs (e.g., rivastigmine, which targets acetylcholine esterase (ACHE) to treat Alzheimer's disease). Despite considerable screening efforts, however, efficacious and selective carbamate inhibitors have been identified for only a fraction of mammalian SHs, pointing to the need for alternative chemical classes of SH inhibitors. The present invention addresses these needs.

For example, biosynthesis of the endocannabinoid, 2-arachidonoylglcerol (2-AG) is enzymatically regulated by two distinct diacylglycerol lipase (DAGL) enzymes, DAGLA and DAGLB. In contrast with the enzymatic mechanisms regulating 2-AG degradation, relatively little is known about the DAGL enzymes with respect to their in vivo physiological functions. Biochemical studies performed in vitro have provided evidence that these transmembrane serine hydrolases, which share very little sequence homology with each other, can catalyze the sn-1 selective cleavage of arachidonate-containing diglycerides to form 2-AG. Recent genetic studies with DAGLA and DAGLB knockout mice have provided in vivo evidence that the chronic absence of these enzymes result in decreased 2-AG levels in central and peripheral tissues, respectively. To date, no selective inhibitors have been available for the DAGL enzymes and the most widely used compound, tetrahydrolipstatin (THL) has been shown to have potent activity against numerous other serine hydrolases in complex proteomes. In addition, this broad-spectrum lipase inhibitor shows poor bioavailability in vivo, a feature that allows its use as an anti-obesity drug by restricting activity to the gastrointestinal tract. The dearth of suitable DAGL inhibitors available for in vivo studies has prompted a search for novel chemotypes capable of inactivating these lipases in a selective manner. However, several challenges are associated with developing DAGL inhibitors, namely the lack of available assays required for medium-throughput to high-throughput screening. A significant challenge in the development of in vivo active DAGL inhibitors is the inability to measure the endogenous activity of these enzymes. In fact, no studies to date have shown that the endogenous enzymes are catalytically active in living cells or tissues, complicating interpretation of metabolic changes seen in genetic models.

SUMMARY

The present invention provides, for example, a serine hydrolase inhibitor comprising an N1- or N2-carbamoyl-1,2,3-triazole compound (also referred to herein as a triazole urea) of Formula (I):

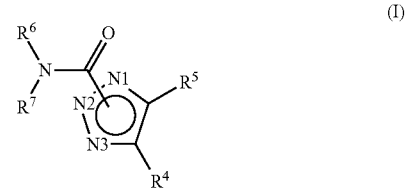

wherein each of $R^4$ and $R^5$, $R^6$ and $R^7$ are described herein. The carbamoyl substituent, —C(=O)NR$^6$, R$^7$, can be attached to the N1 position or the N2 position of the 1,2,3-triazole ring. In some preferred embodiments, the carbamoyl group is attached to the N2 position of the triazole ring. In other preferred embodiments, e.g., for the inhibition of diacylglycerol lipase beta (DAGLB), the carbamoyl substituent is attached to the N1 position of the triazole ring.

The N1- and N2-carbamoyl-1,2,3-triazole serine hydrolase inhibitors described herein, e.g., the compounds of Formulas (I), (II), (III), (IV), (IX), and related formulas described herein, can be included in a pharmaceutical composition, along with a pharmaceutically acceptable carrier, vehicle, or diluent, for treating a disease associated with serine hydrolase activity (e.g., obesity, diabetes, a microbial infection or Alzheimer's disease).

Another aspect of the present invention is a method of inhibiting a serine hydrolase enzyme. The method comprises, for example, contacting a serine hydrolase enzyme with a N1- or N2-carbamoyl-1,2,3-triazole compound, e.g., in an enzymatically compatible medium such as a physiological buffer, a biological fluid, and the like.

For example, provided herein are 2-substituted-piperidyl-1,2,3-triazole urea (2-SPTU) compounds that are suitable as inhibitors of DAGLB, such as compounds of Formula (IX):

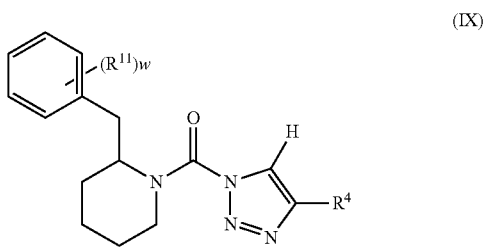

(IX)

wherein w, $R^{11}$ and $R^4$ are defined herein.

Another aspect of the present invention is the use of a N1- and N2-carbamoyl-1,2,3-triazole compound, such as those of Formulas (I), (II), (III), (IV), (IX), and related formulas described herein, for treating a disease as described herein, or for the preparation of a medicament for treating a disease or condition that would benefit from serine hydrolase inhibition, such as obesity, diabetes, microbial infections, and Alzheimer's disease.

BRIEF DESCRIPTION OF THE DRAWINGS

FIG. 7 provides a table of changes in the proteomic profile of endogenous substrates of APEH induced by inhibitors of the invention.

FIG. 8 provides a table of SH enzymes targeted by triazole urea AA26-9.

FIG. 21 provides structures of some representative substituted 1,2,3-triazole ureas having ABHD6 inhibitory activity (compounds KT195, KT182, KT203, and KT206) and/or DAGLB inhibitory activity (compounds AA43-2, KT116, KT109, KT172, HT01, and KLH25).

DETAILED DESCRIPTION

Figure 1:
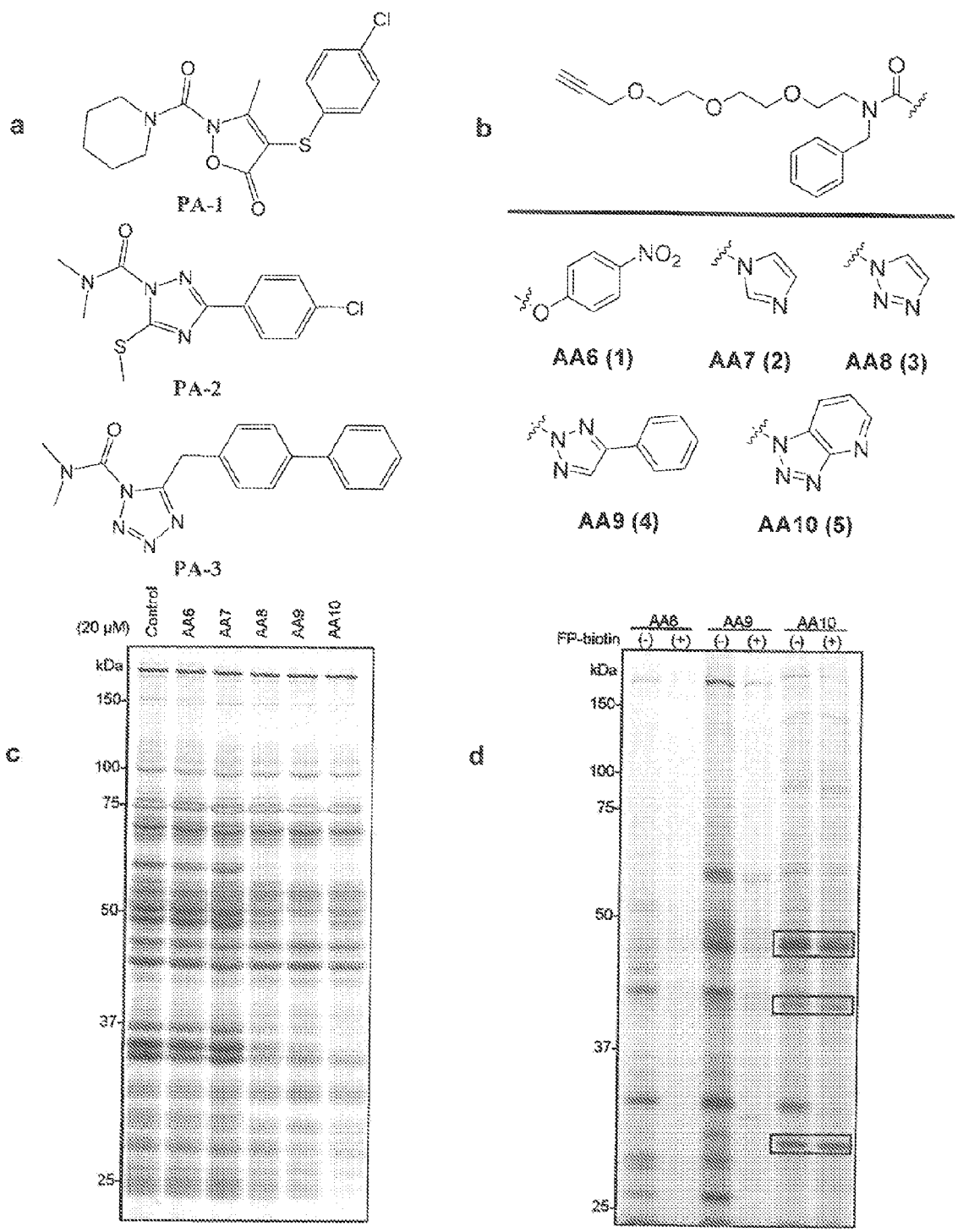
FIG. 1 illustrates competitive ABPP with N-heterocyclic urea (NHU) activity-based probes AA6-AA10. (a) Structures of previously reported prior art serine hydrolase inhibitors from the NHU class. (b) Structures of carbamate- and NHU-alkyne probes with various leaving groups. (c) Competitive ABPP of AA6-AA10 in the mouse brain membrane proteome. Brain membranes were incubated with 20 µM of AA6-AA10 or DMSO for 30 minutes at 37° C. Proteomes were then labeled with the SH-directed ABPP probe FP-Rh (2 µM, 30 min, 25° C.), separated by SDS-PAGE, and FP-Rh-labeled proteins detected by in-gel fluorescence scanning. This fluorescent gel and all gels in subsequent Figures are shown in grayscale. (d) Profiling the direct targets of AA6-AA10 (20 µM, 30 minutes at 37° C.) in mouse brain membranes in the presence or absence of the SH-directed probe FP-biotin (20 µM, 30 minutes at 37° C.). AA6-AA10-labeled proteins were detected by reaction with an azide-Rh tag under click chemistry conditions. Targets of AA10 that are not competed by FP-biotin are highlighted with boxes.

Provided herein are compounds that, in at least some embodiments, modulate one or more serine hydrolases (SH). For example, provided herein are compounds that may irreversibly inactivate SH, e.g. using for example, the N1- and N2-carbamoyl-1,2,3-triazole inhibitor compounds described herein (also referred to herein as 1,2,3-triazole ureas). Such disclosed compounds may exhibit negligible cross-reactivity with other protein classes. For example, compounds provided herein may selectively inhibit enzymes from diverse branches of the SH family, including peptidases (e.g., APEH), lipases (e.g., DAGLB, PAFAH2), and uncharacterized hydrolases (e.g, ABHD11), with exceptional potency (sub-nM) and efficacy (<1 mg/kg) in cells and mice. For example, provided herein are 1,2,3-triazole urea compounds that are a pharmacologically privileged chemotype for SH inhibition and show broad activity across the superfamily coupled with tunable selectivity for individual enzymes.

For example, compounds provided herein may inhibit one or more serine hydrolase enzymes characterized as peptidases, lipases, thioesterases, and amidases. Non-limiting examples of peptidases include N-acylaminoacyl-peptide hydrolase (APEH), lysosomal pro-X carboxypeptidase (PRCP), and cathepsin A (CTSA). Non-limiting examples of lipases, which as used herein also encompasses phospholipases, include diacylglycerol lipases (e.g., DAGLB), arylacetamide deacetylase-like 1 (AADACL1), alpha/beta-hydrolase domain 6 (ABHD6), esterase D (ESD), platelet-activating factor acetylhydrolase 2 (PAFAH2), lysosomal phospholipase A3 (LYPLA3), and alpha/beta-hydrolase domain 12 (ABHD12). Non-limiting examples of thioesterases include lysosomal phospholipase A1 (LYPLA1) and lysosomal phospholipase A2 (LYPLA2). A non-limiting example of an amidase is fatty acid amide hydrolase (FAAH). In addition, serine hydrolase enzymes inhibited by the N1-carbamoyl-1,2,3-triazole compounds of the invention include uncharacterized serine hydrolase enzymes such as alpha/beta-hydrolase domain 11 (ABHD11), alpha/beta-hydrolase domain 13 (ABHD13), an HLA-B associated transcript 5 (BATS). In some embodiments, a provided N1- or N2-carbamoyl-1,2,3-triazole compound is capable of inhibiting a single serine hydrolase enzyme, while in other embodiments, a N1- or N2-carbamoyl-1,2,3-triazole compound can inhibit multiple serine hydrolases. Preferably, the N1- or N2-carbamoyl-1,2,3-triazole compound selectively inhibits serine hydrolase enzymes in preference to other enzyme types.

The present invention provides, for example, inhibitors of a wide variety of serine hydrolase enzymes. The inhibitors of the present invention are N1- and N2-carbamoyl-1,2,3-triazole compounds such as those of Formula (I), (II), (III), (IV) and related formulas as described herein:

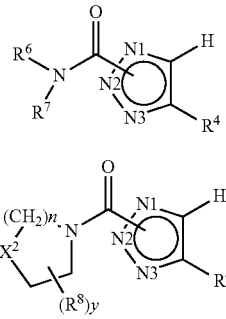

(I)

(II)

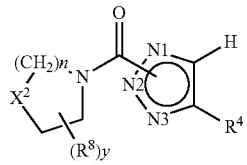

(III)

(IV)

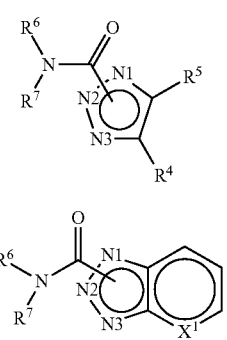

in which each of $R^4$ and $R^5$ independently is selected from the group consisting of H, alkyl, cycloalkyl, —C(O)E, —C(O)OE, —C(O)NE$_2$, —CN, —N(E)C(O)E, —N(E)C(O)OE, —SO$_v$E, —SO$_v$NE$_2$, ESO$_v$N(E)-, —N(E)SO$_v$E, —SO$_3$E, alkenyl, alkynyl, aryl, and a heterocyclic group, wherein v is 0, 1, or 2; or in Formula (I), $R^4$ and $R^5$ together with the carbon to which they are attached form a 5 or 6-membered ring, preferably an aromatic or heteroaromatic ring; each E independently is H, alkyl, or aryl; and each of $R^6$ and $R^7$ in Formula (I) independently is selected from the group consisting of alkyl, alkenyl, alkynyl, aryl, and a heterocyclic group; or $R^6$ and $R^7$ together with the nitrogen to which they are attached form a 5 or 6-membered heterocyclic ring. Each alkyl, cycloalkyl, alkenyl, alkynyl, aryl, heterocyclic group, aromatic ring, heteroaromatic ring, and 5 or 6-membered ring in the compounds of Formula (I), (II), (III) and (IV) optionally can be substituted by one or more substituent selected from the group consisting of OH, halogen, nitro, —C(O)E, —C(O)OE, —C(O)NE$_2$, —CN, —SO$_v$E, —SO$_v$NE$_2$, ESO$_v$N(E)-, —N(E)SO$_v$E, —SO$_3$E, —NE$_2$, —N(E)OE, —N(E)C(O)E, —N(E)C(O)OE, —N(E)C(O)NE$_2$, —OC(O)NE$_2$, —OC(O)OE, alkyl, cycloalkyl, alkenyl, alkynyl, alkoxy, fluoroalkyl, fluoroalkoxy, aryl, aryloxy, heteroaryl, poly(ethyleneoxy), alkynyl-terminated poly(ethyleneoxy), a fatty acid, a carbohydrate, an amino acid, and a polypeptide, wherein v is 0, 1, or 2. In Formula (II), $X^1$ is CH or N. In Formula (IV), n is 1 or 2; $X^2$ is C, O, or N; y is 0, 1, 2, 3, or 4; and each $R^8$ independently is selected from the group consisting of OH, halogen, nitro, —C(O)E, —C(O)OE, —C(O)NE$_2$, —CN, —SO$_v$E, —SO$_v$NE$_2$, ESO$_v$N(E)-, —N(E)SO$_v$E, —SO$_3$E, —NE$_2$, —N(E)OE, —N(E)C(O)E, —N(E)C(O)OE, —N(E)C(O)NE$_2$, —OC(O)NE$_2$, —OC(O)OE, alkyl, cycloalkyl, alkenyl, alkynyl, alkoxy, fluoroalkyl, fluoroalkoxy, aryl, aryloxy, heteroaryl, poly(ethyleneoxy), alkynyl-terminated poly(ethyleneoxy), a fatty acid, a carbohydrate, an amino acid, and a polypeptide, wherein v and E are as defined above.

As used herein, Formulas (I), (II), (III), and (IV) each denote both the N1 and the N2 regioisomers of the carbamoyl-1,2,3-triazole compounds. By way of example, Formula (I) is equivalent to Formulas (Ia) and (Ib), respectively the N1-carbamoyl and N2-carbamoyl regioisomers:

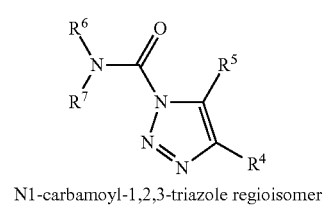

(Ia)

N1-carbamoyl-1,2,3-triazole regioisomer

-continued

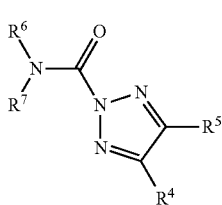

N2-carbamoyl-1,2,3-triazole regioisomer.

In another embodiment, the compounds of Formula (I) may be selected from compounds represented by:

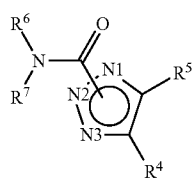

wherein $N_1$, $N_2$, and $N_3$ are nitrogen atoms at the 1-, 2-, and 3-positions of the triazole ring, respectively;

each of $R^4$ and $R^5$ independently is selected from the group consisting of H, halo, cyano, carboxyl, C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2), $C_{1-6}$alkyl (optionally substituted by one, two, or three substituents each independently selected from group consisting of halogen, hydroxyl, $C_{1-6}$alkoxy, carboxyl, cyano, phenyl (optionally substituted by one, two or three moieties independently selected from $R^c$)), $C_{3-6}$cycloalkyl (optionally substituted by one, two or three substituents independently selected from the group consisting of halogen, cyano, hydroxyl, or $C_{1-6}$alkyl), phenyl (optionally substituted by one, two or three moieties independently selected from $R^d$), naphthyl (optionally substituted by one, two or three moieties independently selected from $R^d$), $C_{2-6}$alkenyl, or $C_{2-6}$alkynyl, wherein when $R^5$ is phenyl, $R^4$ is H;

each of $R^6$ and $R^7$ independently is selected from the group consisting of $C_{1-12}$alkyl (optionally substituted by one, two, or three substituents each independently selected from group consisting of halogen, hydroxyl, $C_{1-6}$alkoxy, cyano, phenyl (optionally substituted by one, two or three moieties independently selected from $R^c$), and a fluorescent dye), $C_{2-10}$alkenyl, $C_{2-10}$alkynyl, —(CH$_2$—CH$_2$—O)$_q$—$C_{2-6}$alkynyl (where q is 1 to 10), or phenyl (optionally substituted by one, two, or three moieties independently selected from $R^c$);

or $R^6$ and $R^7$ together form a 5 or 6-membered heterocyclic ring A, optionally having one additional heteroatom moiety independently selected from $NR^a$, O, or S; wherein A is optionally substituted on one or two carbons by a substituent independently selected from the group consisting of halo, hydroxyl, $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), $R^a$—S(O)$_v$— (wherein v is 0, 1 or 2), $C_{1-6}$alkyl (optionally substituted by one, two, or three substituents each independently selected from group consisting of halogen, hydroxyl, cyano, $C_{1-6}$alkoxy (optionally substituted by one, two or three halogens), and phenyl (optionally substituted by one, two or three moieties independently selected from $R^c$)), and phenyl (optionally substituted by $R^c$);

$R^a$ and $R^b$ may be independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2);

$R^d$ is selected from the group consisting of phenyl (optionally substituted by $R^c$), phenyloxy (optionally substituted by $R^c$), halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2); and pharmaceutically acceptable salts thereof.

For example, contemplated herein are compounds represented by:

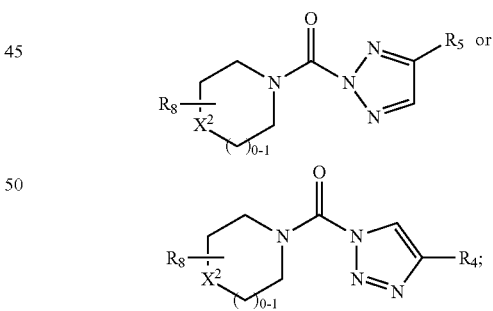

wherein $X^2$ is $CHR^8$, O, or $NR^a$;

$R^8$ is independently selected, for each occurrence, from the group consisting of H, $C_{1-6}$alkyl (optionally substituted by one, two, or three substituents each independently selected from group consisting of halogen, hydroxyl, $C_{1-6}$alkoxy (optionally substituted by one, two or three halogens), and phenyl (optionally substituted by one, two or three moieties independently selected from $R^c$)), and phenyl (optionally substituted by one, two, or three substituents each independently selected from $R^c$);

$R^4$ is selected from the group consisting of H, phenyl (optionally substituted by $R^c$), biphenyl (optionally substituted by $R^c$), phenyloxyphenyl (optionally substituted by $R^c$), naphthyl (optionally substituted by $R^c$), or $C_{1-6}$alkyl (optionally substituted by one, two, or three substituents each independently selected from hydroxyl, halo, and phenyl (optionally substituted by $R^c$));

$R^5$ is selected from the group consisting of H, phenyl (optionally substituted by $R^c$), biphenyl (optionally substituted by $R^c$), phenyloxyphenyl (optionally substituted by $R^c$), naphthyl (optionally substituted by $R^c$), or $C_{1-6}$alkyl (optionally substituted by one, two, or three substituents each independently selected from hydroxyl, cyano, halo, and phenyl (optionally substituted by $R^c$). $X^2$ may be, for example, $CH_2$.

In an embodiment, $R^8$ is benzyl.

In another embodiment, $R^4$ or $R^5$ is diphenylmethanol, 4-phenyloxyphenyl, or phenyl or naphthyl wherein phenyl or naphthyl may be optionally substituted by a moiety selected from the group consisting of halo, hydroxyl, carboxyl, $NO_2$, $C_{1-6}$alkyl (optionally substituted by one, two, or three substituents each independently selected from hydroxyl, cyano, or halo), and $C_{1-6}$alkoxy (optionally substituted by one, two, or three substituents each independently selected from hydroxyl, cyano, and halo).

For example, contemplated herein are compounds such as

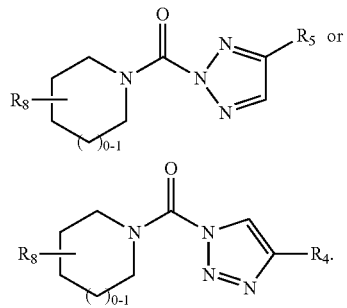

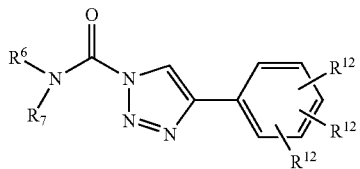

where $R^8$ and $R^4$ may be defined as variously disclosed above. In some embodiments, $R^4$ is H or $R^5$ is H. A contemplated compound may be represented by:

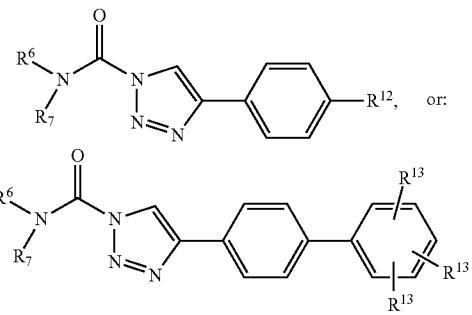

wherein:

$R^6$ and $R^7$ together with the nitrogen form a 5 or 6-membered heterocyclic ring A, wherein A is optionally substituted on one or two carbons by a substituent independently selected from the group consisting of $C_{1-6}$alkyl (optionally substituted by one, two, or three substituents each independently selected from group consisting of halogen, hydroxyl, $C_{1-6}$alkoxy (optionally substituted by one, two or three halogens), cyano, and phenyl (optionally substituted by one, two or three moieties independently selected from $R^c$);

$R^{12}$, independently for each occurrence, is selected from the group consisting of H, halo, nitro, $C_{1-6}$alkyl (optionally substituted by one, two, or three substituents selected from halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, phenyl (optionally substituted by halo, nitro, $C_{1-6}$alkoxy (optionally substituted by one, two, or three halogens), —COOH, or $C_{1-6}$alkyl (optionally substituted by one, two, or three substituents selected from halogens, cyano, or hydroxyl)) or phenyloxy (optionally substituted by halo, nitro, $C_{1-6}$alkoxy (optionally substituted by one, two, or three halogens), —COOH, or $C_{1-6}$alkyl (optionally substituted by one, two, or three substituents selected from halogens, cyano, or hydroxyl)).

Alternatively, for example, a compound may be represented by:

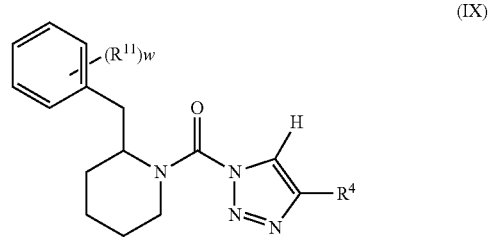

wherein:

$R^{12}$, independently for each occurrence, is selected from the group consisting of H, halo, nitro, $C_{1-6}$alkyl (optionally substituted by one, two, or three substituents selected from $R^c$), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, phenyl (optionally substituted by one, two, or three substituents selected independently from the group consisting of $R^c$)) or phenyloxy (optionally substituted by halo, nitro, $C_{1-6}$alkoxy (optionally substituted by one, two, or three halogens), —COOH, or $C_{1-6}$alkyl (optionally substituted by one, two, or three substituents selected from halogens, cyano, or hydroxyl); and $R^{13}$, independently for each occurrence is selected from the group consisting of H, halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), and $R^a$—S(O)$_v$— (wherein v is 0, 1 or 2).

In addition, some contemplated triazole compounds may include compounds of Formula (IX):

(IX)

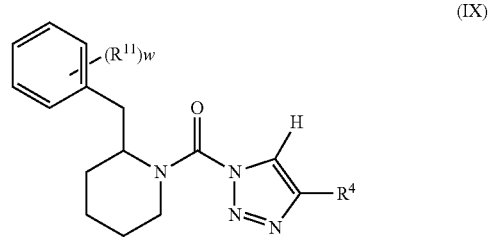

wherein w is 1, 2, 3, 4, or 5, and each $R^{11}$ independently is selected from the group consisting of OH, halogen, nitro, $C_{1-6}$alkyl, $C_{1-6}$alkoxy, $C_{1-6}$-fluoroalkyl, $C_{1-6}$-fluoroalkoxy, phenyl, or phenyloxy. For example, w is 1 and $R^{11}$ is H. In some embodiments, $R^4$ is phenyl or biphenyl, optionally substituted with one, two, or three substituents each independently selected from the group consisting of: $C_{1-6}$alkyl, $C_{1-6}$hydroxyalky, $C_{1-6}$alkoxy, $C_{1-6}$ perfluoroalkoxy, halogen, and hydroxyl.

Contemplated herein is a compound represented by:

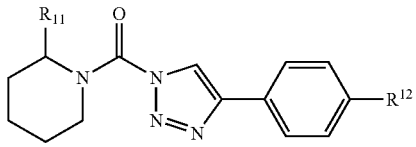

wherein $R^{11}$ is $C_{1-6}$alkyl substituted by phenyl, wherein $R^{11}$ is optionally substituted by one, two or three substituents selected from $R^c$;

$R^{12}$, independently for each occurrence, is selected from the group consisting of H, halo, nitro, $C_{1-6}$alkyl (optionally substituted by one, two, or three substituents selected from $R^c$), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, phenyl (optionally substituted by one, two, or three substituents selected independently from the group consisting of $R^c$)) or phenyloxy (optionally substituted by halo, nitro, $C_{1-6}$alkoxy (optionally substituted by one, two, or three halogens), —COOH, or $C_{1-6}$alkyl (optionally substituted by one, two, or three substituents selected from halogens, cyano, or hydroxyl);

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2); and pharmaceutically acceptable salts thereof.

Provided herein, in a different embodiment, are compounds represented by:

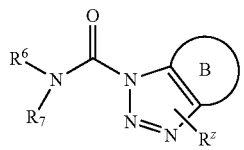

wherein B may be present or absent, and when present is a 5-6 membered heterocyclic ring having one or two heteroatoms each selected from N, O or S;

$R^7$ is $C_{1-6}$alkyl, optionally substituted by one or two substituents selected from halo and phenyl (optionally substituted by one, two, or three substituents selected from $R^c$);

$R^6$ is $C_{1-12}$alkyl substituted by a fluorescent dye and optionally substituted by one, two, or three substituents each independently selected from group consisting of halogen, hydroxyl, $C_{1-6}$alkoxy, cyano, and phenyl (optionally substituted by one, two or three moieties independently selected from $R^c$), $C_{2-10}$alkenyl substituted by a fluorescent dye, $C_{2-10}$alkynyl, substituted by a fluorescent dye, and —(CH$_2$—CH$_2$—O)$_q$—$C_{2-6}$alkynyl (where q is 1 to 10);

$R^z$ is selected from the group consisting of H, halo, cyano, carboxyl, C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2), $C_{1-6}$alkyl (optionally substituted by one, two, or three substituents each independently selected from group consisting of halogen, hydroxyl, $C_{1-6}$alkoxy, carboxyl, cyano, phenyl (optionally substituted by one, two or three moieties independently selected from $R^c$)), $C_{3-6}$cycloalkyl (optionally substituted by one, two or three substituents independently selected from the group consisting of halogen, cyano, hydroxyl, or $C_{1-6}$alkyl), phenyl (optionally substituted by one, two or three moieties independently selected from $R^d$), naphthyl (optionally substituted by one, two or three moieties independently selected from $R^d$), $C_{2-6}$alkenyl, or $C_{2-6}$alkynyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2);

$R^d$ is selected from the group consisting of phenyl (optionally substituted by $R^c$), phenyloxy (optionally substituted by $R^c$), halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^aR^bN$—, $R^aR^bN$—$SO_2$—, $R^aR^bN$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2); and pharmaceutically acceptable salts thereof.

For example, contemplated herein are compounds:

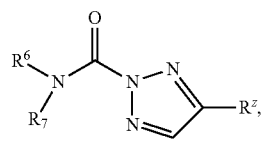

wherein $R^z$, $R^6$ and $R^7$ are described above. Such compounds may be used as probes for serine hydrolase identification, and/or identifying serine hyrolase inhibition.

Contemplated fluorescent dyes make be linked to a contemplated compound by a linker moiety that allows for covalent attachment to contemplated compounds, where for example the contemplated has an e.g. an alkyl moiety that is optionally substituted by —NH$_2$ or other reactive moiety. Fluorescent dyes contemplated for use herein include BODIPY (boron-dipyrromethene) dyes, for example, BODIPY FL, BODIPY R6G, BODIPY TMR, BODIPY 581/591, BODIPY TR, BODIPY 630/650, BODIPY 650/665, fluorone dyes such as rhodamine, acridine dyes, cyanine dyes, oxazine dyes or phenanthridine dyes. For example, contemplated fluorescent dyes may include a carboxylic acid that can react with contemplated compounds to form an amide bond, thus covalently attaching the fluorescent dye to a contemplated compound.

In some embodiments, an alkyne moiety, e.g., a terminal alkyne, can be linked to the triazole urea compound, for example, to provide a handle for copper-catalyzed azide-alkyne click ligation. In some embodiments, the triazole urea compound can be linked to a biotin molecule.

Procedures for making compounds described herein are provided below with exemplary reference to Scheme 1. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art; for example, see Greene, Wuts, Protective Groups in Organic Synthesis. 2nd Ed. (1999). Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

A general synthetic strategy that may be used to prepare carbamate compounds of Formula (I), particularly compounds of Formula (III), is depicted in Scheme 1. The method comprises contacting an alkyne of Formula (V) with in-situ-formed azido methanol in the presence of a Cu(I) catalyst to form triazole (VI) via a copper(I)-catalyzed azide/alkyne click chemistry cycloaddition reaction, followed by base treatment remove the hydroxymethyl substituent and form a 1H-1,2,3-triazole of Formula (VII). Subsequently triazole (VII) is reacted with an activated carbamate of Formula (VIII) to afford the compound of Formula (III) as a mixture of N1- and N2-carbamoyl regioisomers, as set forth in Scheme I. The compound of Formula (III) typically is formed in an approximately 3 to 1 mixture of the N2-carbmate to the N1-carbamate. The N1 and N2 regioisomers can be separated, if desired, any suitable separation technique known to those of ordinary skill in the chemical synthesis arts (e.g., chromatography, crystallization, distillation, and the like, as may be appropriate based on the chemical and physical properties of the given material). In some embodiments, the N2 regioisomers are the preferred inhibitors.

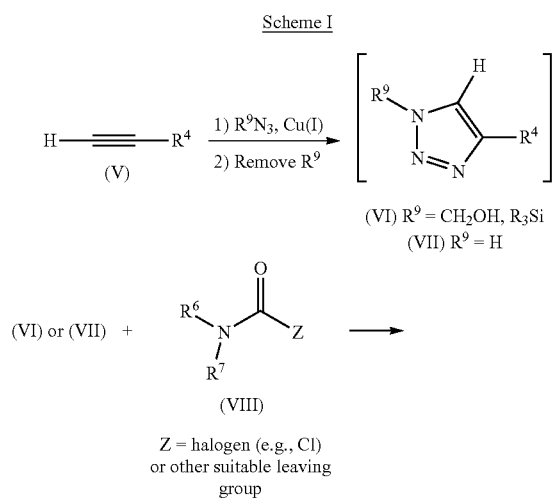

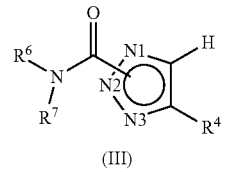

$R^4$, $R^6$, and $R^7$ in Formulas (V), (VI), (VII), and (VIII) in Scheme I, have the same meaning as the corresponding groups in Formulas (I), (II), (III), and (IV) variously defined herein. The compounds can optionally be substituted as described above, as well. $R^9$ is $CH_2OH$ or $R_3Si$; and R is alkyl. The azidomethanol used in Scheme I preferably is formed in situ by reaction of formaldehyde or a formaldehyde equivalent (e.g., paraformaldehyde or trioxane) with an azide salt (e.g., sodium or potassium azide). Alternatively, a trialkylsilyl azide (e.g., trimethysilyl azide) can be used in place of azidomethanol. The Cu(I) catalyst can comprise a Cu(I) salt, or can be formed in situ from a Cu(II) salt and a reducing agent for reducing Cu(II) to Cu(I), such as ascorbate, or can be provided by oxidation of the surface of metallic copper e.g., as described in U.S. Pat. Nos. 7,375,234 and 7,763,736 to Sharpless et al., which are incorporated herein by reference in their entirety. Z in Formula (VIII) is a leaving group, such as a halogen (preferably Cl), a substituted aryloxy group (e.g., phenyloxy group such as a 4-nitrophenyloxy or 2,4,6-trichlorophenyloxy group), a thio group (e.g., an alkylthio group or arylthio group), an N-heterocycle (e.g. N-succinimidyl group, an N-imiazolyl group), and the like. If desired, a suitable acylation catalyst, such as 4-N,N-dimethylaminopyridine (DMAP) or iodide can be added to facilitate the carbamoylation of the triazole. If a trialkylsilyl azide is used in place of azidomethanol, the carbamoylation reaction can be performed directly on the resulting trialkylsilyltriazole intermediate (VII), provided a Lewis acid catalyst is added.

DEFINITIONS

As used herein the term "alkyl" means a substituted or unsubstituted aliphatic hydrocarbon moiety. The alkyl groups can be linear, branched, cyclic, or a combination thereof. In some preferred embodiments, the alkyl groups of $R^4$, $R^5$, $R^6$ and $R^7$ comprise a $C_1$-$C_{18}$ alkyl group, such as a $C_1$-$C_{12}$, $C_1$-$C_{10}$, $C_1$-$C_8$, $C_1$-$C_6$, or $C_1$-$C_4$ alkyl group. The term "cycloalkyl" refers to an alkyl group as described above, which includes at least one carbon-based ring, i.e., a carbocyclic ring.

Modifiers of the form "$C_x$-$C_y$" and "$C_{x-y}$" designate that the selected alkyl, alkenyl, alkynyl, and alkoxy group has a molecular formula containing a minimum of x contiguous carbon atoms and a maximum of y contiguous carbon atoms, where x and y are specified integers.

The terms "alkenyl" and "alkynyl", as used herein refer to aliphatic hydrocarbon groups as described above, which comprise at least two contiguous carbon atoms and which contain at least one carbon-carbon double bond or carbon-carbon triple bond, respectively.

The terms "alkoxy", "fluoroalkoxy", and "aryloxy" and the like, refer to alkyl, fluoroalkyl, aryl, or other groups, respectively, which are linked to another moiety through an oxygen atom.

The alkyl, alkenyl, and alkynyl groups in the compounds of the present invention can be linear or branched, and in some cases can be carbocyclic in nature. The term "carbocyclic" refers to an alkyl, alkenyl, or alkynyl group comprising one or more hydrocarbon rings of from 3 to about 12 carbon atoms in size.

The terms "heterocycle" and "heterocyclic" refer to ring structures that include at least one heteroatom such as N, O, S, and the like, in addition to carbon atoms arranged in a cyclic structure. The presence of a carbon-carbon double bond or carbon-carbon triple bond may limit the size of any carbocyclic or heterocyclic rings in the compounds of the present invention. Non-limiting examples of heterocyclic groups include piperidine, piperazine, tetrahydrofuran, pyrrolidine, and morpholine groups.

The term "aryl" refers to a substituted or unsubstituted phenyl or naphthyl moiety, while the term "heteroaromatic" refers to a group comprising at least one 5 or 6-membered ring having aromatic character and comprising at least one heteroatom such as N, O or S, and at least one carbon atom within the ring. Non-limiting examples of heteroaromatic groups are well known in the art and include pyridine, pyrazine, pyrrole, pyrazole, imidazole, oxazole, isoxazole, triazole, thiophene, thiazole, furan, quinoline, and isoquinoline groups.

Terms comprising the modifier "fluoro", when used in reference to a hydrocarbon moiety, such as "fluoroalkyl" and "fluoroalkoxy", refer to hydrocarbon moieties in which one or more hydrogen atom has been replaced by a fluorine atom. Some examples of fluoroalkyl and fluoroalkoxy groups include trifluoromethyl and trifluoromethoxy groups, respectively.

The term "substituted" as used herein in reference to alkyl, aryl, heteroaryl, heterocyclic, and other groups, means that at least one hydrogen atom on carbon atom or heteroatom of an alkyl, alkenyl, alkynyl, aryl, heterocyclic, heteroaromatic, or other group, has been replaced by at least one halogen atom, hydroxyl group, nitro group, alkyl group, fluoroalkyl group, aryl group, heteroaryl group, fluoroaryl group, poly(ethyleneoxy) group, carbohydrate group, amino acid group, polypeptide group, and the like, as the case may be.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. Disclosed compounds may be administered to a mammal, such as a human, but may also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. Substituents around a carbocyclic or heterocyclic rings may be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds as disclosed herein which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atoms replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

Methods

The N1 and N2-carbamoyl-1,2,3-triazole compounds of the present invention are useful for inhibiting serine hydrolase enzymes, e.g., for purposes of evaluating enzyme reactivity and in some cases as pharmacological or pharmaceutical agents. Non-limiting examples of N1 and N2-carbamoyl-1,2,3-triazole compounds useful as serine hydrolase inhibitors include compounds of Formula (I), (II), (III), (IV), (IX), and related formulas as described herein.

Another aspect of the disclosure provides methods of modulating the activity of DAGLB, FAAH, ABHD11, and/or APEH. Contemplated methods, for example, comprise exposing said enzyme to a compound described herein. In some embodiments, the compound utilized by one or more of the foregoing methods is one of the generic, subgeneric, or specific compounds described herein, such as a compound of Formula I. The ability of compounds described herein to modulate or inhibit e.g., DAGLB can be evaluated by procedures known in the art and/or described herein. Another aspect of this disclosure provides methods of treating a disease associated with expression or activity of DAGLB or other serine hydrolase in a patient. For example, provided herein are compounds that may be selective in inhibiting a serine hydrolase (e.g. DAGLB), as compared to inhibition of other serine hydrolases e.g., FAAH, e.g. 10, 100, 1000 or more fold inhibition of DAGLB over FAAH.

Also contemplated herein are methods of treating and/or preventing in a patient in need thereof a disorder such as one or more of acute or chronic pain, obesity, metabolic disorders (such as syndrome X), vomiting or nausea, eating disorders such as anorexia and/or bulimia; dislipidaemia, neuropathy such as diabetic neuropathy, pellagric neuropathy, alcoholic neuropathy, Beriberi neuropathy, burning feet syndrome, neurodegenerative disorders such as multiple sclerosis, Parkinson's disease, Huntington's chorea, Alzheimer's disease, amyotrophic lateral sclerosis, epilepsy, sleep disorders, cardiovascular diseases, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g. myeloid, lymphoid or monocytic cancers), inflammatory disorders (e.g. bladder inflammation), including inflammatory pain, and/or psychological disorders including anxiety disorders (e.g., panic disorder, acute stress disorder, post-traumatic stress disorder, substance-induced anxiety disorders, obsessive-compulsive disorder, agoraphobia, specific phobia, social phobia. Contemplated methods include administering a pharmaceutically effective amount of a disclosed compound to a subject.

For example, provide herein is a method for treating chronic pain such as inflammatory pain, visceral pain, post operative pain, pain related to migraine, osteoarthritis, or rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

For example, contemplated herein are methods for treating neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents) in a patient in need thereof, comprising administering a pharmaceutically effective amount of a disclosed compound.

In certain embodiments, a disclosed compound utilized by one or more of the foregoing methods is one of the generic, subgeneric, or specific compounds described herein, such as a compound of Formula (I) as variously described herein.

Disclosed compounds may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a contemplated compound disclosed herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Compositions

The present invention also provides pharmaceutical compositions comprising the serine hydrolase inhibitors (SHIs) described herein. The pharmaceutical compositions comprise at least one disclosed compound, e.g. selected from compounds of Formula (I), (II), (III), (IV), (IX), and related formulas described herein, in combination with a pharmaceutically acceptable carrier, vehicle, or diluent, such as an aqueous buffer at a physiologically acceptable pH (e.g., pH 7 to 8.5), a non-aqueous liquid, a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the SHI.

In some embodiments, the pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), central (intracerebroventricular) administration, in a form suitable for administration by inhalation or insufflation. The compositions can, where appropriate, be provided in discrete dosage units. The pharmaceutical compositions of the invention can be prepared by any of the methods well known in the pharmaceutical arts. Some preferred modes of administration include intravenous (i.v.), intraperitoneal (i.p.), topical, subcutaneous, and oral.

Pharmaceutical formulations suitable for oral administration include capsules, cachets, or tablets, each containing a predetermined amount of one or more of the SHIs, as a powder or granules. In another embodiment, the oral composition is a solution, a suspension, or an emulsion. Alternatively, the SHIs can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the SHIs can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 100 millimolar, preferably at least about 1 nanomolar to about 10 millimolar.

Pharmaceutical compositions for topical administration of the SHIs to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the SHI in a flavored base, such as sucrose, acacia, or tragacanth; pastilles comprising the SHI in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

A pharmaceutical composition suitable for rectal administration comprises a SHI of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a SHI of the invention in combination with a carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a SHI of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the SHI. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the SHI. Alternatively, pharmaceutical compositions for administration by inhalation or insufflation can be provided in the form of a dry powder composition, for example, a powder mix of the SHI and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The SHIs of the present invention will be included in the compositions within a therapeutically useful and effective concentration range, as determined by routine methods that are well known in the medical and pharmaceutical arts. For example, a typical composition can include one or more of the SHIs at a concentration in the range of at least about 0.01 nanomolar to about 1 molar, preferably at least about 1 nanomolar to about 100 millimolar.

Optionally, the pharmaceutical compositions of the present invention can include one or more other therapeutic agent, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a SHI of the present invention.

EXAMPLES

The following discussion and examples serve to further illustrate certain aspects of the compounds and methods of the present invention, and are not intended to limit the scope of the invention or inventions claimed and described herein. In the following examples and discussion, the regioisomer of the N-carbamoyl-1,2,3-triazole inhibitors tested and discussed below is the N2-carbamoyl isomer, unless otherwise specifically specified.

Example A

Class-Specific Inhibition of SHs

The tetrazole urea LY2183240 (PA1) is a potent inhibitor of numerous SHs, including the endocannabinoid-degrading enzymes fatty acid amide hydrolase (FAAH), monoacylglycerol lipase (MAGL or MGLL), and α/β-hydrolase 6 (ABHD6). Tetrazole urea PA1 inhibits FAAH by covalent, carbamoylation of the enzyme's serine nucleophile. The isoxazolonyl urea PA2 and 1,2,4-triazole urea PA3, have been reported as inhibitors of hormone-sensitive lipase (LIPE), with limited selectivity data are available on these compounds.

Figure 9:
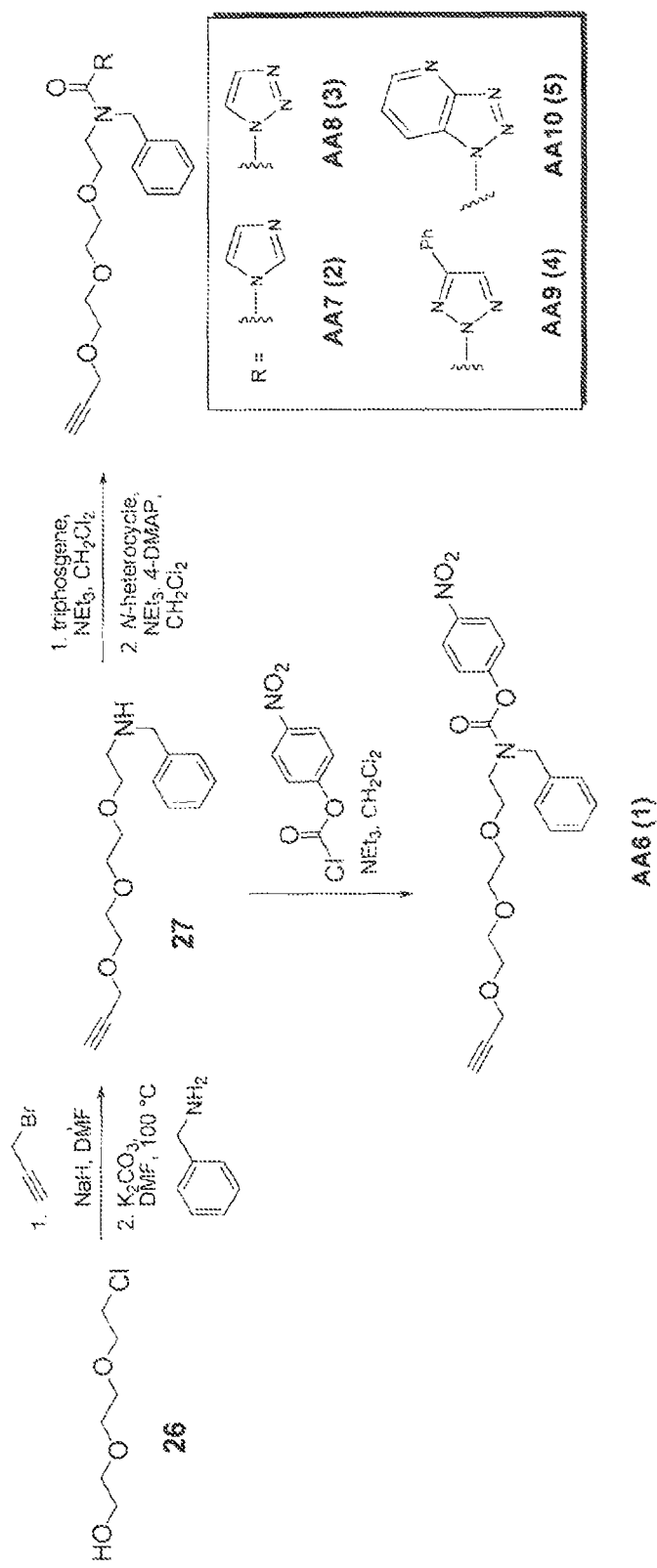
FIG. 9 illustrates a divergent synthetic route to alkyne-modified probes AA6-10.

To investigate the effect of electrophylicity on the reactivity of NHUs, alkyne-modified agents AA6-10 (see FIG. 1b and FIG. 9 for structures) were prepared, which differ in electrophilicity due to variations in the leaving group. A competitive ABPP experiment was performed by treating a mouse brain membrane proteome with AA6-10 (20 μM, 30 min), followed by the SH-directed activity-based probe FP-rhodamine (FP-Rh, 2 μM, 30 min), separation by SDS-PAGE, and detection of FP-Rh-labeled proteins by in-gel fluorescence scanning (FIG. 1c). The carbamate AA6 and the imidazole AA7 showed little to no detectable inhibition of SHs, whereas 1,2,3-triazoles AA8-AA10 blocked the FP-Rh-labeling of several proteins. The reactivity of these compounds followed the trend of electrophilicity imparted by their leaving groups, with the pyridyl triazole AA10 being the most acidic and reactive NHU. To assess the cross-reactivity of 1,2,3-triazole ureas AA8-AA10 with other protein classes, a second, complementary competitive ABPP experiment was performed. Here, the NHUs themselves were used as probes to assess whether their proteome reactivity profiles could be blocked by pre-incubation with FP-biotin (20 μM). Visualization of NHU-labeled proteins was achieved by click chemistry conjugation of the terminal alkyne group to an azide-Rh reporter tag. FP-biotin competed the labeling of all proteins modified by triazoles AA8 and AA9 (FIG. 1d), whereas several of the protein targets of the most electrophilic NHU AA10 were not sensitive to FP-biotin competition (FIG. 1d, boxes), suggesting that they correspond to labeling of non-SH proteins. These data demonstrate that the monocyclic triazole ureas AA8 and AA9 possess the desired degree of electrophilicity to inhibit a number of SHs in proteomes, but, at the same time, avoid modification of proteins outside of the SH class.

Example B

Inhibition of SHs in Living Cells

Figure 2:
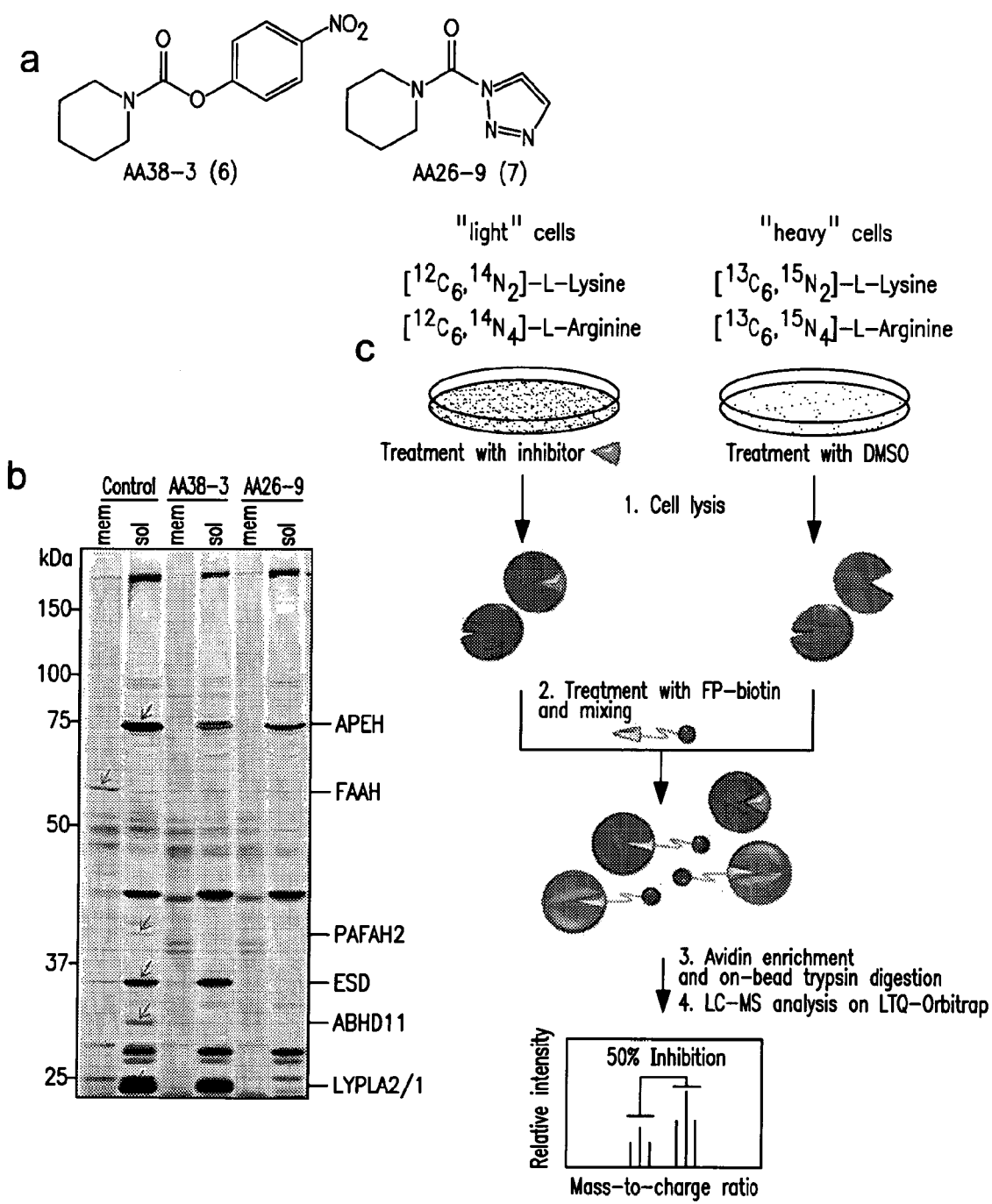
FIG. 2 illustrates comparative ABPP of piperidine-based carbamate (AA38-3) and triazole urea (AA26-9) inhibitors. (a) Structures of AA38-3 and AA26-9. (b) Competitive ABPP of AA38-3 and AA26-9 in BW5147-derived murine T-cell hybridoma cells. Cells were cultured with 20 µM inhibitor or DMSO as a control for 4 hours (h), lysed, separated into soluble components and analyzed by competitive gel-based ABPP. Blue and red arrows mark SHs that were inhibited by AA26-9 and both AA26-9 and AA38-3, respectively. (c) Schematic representation of a competitive ABPP-SILAC experiment. Isotopically "light" and "heavy" mouse T-cells are treated with inhibitor and DMSO, respectively, for 4 h. Cells are lysed, proteomes are treated with FP-biotin, and combined in a 1:1 ratio. Biotinylated proteins are enriched, trypsinized, and analyzed by LC-MS/MS. SH activities are quantified by comparing intensities of light and heavy peptide peaks. (d) Identification of SH targets for AA38-3 (top) and AA26-9 (bottom) in mouse T-cells by ABPP-SILAC. Cells were cultured with inhibitor (20 µM) or DMSO as a control for 4 h prior to analysis by competitive ABPP-SILAC. Asterisks mark SHs that were inhibited by >75%. Bars represent the means±s.e.m of light/heavy-ratios of identified tryptic peptides in both soluble and membrane proteomes.

The SH family-wide reactivity of 1,2,3-triazole ureas were compared with a classical carbamate inhibitor. Prior art carbamate AA38-3 (6) and comparative triazole AA26-9 (7) (FIG. 2a), both based on a piperazine scaffold shown previously to inhibit SHs in the context of p-nitrophenyloxy carbamate, were prepared and then mouse BW5147 T-cell hybridoma cells were treated with each inhibitor at 20 μM for 4 h. Cells were then lysed and analyzed by competitive ABPP with the FP-Rh probe. Gel-based ABPP detected SHs that were inhibited by both AA38-3 and AA26-9 (FIG. 2b, arrows), as well as a substantial number of additional SHs that were only inhibited by the triazole AA26-9 (FIG. 2b, arrows). To identify the inhibited enzymes, an advanced quantitative mass spectrometry (MS)-based platform was used, and is referred to as competitive ABPP-SILAC (FIG. 2c). Competitive ABPP-SILAC is essentially a merger the ABPP-MudPIT method with the stable isotope labeling of amino acids in culture (SILAC) technique, which has been used to identify enzymes targets of activity-based probes and small-molecule-binding proteins in cell lysates. While previous competitive ABPP-MudPIT experiments have relied on the semi-quantitative method of spectral counting to identify inhibitor-sensitive enzymes, competitive ABPP-SILAC allows for more precise quantitation of inhibited enzymes by calculating the isotopic ratios of peptides from control-treated and inhibitor-treated cells.

Figure 10:
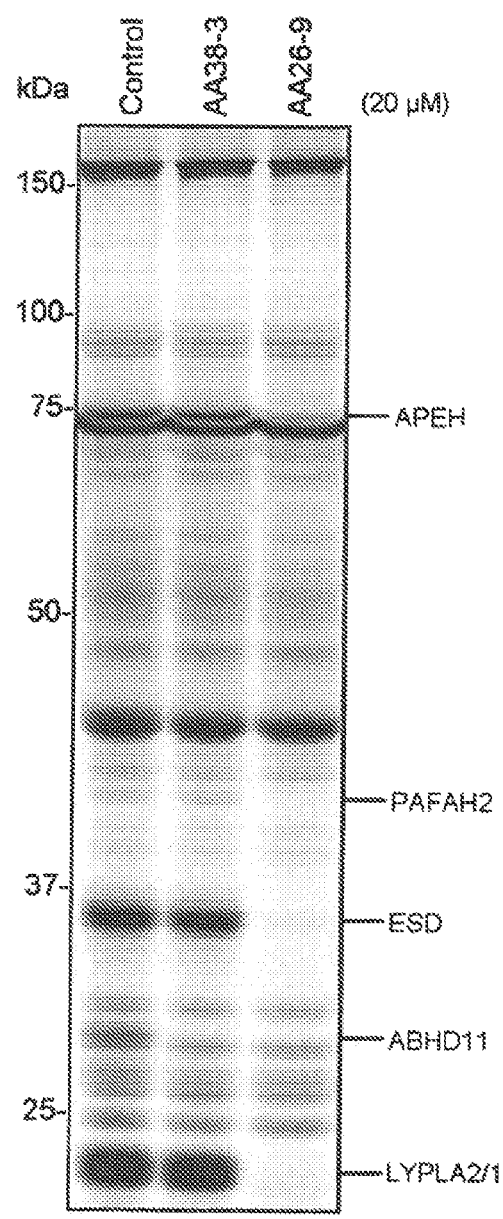
FIG. 10 provides competitive ABPP profile for inhibitors AA38-3 and AA26-9 in vitro. Soluble mouse T-cell proteome (1 mg/mL) was incubated with 1 µM inhibitor or DMSO for 4 h at 37° C., after which the samples were treated with FP-Rh (2 µM) for 30 minutes at 25° C. and analyzed by gel-based ABPP.

Briefly, mouse T-cells were cultured under 'light' (with $^{12}C_6^{14}N_2$-lysine and $^{12}C_6^{14}N_4$-arginine containing medium) and 'heavy' conditions (with $^{13}C_6^{15}N_2$-lysine and $^{13}C_6^{15}N_4$-arginine). The light and heavy cells were treated with inhibitor and DMSO, respectively, and then harvested, lysed, separated into soluble and membrane fractions, and treated with FP-biotin (5 μM, 90 min). Light and heavy fractions were then mixed, enriched with avidin, digested on-bead with trypsin, and analyzed by LC-MS/MS using an LTQ-Orbitrap instrument. Light and heavy signals were quantified from parent ion peaks (MS1) and the corresponding proteins identified from product ion profiles (MS2) using the SEQUEST search algorithm. The depicted bar graphs represent the average ratios of light/heavy tryptic peptides for each of the 46 SHs identified in mouse T-cells (FIG. 2d). While in situ treatment with carbamate AA38-3 inhibited three SHs (ABHD6, ABHD11, and FAAH), 15 SHs were inhibited by triazole urea AA26-9 (including the aforementioned three targets of AA38-3) (FIG. 2d). Notably, AA26-9-inhibited enzymes originated from diverse functional subclasses of SHs, including lipases/phospholipases (AADACL1, ABHD6, ESD, PAFAH2, LYPLA3), peptidases (APEH, PRCP, CTSA), thioesterases (LYPLA1, LYPLA2), an amidase (FAAH) and uncharacterized enzymes (ABHD11, ABHD13, BATS) (FIG. 8). Interestingly, 9 of these 15 triazole targets were not inhibited by any members of a 150+ carbamate library. Taking into account the predicted molecular masses of AA26-9-inhibited and AA38-3-inhibited SHs, as well as their sensitivity to one or both inhibitors, allowed for confident assignment of many of the SH signals on ABPP gels (FIG. 2b). Finally, similar inhibitor sensitivity profiles were observed with live cells (FIG. 2b) and cell homogenates (FIG. 10), indicating that reductions in FP-Rh labeling of SHs reflected direct inhibition by AA26-9 and/or AA38-3 in situ, as opposed to indirect effects on the expression level of these enzymes.

Figure 11:
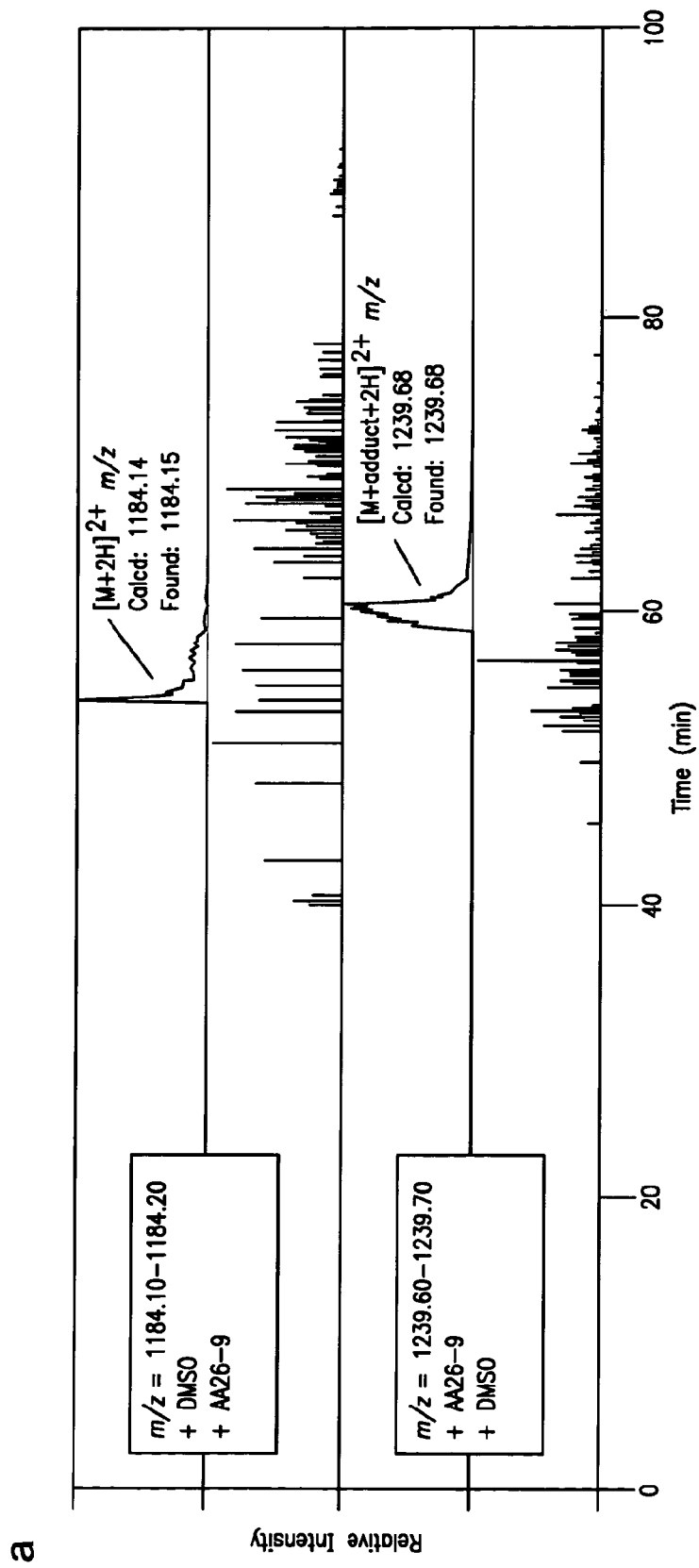
FIG. 11 describes identification of covalent adduct between the enzyme LYPLA1 and triazole urea inhibitor AA26-9. (a) Extracted ion chromatograms (EIC) of the unmodified (top) and AA74-1-modified (bottom) LYPLA1 active-site peptide containing serine nucleophile S114. Recombinant, purified LYPLA1 (50 µM) was treated with DMSO or AA26-9 (100 µM) prior to MS analysis. The mass window for each EIC, the detected high-resolution mass for each peak, and the charge state for each tryptic peptide are indicated. (b) MS/MS spectra for the unmodified and AA74-1-modified active site peptides. Diagnostic ions are identified. All ions are in the 1+ charge state unless otherwise indicated. The structure of the proposed carbamoylated adduct is shown.

To verify the expected covalent mode of inhibition by AA26-9 (carbamoylation of the serine nucleophile of SHs), recombinant, purified LYPLA1 was treated with this compound or DMSO and subjected the reaction mixtures to trypsin digestion, alkylation/reduction protocols, and analysis by LC-MS/MS. An active-site peptide containing the carbamoylated serine nucleophile of LYPLA1 (S114) was identified exclusively in the AA26-9-treated sample, while only the unmodified peptide was observed in the control experiment (FIG. 11). No additional carbamoyl adducts were observed with LYPLA1, as evidenced from unchanged parent ion profiles for other identified LYPLA1 tryptic peptides in AA26-9-treated versus DMSO-treated samples. MS2 profiles confirmed the site of carbamoylation as the catalytic serine S114 of LYPLA1 (FIG. 11).

These results, taken together, demonstrate that the 1,2,3-triazole urea is capable of inactivating numerous members of the SH family, exhibiting a target profile that surpasses in breadth that of the structurally related carbamate.

Example C

1,2,3-Triazole Ureas

Agents (AA26-1 through AA26-10) were prepared, as below, with distinct carbamoyl substituents combined with a uniform, unfunctionalized 1,2,3-triazole leaving group (FIG. 3a). Mouse T-cell proteomes were incubated in vitro with N1-carbamoyl-1,2,3-triazole compounds AA26-1 to AA26-10 (1 μM, 30 min) and analyzed by competitive ABPP. The individual triazole ureas showed markedly different SH reactivity profiles, with one agent, in particular, the pyrrolidine urea AA26-8 inhibiting several enzymes, including ABHD11, APEH, FAAH, PAFAH2, and LYPLA1 (FIG. 3b). Three of these enzymes, namely PAFAH2, ABHD11, and FAAH were also inhibited by morpholine urea AA26-5. Notably, most of these enzymes were more potently inhibited by AA26-5 and AA26-8 compared to the piperidinyl analogue AA26-9. The pyrrolidine- and morpholine-based scaffolds of AA26-8 and AA26-5 were selected as starting points for constructing a focused library of 1,2,3-triazole ureas, introducing substituents onto the triazole group to modify the selectivity for individual SHs.

Figure 12:
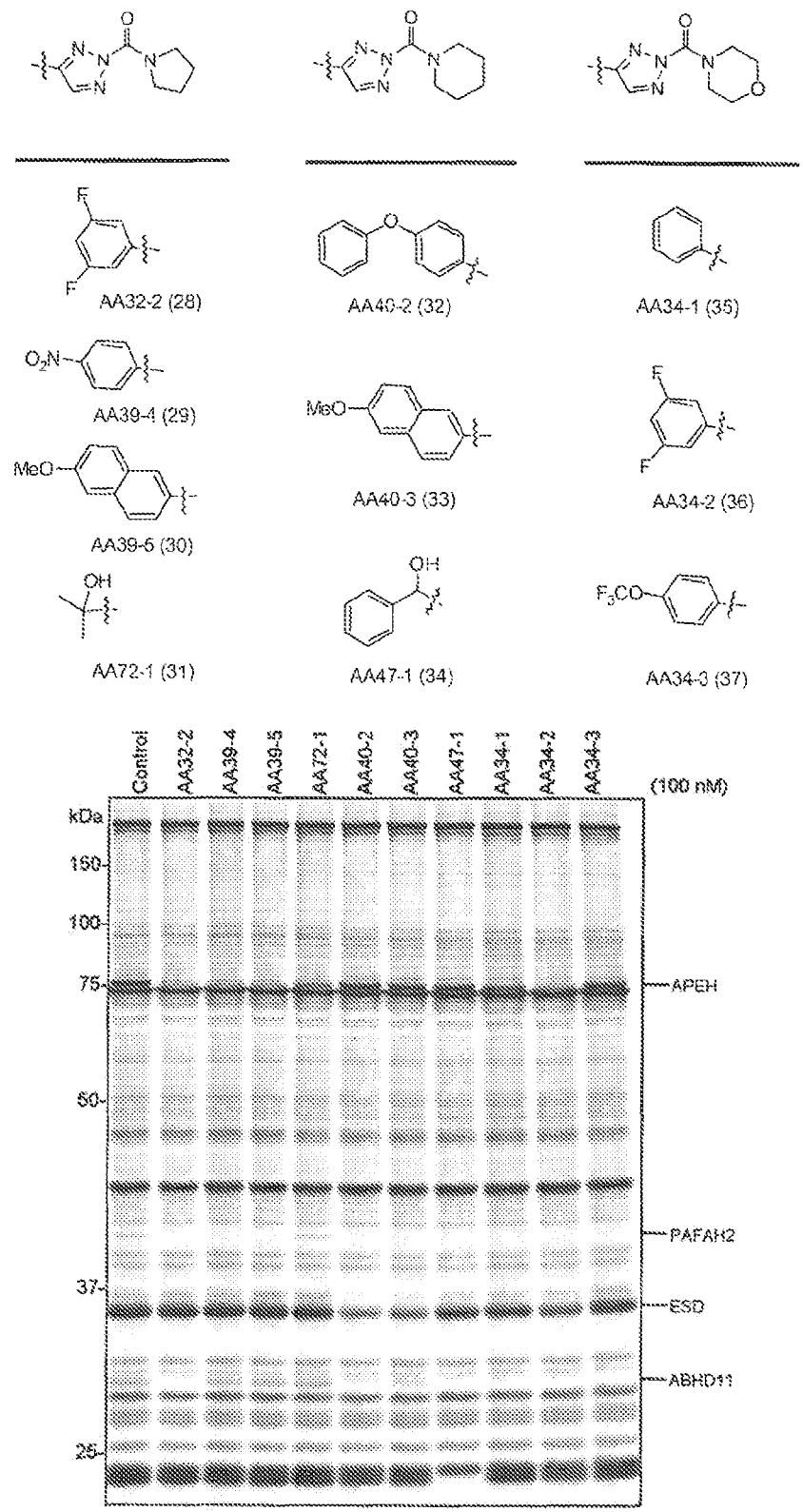
FIG. 12 illustrates structures and proteomic profiles for representative pyrrolidine, piperidine, and morpholine inhibitors with functionalized 1,2,3-triazole leaving groups. Soluble proteomes of mouse T-cells were incubated with 100 nM inhibitor or DMSO for 30 minutes at 37° C., after which the samples were treated with FP-Rh (2 µM) for 30 minutes at 25° C. and analyzed by gel-based ABPP.

A simple and efficient click chemistry approach was used to create substituted triazole ureas (FIG. 3c). In this two-step procedure, substituted alkynes were reacted with in situ-formed azidomethanol to yield 4-substituted triazoles, which were then carbamoylated to afford triazole urea products, as a mixture of N2- and N1-carbamoyl regioisomers, typically in a N2:N1 ratio of about 1.5:1 to about 3:1. The carbamoyl triazole regioisomers were separated by gel chromatography and used for subsequent experiments. A library of 25 different 4-aryl- and 4-alkyl triazole derivatives of AA26-5 and AA26-8 was prepared (representative structures are shown in FIG. 3d; see FIG. 12 for structures of additional members of the library). The compounds were screened at concentrations of 10 and 100 nM in mouse T-cell proteomes (FIG. 3e and FIG. 12). From this library, highly potent and selective inhibitors of APEH and PAFAH2 were identified. For instance, the biphenyl triazole AA39-2 (21) completely blocked PAFAH2 activity at 10 nM, while not inhibiting ABHD11, APEH, LYPLA1, or other SHs in T-cells at 100 nM. When substituted with bulky aliphatic groups, the triazole ureas generally showed higher preference for APEH, as exemplified by the 2,6-dimethylheptanol-substituted triazole in AA74-1 (23), which completely inhibited APEH at 10 nM, while not interacting with other SHs at 100 nM. In addition, 4-alkyl/aryl triazole ureas with good activity against ABHD11 were identified, including AA32-1 (17), AA39-3 (18), and AA32-4 (24), all of which completely blocked the activity of this enzyme at 100 nM, albeit non-selectively with respect to APEH and PAFAH2. The pyrrolidine carbamoyl group of AA32-4 was replaced with the larger and bulkier 2-(methoxymethyl)-piperidine to generate AA44-2 (25), which showed much improved potency for ABHD11 (complete inactivation at 10 nM) and no cross-reactivity with APEH, PAFAH2, or other SHs at 100 nM.

Figure 4:
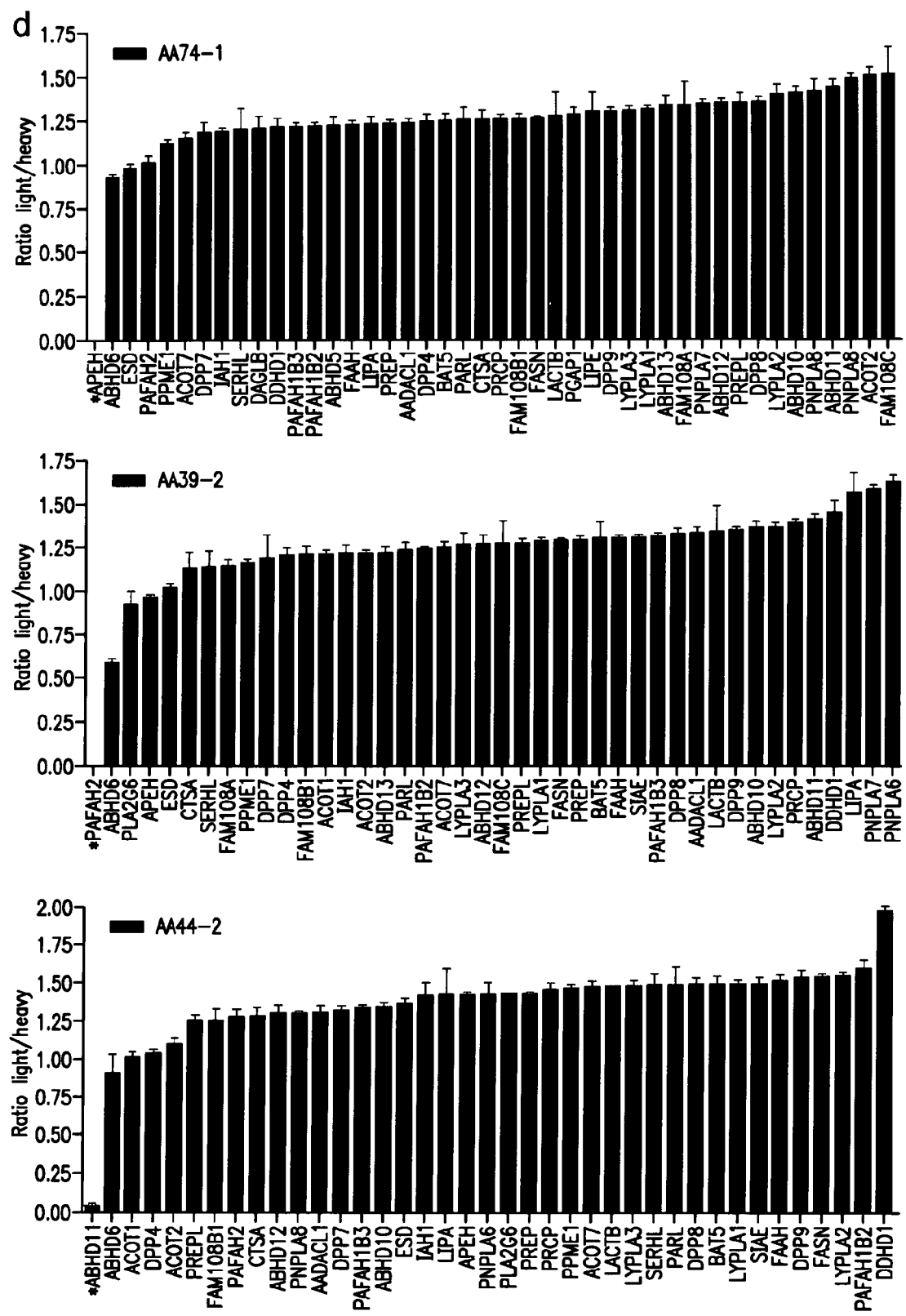
FIG. 4 provides in vitro and in situ characterization of triazole urea inhibitors AA74-1, AA39-2, and AA44-2 in mouse T-cells. (a) Competitive ABPP results for the three inhibitors in soluble (top) and membrane (bottom) proteomes of mouse T-cells after 30 minutes treatment at the indicated inhibitor concentrations. Inhibited SHs are highlighted with boxes. (b) Concentration-dependent inhibition curves for AA74-1, AA39-2, and AA44-2 against their respective SH targets. Calculated $IC_{50}$ values represent means±s.e.m for three independent experiments. (c) Confirmation that AA74-1, AA39-2, and AA44-2 inhibit their respective SH targets: APEH, PAFAH2, and ABHD11. SHs were recombinantly expressed in COS-7 or HEK-293 cells and transfected cell proteomes were treated with inhibitors at the indicated concentrations for 30 minutes at 37° C. and then analyzed by competitive gel-based ABPP. (d) ABPP-SILAC analysis of SH activities from inhibitor-treated mouse T-cells (in situ treatment with 3 nM AA74-1, AA39-2 or AA44-2 for 4 h). Asterisks mark the SH target of each compound, each of which was inhibited >97%. Bars represent the means±s.e.m of light/heavy-ratios for identified tryptic peptides from both soluble and membrane proteomes. (e) Orthogonal selectivity of inhibitors AA74-1, AA39-2, and AA44-2 illustrated by showing heavy and light MS1 peak pairs for representative tryptic peptides from APEH, PAFAH2, ABHD11, and FAAH. Note that unsubstituted inhibitor AA26-9 nonselectively inhibits all four SHs.
Figure 4:
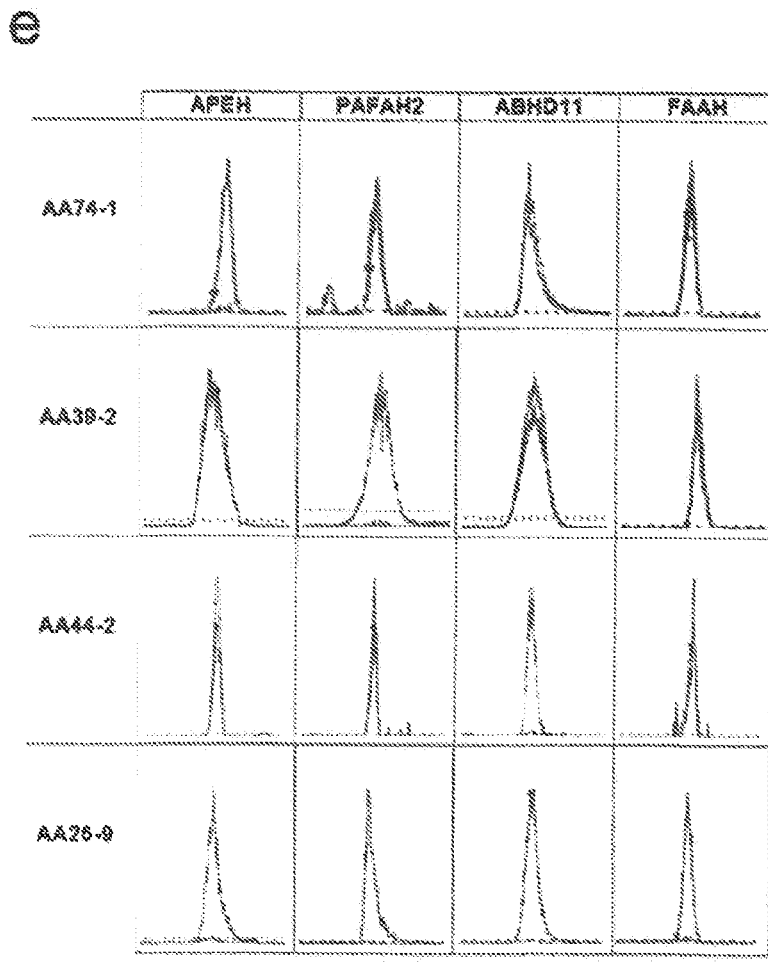

The N2-triazole urea inhibitors, AA74-1, AA39-2, and AA44-2, showed remarkable potency for their respective SH targets in mouse T-cell proteomes, exhibiting respective $IC_{50}$ values of 5, 3, and 1 nM for APEH, PAFAH2, and ABHD11, respectively, in competitive gel-based ABPP assays (FIGS. 4a and b). No other SHs were visibly inactivated by the inhibitors in either soluble or membrane proteome of T-cells at concentrations up to 100 nM (FIG. 4a). The 1,2,3-triazole ureas inhibited recombinant forms of their respective SH targets expressed by transient transfection in COS-7 or HEK-293 cells (FIG. 4c).

N1 regioisomers of AA74-1, AA39-2, and AA44-2 also were evaluated. N1 AA74-1 exhibited an $IC_{50}$ of about 8 nM for APEH; N1 AA39-2 exhibited an $IC_{50}$ of about 6 nM for PAFAH2; and N1 AA44-2 exhibited an $IC_{50}$ of about 58 nM for ABHD11. In addition, the N1 and N2 regioiomers of another triazole urea inhibitor, AA80-1 exhibited $IC_{50}$ values of 11 nM and 5 nM, respectively, for PAFAH2.

Taken together, these data demonstrate that the N1 and N2-carbamoyl-1,2,3-triazole inhibitors of the present invention, many of which can be readily and conveniently prepared using azide/alkyne click chemistry, are potent and selective for a diverse set of SHs.

Example D

SH Inhibition In Vitro

Figure 13:
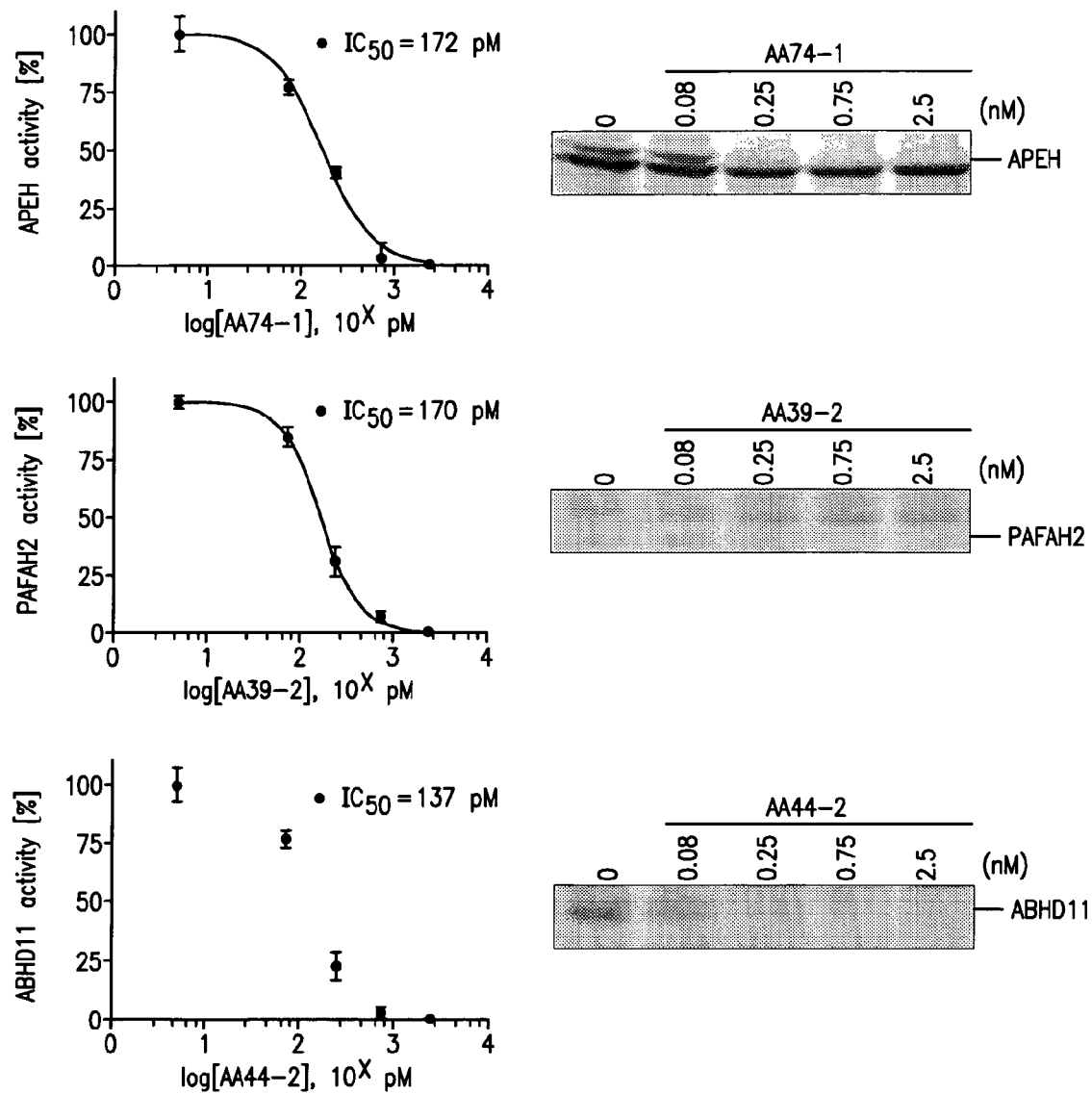
FIG. 13 provides concentration-dependent in situ inhibition curves for AA74-1, AA39-2 and AA44-2 against their respective SH targets. Mouse T-cells were incubated with inhibitor at the indicated concentration or DMSO for 4 h at 37° C., after which cells were homogenized and soluble proteomes isolated and analyzed by gel-based ABPP. Calculated values represent means±s.e.m for three independent experiments.

Mouse T-cells were cultured with different concentrations of inhibitors for 4 h, lysed, and analyzed by competitive ABPP. All three inhibitors (AA74-1, AA39-2, AA44-2) inactivated their respective proteomic targets (APEH, PAFAH2, ABHD11) with exceptional subnanomolar potency (140-170 pM) in vitro (FIG. 13). ABPP-SILAC was then used to assess the selectivity of AA74-1, AA39-2, and AA44-2 in living mouse T-cells (3 nM inhibitor, 4 h). All three inhibitors exhibited remarkable selectivity for their respective SH targets (FIG. 4d). AA74-1 and AA44-2 blocked >95% of APEH and ABHD11 activity, respectively, while not affecting any of the other 40+ SHs detected in T-cells. AA39-2 was similarly effective at blocking its target PAFAH2 in T-cells, and only showed marginal cross-reactivity with a single SH ABHD6, which displayed about 40% reduction in activity. Heavy and light MS1 peak pairs for representative peptides from APEH, PAFAH2, ABHD11, and the untargeted SH FAAH are shown in FIG. 4e to illustrate the orthogonal selectivity of inhibitors AA74-1, AA39-2, and AA44-2. For comparison, the MS1 profiles for T-cells treated with the pan-SH inhibitor AA26-9 are shown, which inactivated all four of the displayed SHs (FIG. 4e).

Example E

Triazole APEH Inhibition In Vivo

Figure 5:
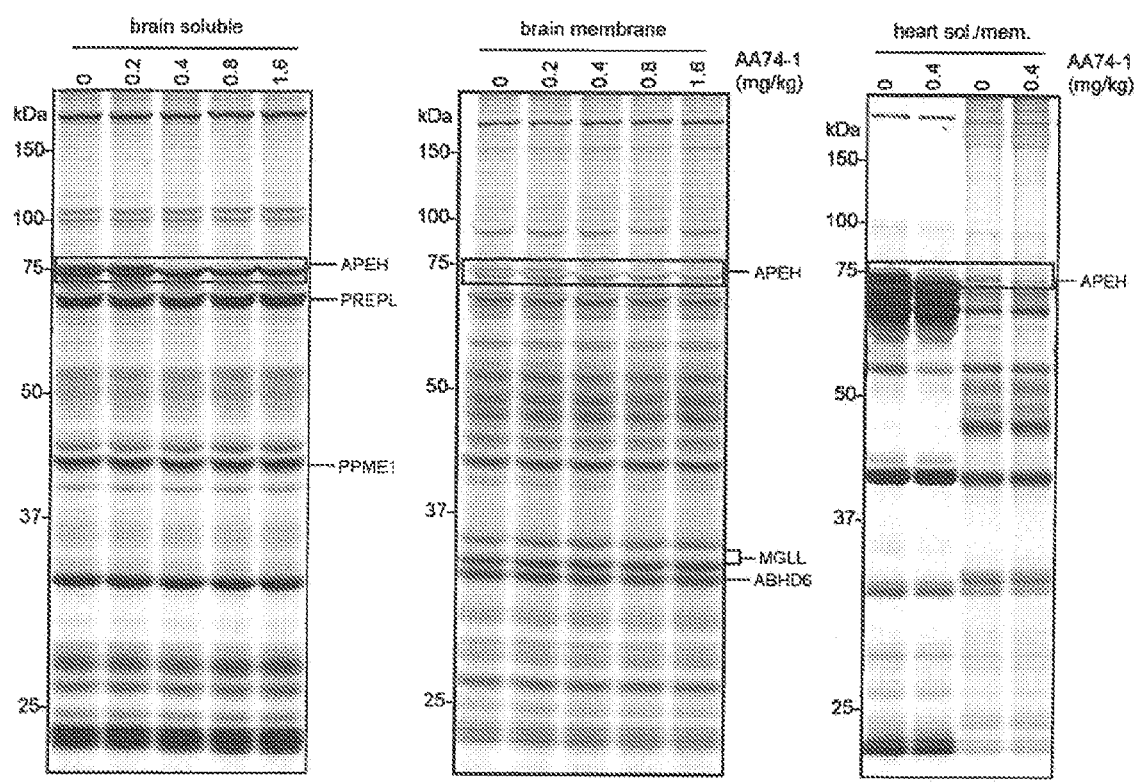
FIG. 5 provides a characterization of the activity and selectivity of APEH inhibitor AA74-1 in vivo. (a) Competitive ABPP results for soluble and membrane proteomes from brain and heart tissue of AA74-1-treated mice. Proteomes were prepared from mice injected with AA74-1 (0.2-1.6 mg/kg, i.p.) or vehicle (PEG300) for 4 h and analyzed by competitive gel-based ABPP. Inhibition of APEH is highlighted with boxes. (b, top) ABPP-SILAM analysis of SH activities in brain tissue from mice treated with AA74-1 (0.8 mg/kg, i.p.) or vehicle (PEG300). Asterisk marks the ratioof-ratio value for APEH, which was inhibited by greater than 97%. Bars represent the means±s.e.m of ratios-of-ratios for observed peptide signals. (b, bottom) Spectral count values for representative SH activities under same experimental conditions. Data are presented as means±s.e.m.
Figure 5:
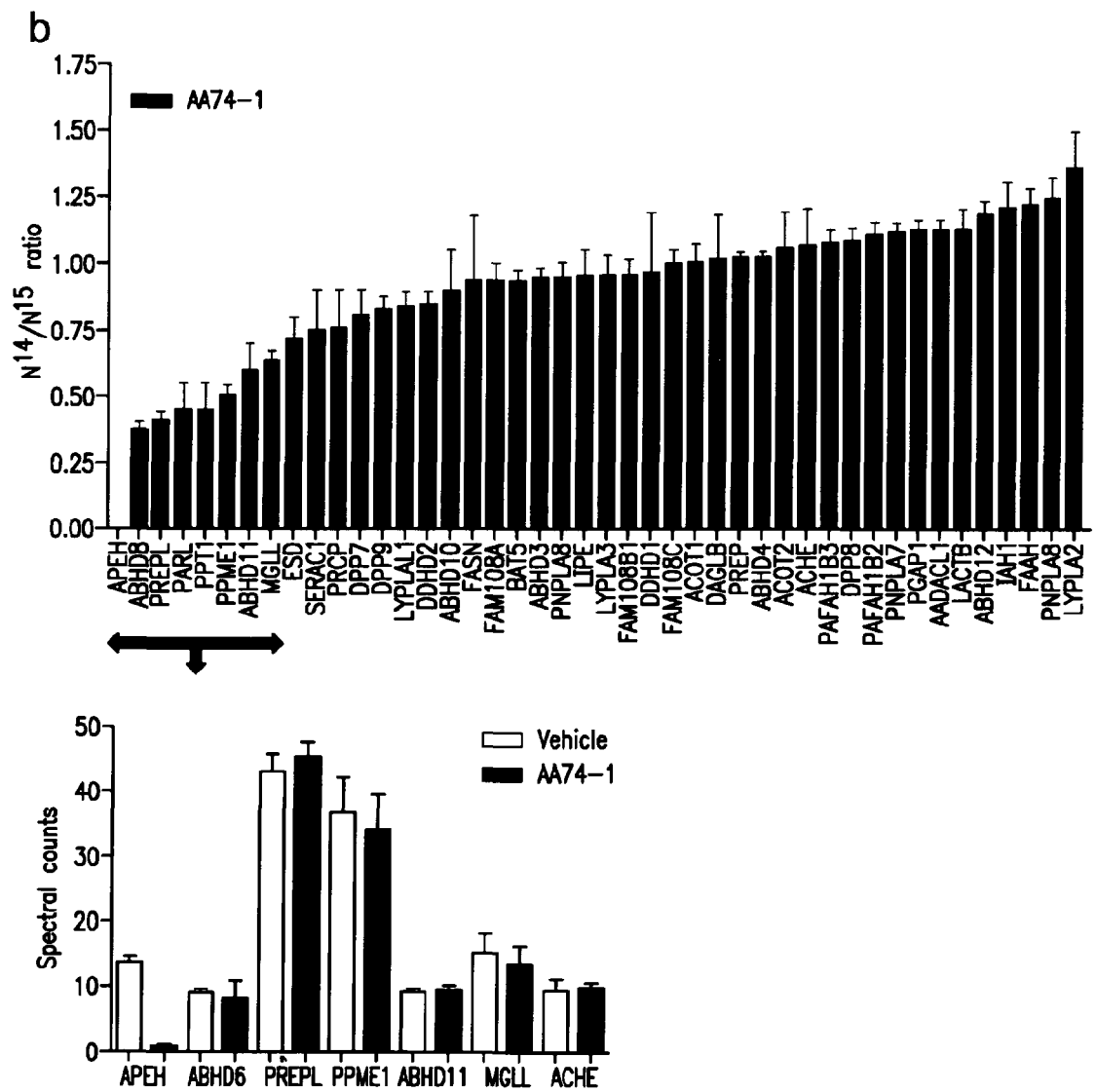
Figures 14, 15:
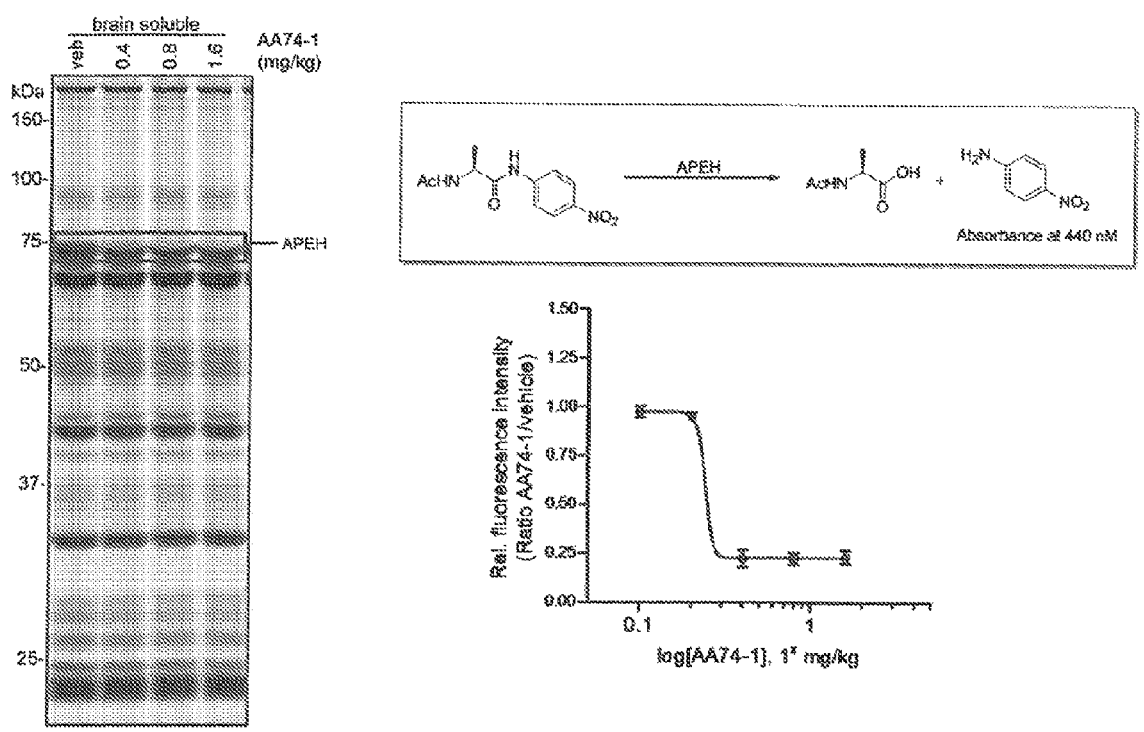
FIG. 14 illustrates selective inhibition of APEH by AA74-1 in vivo. Mice were treated with AA74-1 or vehicle (18:1:1 saline/ethanol/emulphor, i.p.) at the indicated doses for 4 h, sacrificed, and their brain proteomes processed and analyzed by competitive ABPP. Inhibition of APEH is highlighted with boxes.
FIG. 15 provides confirmation of in vivo APEH inhibition in brain by a fluorogenic substrate assay. Soluble brain proteomes from AA74-1 (or vehicle)-treated mice were incubated with N-Acetyl-L-alanine 4-nitroanilide (100 µM) for 2 h at 37° C. and relative absorbance was measured at 440 nM. Calculated values represent means±s.e.m for three independent experiments.
Figure 16:
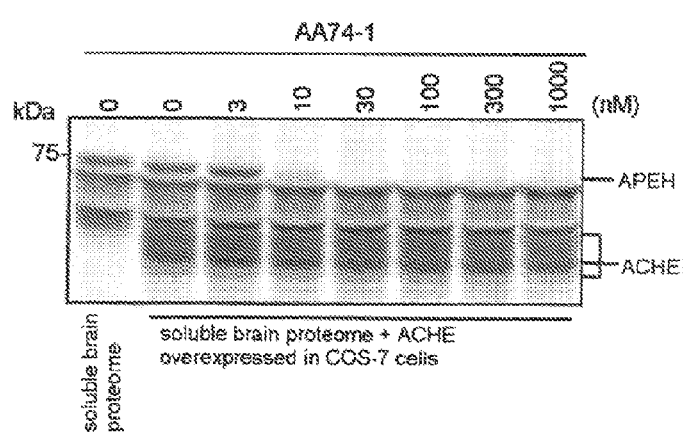
FIG. 16 demonstrates that AA74-1 does not inhibit acetylcholinesterase (ACHE). ACHE was recombinantly expressed in COS-7 cells. Whole cell proteome was mixed 1:1 with soluble mouse brain proteome and treated with DMSO or AA74-1 in vitro at indicated concentrations for 30 minutes at 37° C., after which the samples were analyzed by competitive ABPP. Note that ACHE migrates as multiple bands by SDS-PAGE due to heterogeneous glycosylation. ACHE inhibition in vivo was not observed, as reflected by the equal signals for this enzyme in competitive ABPP results shown in FIG. 5b.

The potency and selectivity of 1,2,3-triazole ureas in vivo also was investigated. Mice were treated with the APEH inhibitor AA74-1 at various doses (0.2-1.6 mg/kg; PEG300 or 18:1:1 saline/ethanol/emulphor intraperitoneally) and sacrificed after 4 h. Brains and hearts were removed, homogenized, and analyzed by gel-based competitive ABPP. AA74-1 completely inhibited APEH in both brain and heart at doses as low as 0.4 mg/kg (equivalent to 10 μg AA74-1 per animal) (FIG. 5a and FIG. 14). Complete inhibition of APEH at this dose was also confirmed by a substrate assay based on cleavage of the fluorogenic probe N-acetyl-L-alanine p-nitroanilide (FIG. 15). No additional SH targets were observed for AA74-1 in either tissue by gel-based ABPP. Finally, the possibility of extending ABPP-SILAC for the characterization of inhibitor selectivity in vivo was explored by taking advantage of recently described protocols for stable isotope labeling in mammals (SILAM). In this approach, brain tissues from vehicle- and AA74-1-treated mice were separately mixed with equivalent amounts of brain tissue from 'heavy' amino acid-fed mice, and the samples were then labeled with FP-biotin, enriched by avidin chromatography, analyzed by LC-MS, and SH activities quantified by measuring the ratio-of-ratios for observed peptide signals. This analysis identified 44 SHs in brain and confirmed that, of these enzymes, only APEH was inhibited by AA74-1 (FIG. 5b). The ratio-of-ratio signals for APEH indicated greater than 90% inhibition of this enzyme in AA74-1-treated animals (FIG. 5b, top), consistent with average spectral count values (14 and 1 spectral counts for APEH in vehicle-treated versus AA74-1-treated mice, respectively; FIG. 5b, bottom). A handful of additional SHs (ABHD6, PREPL) showed ratio-of-ratio signals suggestive of partial inhibition (50-60%); however, these may not represent actual changes, since the spectral count values (FIG. 5b, bottom) and gel-based ABPP signals (FIG. 5a) were not reduced for these enzymes in brain proteomes from AA74-1-treated animals nor were the corresponding enzymes affected in T-cells treated with AA74-1 (see FIG. 4d). ACHE, an enzyme that is targeted by other reported NHU inhibitors, was not inhibited by AA74-1 in either mouse brain (FIG. 5b) or transfected cell (FIG. 16) proteomes.

These findings confirm that AA74-1 acts as an extremely potent and selective inhibitor of APEH in mice and furthermore provide the first example, to our knowledge, of using stable-isotope labeling methods to quantify inhibitor-enzyme interactions in living animals.

Example F

APEH Inhibition

Figure 6:
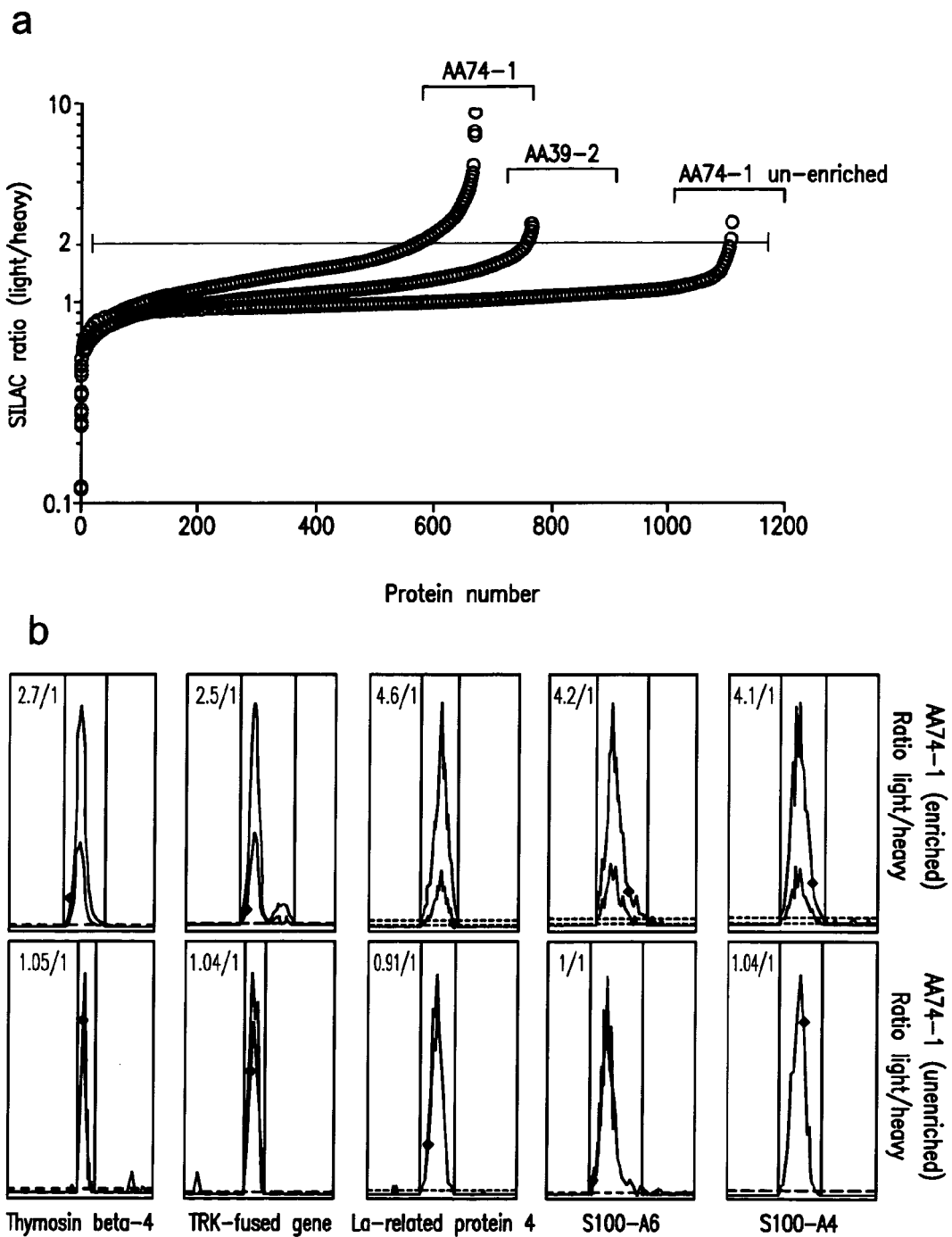
FIG. 6 provides a proteomic characterization of endogenous APEH substrates using N-terminal labeling and enrichment. (a) Measured SILAC ratios for N-terminally enriched and unenriched peptides from the soluble proteome of mouse T-cells treated in situ with AA74-1 or AA39-2. Light gray line designates the two-fold signal change cut-off used to define candidate APEH substrates in AA74-1-treated cells. (b) Heavy and light MS1 peak pairs for five representative N-acetylated proteins after N-terminal labeling and enrichment (top) and for unenriched proteomic samples (bottom) from AA74-1-treated T-cells. Bars represent the means±s.e.m of light/heavy-ratios of identified tryptic peptides in soluble proteomes. (c) In vitro APEH exopeptidase activity assay with synthetic N-acetylated hexapeptides. APEH was recombinantly expressed in HEK-293 cells. Whole cell lysates were pre-treated with DMSO or AA74-1 (3 nM, 30 min), incubated with peptides for 10 h, and release of the N-terminal N-acetylated amino acid was measured by LC-MS. Data are presented as means±s.d. (n=3). Mock corresponds to control cells transfected with an empty vector. (d) Stimulation of mouse T-cell proliferation by APEH inhibition. Mouse T-cells were treated in situ with the indicated inhibitors (1 nM) or DMSO for 12 h. Cell proliferation was measured using the colorimetric agent WST-1 (*p<0.05 for AA74-1- versus AA39-2-treated cells; **p<0.01 for AA74-1-versus AA44-2-treated cells). Data are presented as means±s.d. (n=4).
Figure 17:
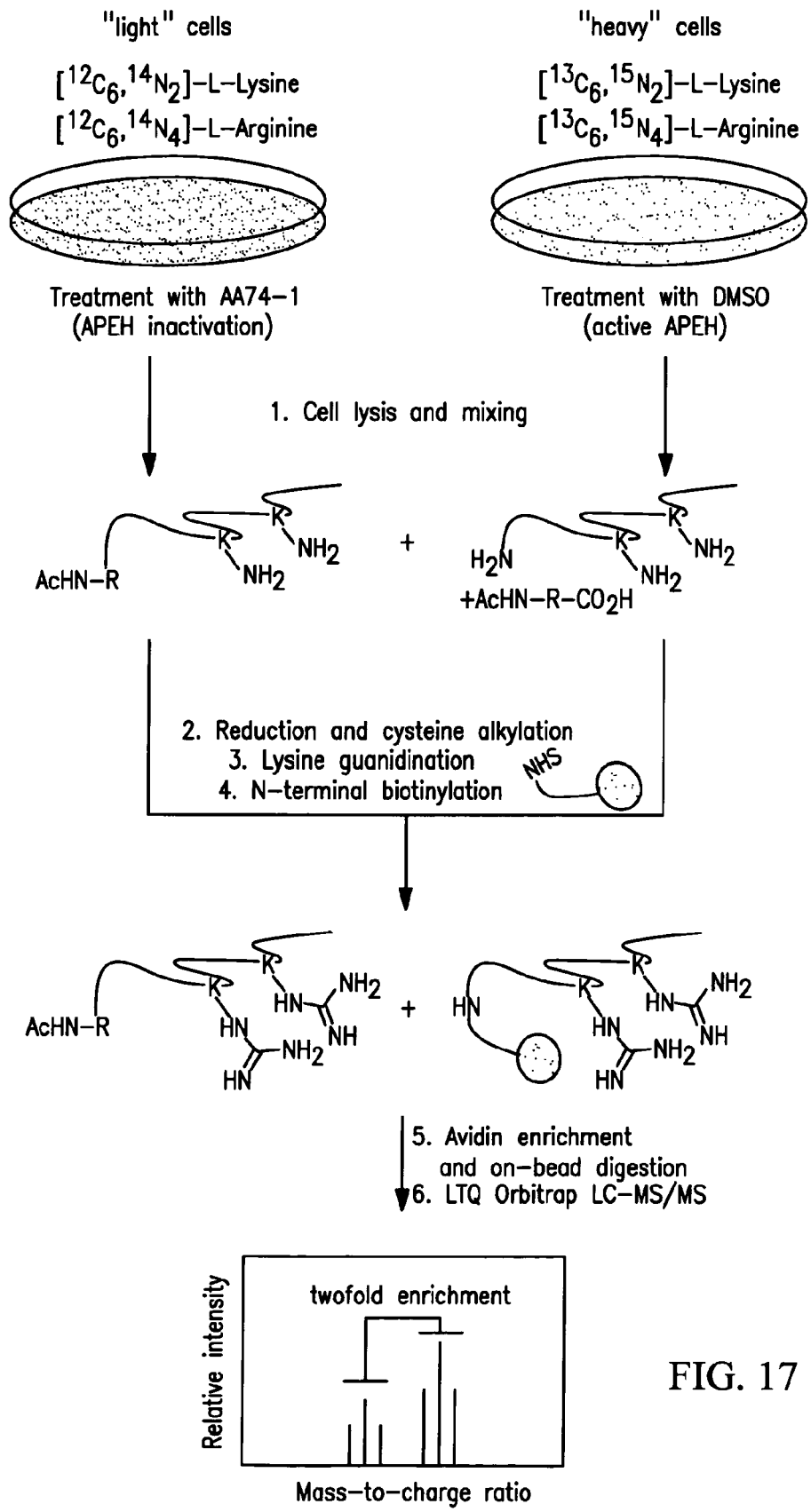
FIG. 17 provides a schematic representation of a SILAC-based N-terminal labeling experiment. Isotopically "light" and "heavy" mouse T-cells were treated with AA74-1 (1 nM) and DMSO, respectively, for 6 h. Cells were lysed and the soluble proteomes were combined in a 1:1 ratio. Lysines were blocked by guadination, and proteins with free N-termini were biotinylated, enriched, trypsinized, and analyzed by LC-MS/MS.

Changes in N-terminally modified proteins in AA74-1 (1 nM) were measured versus DMSO-treated T-cells by SILAC combined with an established method for selective biotinylation of N-terminal amines (FIG. 17). Biotinylated proteins were enriched by avidin chromatography, digested on-bead with trypsin, and the resulting peptides analyzed by LC-MS on an LTQ-Orbitrap instrument. Data sets were filtered to identify proteins with multiple peptides that showed consistent two-fold or greater reductions in signals in AA74-1-treated cells. The resulting collection of 25 proteins represented candidate APEH substrates (FIG. 6a and FIG. 7). Importantly, none of these proteins showed altered N-terminal labeling profiles in T-cells treated with the PAFAH2 inhibitor AA39-2 (FIG. 7), which produced a negligible number of total changes in the N-terminally modified protein profile (FIG. 6a). Comparisons to previous proteomic studies revealed that about half of the APEH-regulated proteins have been confirmed to possess acetylated N-termini (FIG. 7). Five of these N-terminally acetylated proteins, were selected, which showed 2.5 to 4.6-fold changes in N-terminal labeling signals following AA74-1 treatment (FIG. 6b), for further characterization. Hexameric peptides that match the N-terminally acetylated sequences for each protein were synthesized and tested as direct substrates with recombinantly expressed APEH. In each case, APEH-transfected cells were found to cleave the N-terminally acetylated residue to a much greater extent than mock-transfected cells and this cleavage was blocked by AA74-1 (FIG. 6c). These data thus provide the first global portrait of endogenous substrates for APEH and suggest that this enzyme plays a broad role in regulating the basal N-terminal acetylation state for many proteins in the proteome.

AA74-1 also causes a significant increase in cellular proliferation (FIG. 6d). This stimulatory effect was not observed with triazole ureas targeting ABHD11 (AA44-2) or PAFAH2 (AA39-2) (FIG. 6d), supporting that it is a specific consequence of APEH blockade and may be related to changes in the enzyme's N-acetylated substrates.

Figure 18:
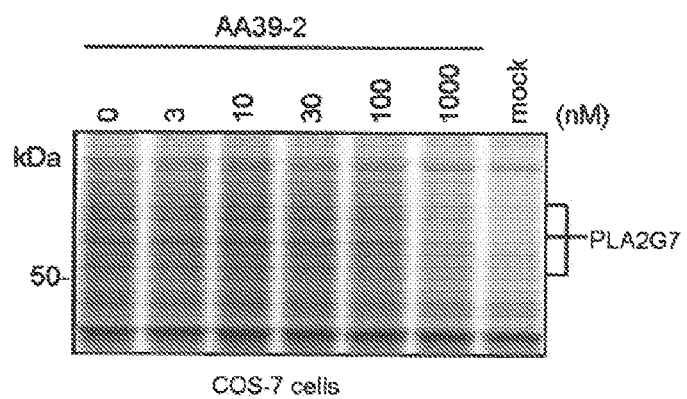
FIG. 18 demonstrates selectivity of AA39-2 for PAFAH2 over its nearest sequence-neighbor PLA2G7. PLA2G7 was recombinantly expressed in COS-7 cells and treated with DMSO or AA39-2 in vitro at indicated concentrations for 30 minutes at 37° C., after which the samples were analyzed by competitive ABPP.

PAFAH2 and APEH are selectively inhibited over their nearest sequence-neighbor enzymes PLA2G7 (AA39-2: $IC_{50}$ for PAFAH2=3 nM; $IC_{50}$ for PLA2G7=100 nM; FIG. 18) and the dipeptidylpeptidases (e.g., DPP4, DPP8, DPP9; FIG. 4d), respectively.

Figure 19:
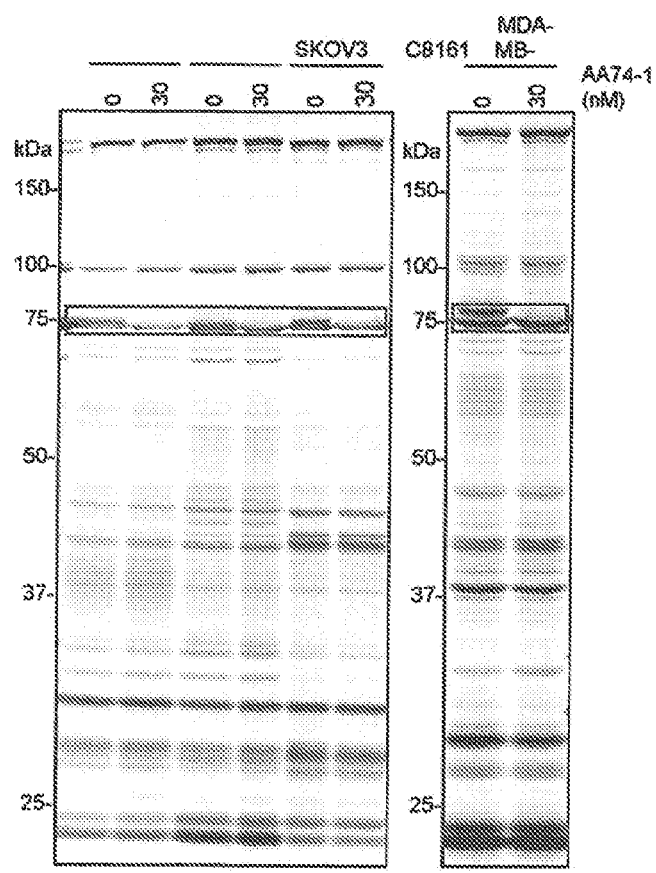
FIG. 19 demonstrates that AA74-1 potently and selectively inhibits human and rat orthologs of APEH. The soluble fractions of human ovarian (SKOV3), melanoma (C8161), and breast (MDA-MB-231) cancer cells, as well as rat neuroblastoma (B103) cells were treated with 30 nM AA74-1 or DMSO for 30 minutes at 37° C., after which the samples were analyzed by competitive ABPP. Inhibited APEH is highlighted with boxes. Note that other SHs detected in human and mouse proteomes were not inhibited by AA74-1.

The remarkable 'ultrapotency' displayed by optimized 1,2,3-triazole ureas in living systems (sub-nM $IC_{50}$ values in cells, sub-1 mg/kg efficacy in mice) suggests that these compounds are readily taken up by cells and not susceptible to rapid metabolism. These results reflect a constitutive role for APEH in regulating the stability of this modification. Consistent with this premise, APEH can cleave the N-terminally acetylated amino acid from hexapeptide sequences matching the N-termini for five of the altered proteins. Additional pieces of evidence supporting that the N-terminal labeling changes were due to specific inhibition of APEH by AA74-1 include: (1) treatment with the structurally related PAFAH2-selective inhibitor AA39-1 did not produce these changes (FIG. 6a), and (2) changes were not observed in total protein abundance for the subset of APEH substrates that could also be detected in unenriched proteomic profiles from AA74-1-treated cells (FIG. 6b and FIG. 7). The proteomic changes caused by AA74-1 were accompanied by a significant increase in T-cell proliferation. Although the mechanism underlying the pro-proliferative effect of APEH inhibition is not fully understood, some of the identified substrates for this enzyme, such as the S100A proteins, have been suggested to promote cellular proliferation, and it is possible that changes in N-acetylation may impact their biological activity. The pro-proliferative effect of APEH inhibition is also noteworthy when considering that the APEH gene is deleted in certain cancers, where it has been proposed to serve as a potential tumor suppressor. AA74-1 which potently inhibits not only mouse APEH ($IC_{50}$=3 nM), but also the human ($IC_{50}$=11 nM) and rat ($IC_{50}$=7 nM) orthologs of this enzyme (FIG. 19).

Example G

Diacylglycerol Lipase Inhibition

Compounds KT109 and KT172 (FIG. 21), are potent and highly selective for DAGLB. These compounds demonstrate remarkable activity in both living cells and animal models. To directly profile endogenous DAGLB activity in cells and tissues, a DAGL-tailored activity-based probe, referred to herein as HT01 (FIG. 21), which labels DAGLB with high specificity in complex proteomes. Using these agents and Daglb$^{-/-}$ mice, DAGLB is shown herein to be the principal 2-AG biosynthetic enzyme in peritoneal macrophages. Acute inactivation of DAGLB results in decreased 2-AG and decreased arachidonic acid levels, as well as a subsequent accumulation of endogenous diglyceride substrates. In parallel with the arachidonic acid changes, DAGLB inhibition lowers prostaglandin levels in a manner that is distinct and complementary to cytosolic phospholipase-A2 (cPLA2). The metabolic disruptions from DAGLB inactivation result in reduced levels of lipopolysaccharide-stimulated TNF-alpha release and points to a novel role for DAGLB in regulating an endocannabinoid-eicosanoid network, which drives the proinflammatory response in macrophages.

Example H

Triazole-Urea DAGLB Inhibitors

A gel-based ABPP assay described herein was optimized for screening against recombinant DAGLB. In brief, fluorophosphonate (FP)-rhodamine is inactive against DAGLA, but a concentration-dependent inhibition of DAGLB was observed using FP-rhodamine, with maximal inhibition of enzyme activity occurring at approximately 5 μM, using a LC-MS substrate assay. Using HEK293T-DAGLB-overexpressed lysates and optimal probe concentrations (about 5 μM FP-rhodamine), activity-dependent fluorescent labeling of DAGLB was observed, which could be blocked by the non-specific lipase inhibitor, THL in a dose-dependent manner.

Figure 22:
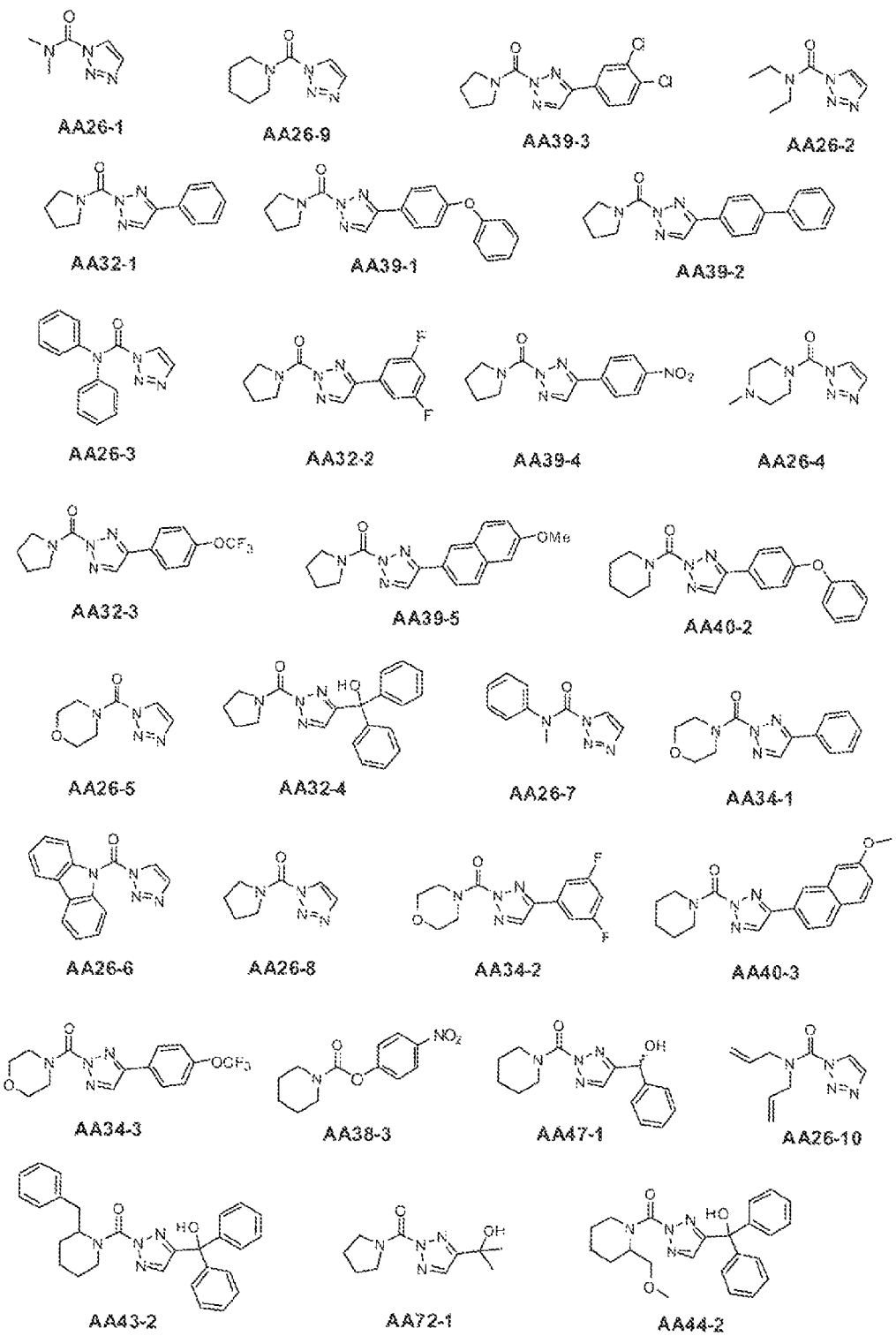
FIG. 22 provides structures of substituted 1,2,3-triazole ureas used for initial DAGL inhibition screening.

Using this newly optimized activity assay for DAGLB, a structurally diverse library (FIG. 22) of 1,2,3-triazole ureas was investigated. From this library, a single active compound, referred to herein a AA43-2 (FIG. 21) was identified, which completely blocked probe-labeling of DAGLB. AA43-2 displayed modest activity against recombinant DAGLB ($IC_{50}$ approximately 200 nM) but also showed off-target activity against several other serine hydrolases, notably ABHD6, KIAA1363, and LYPLA1/2 at higher concentrations in the mouse brain proteome Compound KT117, described herein, is a triazole urea containing a 2-benzylpiperidyl substituent like AA43-2. The activity of the 1,4-regioisomer (KT116, FIG. 21) of compound KT117 (originally purified as the 2,4-regioisomer) was evaluated to determine if one isomer was more active against DAGLB, than the other isomer. In fact, KT116 was greater than 5-fold more potent against DAGLB than KT117. Interestingly, the regioselectivity of this scaffold also changed the selectivity profiles of the respective isomers in the mouse brain proteome.

Replacement of the bromo-phenyl substituent of KT116 with a trifluoromethoxy-phenyl group afforded a compound referred to herein as KLH25 (FIG. 21), which exhibited activity against both DAGL enzymes (i.e., DAGLA and DAGLB) and was significantly more potent against DAGLB in comparison to AA43-2. In addition to significant improvements in potency, negligible activity against LYPLA1, LYPLA2, and PAFAH2, known targets of the triazole urea chemotype, was observed. To assess the degree to which KLH25 is active in vivo, mice were treated with the compound for about 4 hours (25 mg/kg in PEG300, administered intraperitoneally, i.p.), sacrificed, and tissues were harvested for ABPP analysis. Potent inhibition of ABHD6 and FAAH was observed, demonstrating that the 2-benzylpiperidyl triazole ureas are a significant new class of serine protease inhibitors. No inhibition of protein bands corresponding to endogenous DAGLA or DAGLB was observed. Compound KT109, which includes a diphenyl-substituted triazole leaving group (FIG. 21), exhibited improved selectivity against FAAH, MGLL, and ABHD11, while maintaining comparable potencies against DAGLB measured using both competitive ABPP and LC-MS substrate assays.

Modifying the distal phenyl-substituent of the triazole ring with an ortho-methoxy group resulted in compound KT172 (FIG. 21). KT172 was selective against PLA2G7, showing mild activity against this off-target enzyme at higher concentrations, while maintaining potency against DAGLB. The improved selectivity of KT172 against PLA2G7 also resulted in slightly increased activity against MGLL, demonstrating that KT109 and KT172, when used in parallel, serve as complementary inhibitors to help control potential off-target activities from each respective compound.

In order to further tune the selectivity of KT109 and KT172 and remove ABHD6 off-target activity, an ABHD6-selective inhibitor was prepared to serve as a control probe for biological studies. In brief, replacement of the 2-benzyl group on the piperidyl ring with a 2-phenyl substituent and changing the position of the methoxy substituent on the distal phenyl of the triazole group afforded compound KT195 (FIG. 21). KT195 completely inactivated ABHD6 at concentrations equivalent to those seen for DAGLB by KT109 and KT172. Unlike the DAGLB probes, KT195 showed negligible activity against DAGLA at micromolar concentrations while maintaining a selectivity profile comparable to KT109 and KT172. The structure of KT195 was confirmed using a combination of X-ray crystallography and $^1$H-NMR.

To detect endogenous DAGLB activity in cellular and in vivo experiments, a fluorescently-tagged version of KLH25, HT01 (FIG. 21), was prepared. In brief, opening the piperidyl-ring of KLH25 did not drastically change the potency and selectivity of the compound. A boron-dipyrromethene (BODIPY) dye was appended for fluorescence detection. HT01 was active against both recombinant DAGLA and DAGLB, and approximately 5-fold more active against DAGLB than FP-rhodamine. HT01 was used to profile the activity of 2-substituted piperidyl 1,2,3-triazole urea DAGLB inhibitors against DAGLA. It was found that KT172 was more potent against the alpha isoform in comparison with KT109.

The specificity of HT01 for endogenous DAGLB was assessed by measuring DAGLB activity in genetic knockout mice. Daglb$^{-/-}$ mice were generated by gene-trapping. Daglb$^{+/+}$, Daglb$^{+/-}$, and Daglb$^{-/-}$ mice were identified by PCR genotyping of genomic tail DNA. Mouse brain and peritoneal macrophage proteomes were profiled using both HT01 and FP-rhodamine. Labeling of an approximately 70 kDa band in Dagl$^{+/+}$ mice, was observed, which was absent in Dag/b$^{-/-}$ mice in both proteomes using the HT01 probe. In both proteomes, pretreatment with KT172 (2 μM) resulted in significantly reduced probe labeling (>80%) of the DAGLB band. Interestingly, the activity profiles showed dramatically higher levels of active DAGLB in macrophages compared with the brain proteome. These results confirm the reported gene expression profiles of DAGLB, which show nearly 10-fold higher expression levels in macrophages compared with other tissues. Neuro2A neuroblastoma cells express moderate levels of active DAGLB.

Other probes useful in assessing DAGL selectivity include HT02 (an alkynylated probe), and HT03 (a biotinylated probe. The structures of HT02 and HT03 are shown in FIG. 21.

To assess how effectively the DAGLB inhibitors maintain their potency and selectivity in living cells, Neuro2A cells were cultured with different concentrations of inhibitors for 4 hours, lysed, and then analyzed by competitive ABPP. Both DAGLB inhibitors (KT109 and KT172) completely inactivated DAGLB with nanomolar potency ($IC_{50}$ values of 14 and 11 nM, respectively). In contrast, the ABHD6-control probe, KT195 showed negligible activity against DAGLB while completely inactivating ABHD6 at the same dose used for inactivation of DAGLB by KT109 and KT172. An LC-MS-based method, ABPP-SILAC was used to provide a more comprehensive profile of serine hydrolase activities in proteomes. Cells were treated for about 4 hours with optimal concentrations of each compound (25 nM for KT172 and KT195; 50 nM for KT109). Each inhibitor showed exceptional selectivity for their respective targets by SILAC-ABP. Both KT109 and KT172 blocked approximately 90% of DAGLB activity with negligible activity against any other serine hydrolases detected in the Neuro2A proteome with the exception of ABHD6. KT195 blocked ABHD6 activity by >90% with no activity against other serine hydrolase detected in the Neuro2A proteome, including DAGLB.

Figure 23:
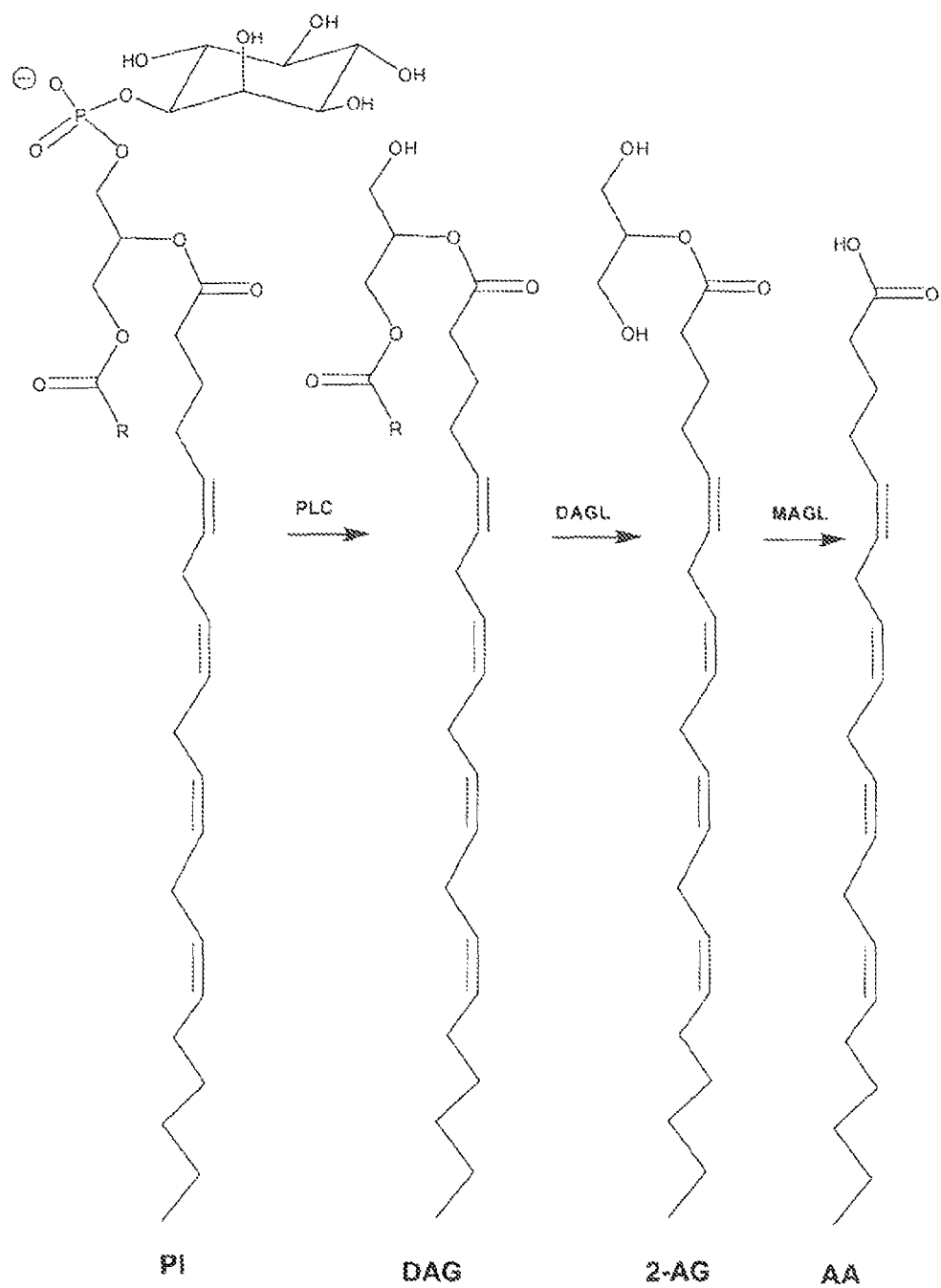
FIG. 23 illustrates biochemical transformations of arachidonate-containing diglycerides catalyzed by phospholipase C (PLC), diacylglycerol lipase (DAGL) and monoacylglycerol lipase (MAGL).

A metabolomic analysis of Neuro2A cells treated with the DAGLB inhibitors and ABHD6 control probe. The current paradigm designates DAGL enzymes as the key biosynthetic enzymes catalyzing the hydrolysis of arachidonate-containing diglycerides to generate 2-AG (FIG. 23). After treating cells for 4 hours, a significant decrease in cellular 2-AG levels (approximately 90%) was observed compared with untreated or KT195 treated cells. Interestingly, a significant accumulation of the stearoyl-arachidonoyl diglyceride (SAG) was observed. To investigate this further, the levels of several diglycerides containing an arachidonoyl-group at the sn-2 position were compared, with varying acyl chains at the sn-1 position. The results revealed that DAGLB prefers diglyceride substrates with long-chain saturated/monounsaturated acyl chains at the sn-1 position as judged by greater accumulation of the C18:0 and C18:1 arachidonyl-containing DAGs in comparison with the C14:0 and C16:0 arachidonyl-containing DAGs. It is believed that these studies represent the first reported identification of endogenous DAGLB substrates. Finally, inactivation of DAGLB results in approximately 50% decreases in arachidonic acid (AA), confirming the reported AA changes seen in DAGL knockout mice.

Example I

DAGLB Inactivation in Peritoneal Macrophages In Vivo

To investigate the in vivo functions of DAGLB, the activity of 2-SPTU compounds in peritoneal macrophages was profiled based on expression/activity levels from studies described above. Mice were treated with KT109, KT172, or KT195 at various doses (about 10 to about 0.1 mg/kg in 18:1:1 saline/ethanol/emulphor (a polyethoxylated vegetable oil), administered i.p.) and sacrificed after about 4 hours. Thioglycolate-elicited peritoneal macrophages were harvested, lysed, and analyzed by gel-based competitive ABPP using HT01. Both KT172 and KT109 completely inactivated DAGLB at doses as low as 0.5 mg/kg. In contrast, control probe KT195 showed no activity against DAGLB up to 10 mg/kg of compound. To determine the in vivo kinetics of DAGLB inhibition, mice were administered KT109, KT172, or KT195 (5 mg/kg, i.p.), sacrificed at various time points (about 1 to 16 hours after administration), and thioglycolate-elicited peritoneal macrophages harvested and subjected to gel-based ABPP. Inhibition of DAGLB by both KT109 and KT172 was rapid, with complete inhibition achieved within the first hour. In contrast, the duration of inhibition for KT172 was shorter compared with KT109. The latter compound showed persistent inhibition (approximately 90%) of DAGLB even after 16 hours. KT195 showed no evidence of DAGLB inhibition during the entire time-course of treatment.

Selectivity profiles from gel-based ABPP experiments show that the DAGLB inhibitors and the ABHD6-control probe maintain good selectivity at doses where complete inactivation of the respective targets is achieved. To gain a more comprehensive in vivo profile of inhibitor selectivity, ABPP-MudPIT was utilized to measure enzyme activity levels by spectral counting. These analyses identified >31 serine hydrolases in the peritoneal macrophage proteome and confirmed inhibition of DAGLB by both KT172 and KT109. In contrast, KT195 treatment resulted in complete inhibition of ABHD6 with no activity against DAGLB. Several off-target activities for KT109 and KT172 were observed, including carboxylesterases (Ces3 and Ces2g), which are common peripheral targets using mechanism-based inhibitors. However, these same off-targets are also inhibited by KT195, allowing identification of potential non-specific effects in the in vivo studies by simply comparing KT109/172 versus KT195-mediated effects. Pla2g15 also was identified as an off-target using the DAGLB inhibitors. However, it is believed that the reduced signals seen in the MudPIT analysis are not activity-dependent based on (1) the fact that this enzyme is a secreted phospholipase found in plasma (2) differences in the in vitro selectivity profiles of compounds against recombinant Pla2g15 are not recapitulated in vivo. Nonetheless, a similar decrease in Pla2g15 signals was observed in KT195-treated macrophages, once again providing a means to identify off-target effects using the control probe.

Example J

DAGLB Regulates an Endocannabinoid-Eicosanoid Proinflammatory Network in Peritoneal Macrophages Mice were treated with KT109, KT172 or KT195 (5 mg/kg, 4 hours, i.p.) to evaluate whether blockade of DAGLB in peritoneal macrophages would result in metabolic effects similar to those observed in Neuro2A cells. Thioglycolate-elicited peritoneal macrophages were harvested, and the cells were subjected to metabolomics studies. Dramatic decreases in 2-AG were observed in both KT172-treated and KT109-treated mice, while no observable changes were evident in mice treated with the KT195 control probe. Concurrent with the decreased 2-AG, were significant increases in SAG in the KT172-treated and KT109-treated mice, but not in the KT195-treated mice, confirming that this diglyceride (i.e., 2-AG) is an endogenous substrate in cells and in vivo. Surprisingly, significant decreases in cellular AA levels and a corresponding reduction in $PGE_2$ and $PGD_2$ (two AA-derived eicosanoids) were observed. None of these effects were observed in KT195-treated mice. All the metabolic effects observed in pharmacological studies were recapitulated using $Daglb^{-/-}$ mice, providing genetic evidence that the changes were indeed DAGLB-mediated.

Given the numerous reports demonstrating a dominant role for Pla2g4a (cPLA2) in regulating the bulk of AA-derived eicosanoids, there was an interest in comparing AA and eicosanoid levels in cPLA2 knockout mice in the presence and absence of the DAGLB inhibitors described herein. $Pla2g4a^{-/-}$ mice were treated with KT109 or KT195 (5 mg/kg, 4 hours, i.p.), thioglycolate-elicited macrophages were harvested, and then the macrophages were subjected to metabolomics analysis. The cellular levels of $PGE_2$ and $PGD_2$ were measured. While $Pla2g4a^{-/-}$ mice showed no detectable levels of $PGD_2$, $PGE_2$ was detectable albeit at lower levels. Unexpectedly, treatment with the DAGLB inhibitor (KT109) resulted in a significant decrease in $PGE_2$, an effect that was not observed in $Pla2g4a^{-/-}$ mice treated with the control probe, KT195. $PGD_2$ remained undetectable in the KT109-treated and KT195-treated $Pla2g4a^{-/-}$ mice.

The effects of DAGLB-inhibition on the proinflammatory response in $Pla2g4a^{+/+}$ versus $Pla2g4a^{-/-}$ mice also was evaluated. Thioglycolate-elicited macrophages from C57 BL/6 mice treated with KT109 or KT195 (5 mg/kg, 4 hours, i.p.) were harvested, plated, and stimulated with lipopolysaccharide (LPS). Compared with non-stimulated macrophages, dramatically increased levels of TNF-alpha were observed upon stimulation with LPS (5 μg/mL, 90 min) as measured using ELISA. Macrophages from mice treated with KT109, but not KT195, showed a modest but significant reduction in secreted TNF-alpha levels, and this pharmacological suppression in the cytokine response was validated in genetic knockout models.

Next, the cytokine profiles from a Pla2g4a$^{+/+}$ background were compared with the profiles from Pla2g4a$^{-/-}$ mice treated with KT109 or KT195 (5 mg/kg, 4 hours, i.p.). Peritoneal macrophages from both Pla2g4a$^{+/+}$ and Pla2g4a$^{-/-}$ displayed robust secretion of TNF-alpha upon stimulation with LPS. However, no significant differences in LPS-stimulated TNF-alpha levels were observed from Pla2g4a$^{+/+}$ versus Pla2g4a$^{-/}$ mice$^-$. In sharp contrast, peritoneal macrophages from KT109-treated Pla2g4a$^{-/-}$ mice showed significantly higher TNF-alpha levels (2-fold) upon LPS stimulation, while no observable effects were observed from Pla2g4a$^{-/-}$ mice treated with the control-probe KT195 The enhanced secretion of TNF-alpha is similar to effects seen with COX inhibitors and suggests that DAGLB and cPLA2 play distinct and complementary roles in the proinflammatory response of peritoneal macrophages by regulating AA-derived PGE$_2$ pools involved in suppressing TNF-alpha release.

Example 1

Evaluation and Test Methods

Ex. 1(A)

Gel-Based ABPP of Cell and Tissue Proteomes with FP Probes

Gel-based ABPP experiments were performed using previously established methods known in the art.

Ex. 1(B)

Competitive ABPP-SILAC

Isotopically "light" and "heavy" BW5147-derived murine T-cell hybridoma cells mouse T-cells were cultured with inhibitor and DMSO, respectively, for 4 h. Cells were lysed, proteomes were adjusted to a final protein concentration of 1.0 mg/mL and were labeled with 7 μM of FP-biotin (500 μL total reaction volume) for 1.5 hr at 25° C. After incubation, heavy and light proteomes were mixed in an approximate 1:1 ratio. The proteomes were desalted with PD-10 desalting columns (Amersham Biosciences) and FP-labeled proteins were enriched with avidin beads. The beads were washed with 1% SDS in PBS, PBS, and H$_2$O, then resuspended in 6M urea, reduced with DTT, and alkylated with iodoacetamide. On-bead digestions were performed for 12 h at about 37° C. with trypsin (Promega) in the presence of 2 mM CaCl$_2$. Peptide samples were acidified to a final concentration of 5% formic acid, pressure-loaded on to a biphasic (strong cation exchange/reverse phase) capillary column and analyzed by two-dimensional liquid chromatography (2D-LC) separation in combination with tandem mass spectrometry using an Agilent 1100-series quaternary pump and Thermo Scientific LTQ Orbitrap ion trap mass spectrometer.

Ex. 1(C)

Fluorogenic APEH Activity Assay

APEH activity assay was performed using fluorogenic substrate N-Acetyl-L-alanine p-nitroanilide.

Ex. 1(D)

APEH Activity Assay with Synthetic N-Acetylated Hexapeptides

Enzyme assays were performed with LC-MS by monitoring the release of the N-terminal N-acetyl amino acid. APEH was transiently overexpressed in HEK-293 cells and whole cell lysates were treated with DMSO or 3 nM AA74-1 for 30 minutes and adjusted to a final protein concentration of about 0.3 mg/mL with PBS buffer. For each reaction, about 200 μM of hexapeptide were incubated with lysates for 10 h at 37° C. before quenching with 0.8 mL MeOH. Samples were centrifuged for 10 minutes at 10,000×g at 4° C. and the supernatant was dried down under vacuum. For LC-MS analysis samples were injected into an Agilent 1100 LC-MSD SL instrument applying the following gradient: Buffer A (MeCN) to Buffer B (95:5 H$_2$O/MeCN+50 mM NH$_4$OAc+0.2% NH$_4$OH). Data represent the average±s.d. for three experiments.

Ex. 1(E)

Materials

FP-biotin and FP-rhodamine were synthesized following previously described protocol. Full-length cDNAs encoding SHs were purchased from Open Biosystems. Synthetic N-acetylated hexapeptides were purchased from Biopeptide Co.

Ex. 1(F)

Recombinant Expression in COS-7 or HEK-293 Cells

Briefly, full-length cDNAs encoding mouse serine hydrolases were either transfected directly (if available in a eukaryotic expression vector) or subcloned into pcDNA3 (Invitrogen). COS-7 or HEK-293 cells were grown to about 70% confluence in 10 cm dishes in complete medium (DMEM with L-glutamine, nonessential amino acids, sodium pyruvate, and FCS) at 37° C. and 5% CO$_2$. The cells were transiently transfected by using the appropriate cDNA or empty vector control ("mock") and the FUGENE® 6 (Roche Applied Science) transfection reagents following the manufacturers' protocols. After 48 hrs, the cells were washed twice with phosphate-buffered saline (PBS), and collected by scraping.

Ex. 1(G)

In Situ Treatment of Mouse T-Cells with Inhibitors

BW5147-derived murine T-cell hybridoma cells were grown in RPMI-1640 medium (Cellgro) with 10% FCS and 1× Penicllin, Streptomycin, Glutamine solution (Invitrogen) at 37° C. and 5% CO$_2$. 15 cm dishes with T-cells (10$^6$ cells/mL) were treated with inhibitors for indicated amount of time. Cells were peletted by centrifugation, washed twice with PBS, and lysed in PBS buffer by sonication.

Ex. 1(H)

In Vivo Studies with AA74-1

AA74-1 was prepared as a saline-emulphor emulsion by vortexing, sonicating, and gently heating neat compound directly into an 18:1:1 v/v/v solution of saline:ethanol:emulphor, or as a homogeneous PEG solution by vortexing and sonicating neat compound directly into PEG300 (Fluka).

Mice (<6 months old, 20-28 g) were i.p. administered AA74-1 or an 18:1:1 v/v/v saline:emulphor:ethanol vehicle at a volume of 10 μL/g weight or a PEG vehicle at a volume of 4 μL/g weight. After 4 h, mice were sacrificed, and tissues were removed and flash frozen in liquid $N_2$.

Ex. 1(I)

Preparation of Mouse Tissue and Cell Line Proteomes

The soluble and membrane fractions from mouse tissues and cell lines were generated following previously described methods. Briefly, mouse tissues were Dounce-homogenized in PBS (pH 7.5) followed by a low-speed spin (1,400×g, 5 min) to remove debris. The supernatant was then subjected to centrifugation (64,000×g, 45 min) to provide the soluble proteome as the supernatant and the membrane proteome as the pellet. The pellet was washed twice with PBS and resuspended in PBS buffer by sonication.

Cellular proteomes were isolated using standard procedures. Briefly, cell pellets were sonicated in PBS and centrifuged (64,000×g, 45 min) to provide the soluble fraction as the supernatant and the membrane fraction as the pellet. The pellet was resuspended in PBS by sonication. Total protein concentration of each fraction was determined using a protein assay kit (Bio-Rad). Samples were stored at −80° C. until use.

Ex. 1(J)

Gel-Based Competitive ABPP

Gel-based competitive ABPP experiments were performed as described previously. For competitive ABPP with FP-rhodamine, proteomes (1 mg/mL in PBS) were treated with FP-rhodamine (2 μM final concentration) in a 50 mL total reaction volume. After 30 minutes at 25° C., the reactions were quenched with 2×SDS-PAGE loading buffer.

For ABPP experiments with alkyne-containing probes rhodamine azide (12.5 μM final concentration) was added, followed by TCEP (0.5 mM final concentration) and ligand (100 μM final concentration). Samples were gently vortexed and the cycloaddition initiated by the addition of $CuSO_4$ (1 mM final concentration). The reactions were incubated at room temperature for 1 h and quenched with 2×SDS-PAGE loading buffer.

After separation by SDS-PAGE (10% acrylamide), samples were visualized in-gel with a flatbed fluorescence scanner (Hitachi FMBio IIe).

Ex. 1(K)

Gel-Based Competitive ABPP with FP-Biotin and Alkyne Probes AA6-10

Mouse brain membrane proteomes were incubated with FP-biotin (20 μM final concentration) for 30 minutes at 37° C., followed by addition of alkyne probes (20 μM final concentration) and incubation for further 30 minutes at 37° C.

Ex. 1(L)

Determination of $IC_{50}$ Values by Gel-Based Competitive ABPP

Proteomes were incubated with inhibitors for 30 minutes at 37° C. (in vitro) or for 4 h at 37° C. (in situ) at the indicated concentrations (n=3) prior to FP-rhodamine labeling. After SDS-PAGE and in-gel visualization, the percentage enzymatic activity remaining was determined by measuring the integrated optical intensity of the bands using IMAGER® software. $IC_{50}$ values were determined from a dose-response curve generated using PRISM® software (GraphPad).

Ex. 1(M)

Fluorogenic APEH Substrate Assay

Soluble brain proteomes (100 μL of 1 mg/mL protein) from AA74-1 (or vehicle)-injected mice were treated in a 96-well plate with N-acetyl-L-alanine 4-nitroanilide (100 μM final concentration) and the samples were incubated for 2 h at 37° C. Relative absorbance was measured with a plate reader at 440 nM. Inhibition curves were generated using PRISM® software (GraphPad). Calculated values represent means±s.e.m for three independent experiments.

Ex. 1(N)

APEH Substrate Assay with Synthetic Hexapeptides

Enzyme assays were performed with LC-MS by monitoring the formation of free N-acetyl amino acid. Mouse APEH was recombinantly expressed in HEK-293 cells and whole cell lysates of overexpressed APEH (or mock) were pre-treated with DMSO or 3 nM AA74-1 for 30 minutes and adjusted to a final protein concentration of 0.3 mg/mL with PBS buffer. For each reaction 200 μM of hexapeptide substrate were incubated with lysates in 200 μL total reaction volume. Reactions were incubated for 10 h at 37° C. before quenching with 0.8 mL MeOH. Subsequently, 100 nmol of $d_3$-serine were added to each reaction as an internal standard. Samples were centrifuged at 10,000×g at 4° C. for 10 minutes and the supernatant was transferred to a separate vial and dried down under vacuum. For LC-MS analysis samples were resuspended in 30 μL water and injected into an Agilent 1100 LC-MSD SL instrument applying the following gradient: Buffer A (MeCN) to Buffer B (95:5 $H_2O$/MeCN+50 mM $NH_4OAc$+0.2% $NH_4OH$) over 15 minutes at a flow rate of 0.5 mL/min. Data represent means±s.d. for three experiments.

Ex. 1(O)

Cell Proliferation Assay

BW5147-derived murine T-cell hybridoma cells were grown to 80% confluency in RPMI-1640 medium containing 10% FCS and supplemented with 40 mM L-glutamine in 10 cm dishes at 37° C. in a 5% $CO_2$ atmosphere before seeding in 96-well plates (Corning) at a density of 10,000 cells/well in 100 μL medium. Cells were incubated for 10 h (37° C., 5% $CO_2$) and then treated with inhibitor AA74-1 (1 nM final concentration) and incubated for further 12 h. About 10 μL of WST-1 reagent were added to each well and plates were incubated for 2 h in the dark at 37° C. Relative absorbance was measured with a plate reader at 440 nm. Data represent the average±s.d. for four experiments.

Ex. 1(P)

ABPP-MudPIT/SILAC/SILAM and N-Terminal Labeling

1(P)(a). Stable Isotope Labeling with Amino Acids in Cell Culture (SILAC).

BW5147-derived murine T-cell hybridoma cells were initially grown for 6 passages in either "light" or "heavy" SILAC RPMI 1640 media (Thermo) supplemented with 10% dialyzed FCS (Gemini) and 1×PSQ (see above). "Light" media was supplemented with 100 μg/mL L-arginine (Sigma) and 100 μg/mL L-lysine (Sigma). "Heavy" media was supplemented with 100 μg/mL [$^{13}C_6{}^{15}N_2$]-L-arginine (Isotek) and 100 μm/mL [$^{13}C_6{}^{15}N_4$]-L-lysine (Isotek). After the initial establishment of "light" and "heavy" cells, aliquots were frozen for future experiments to retain a low passage number. Cells were treated with inhibitors, collected and processed as described above.

1(P)(b). Stable Isotope Labeling of Mice (SILAM).

C57BL6 mice were labeled with $^{15}N$. Briefly, each mouse was fed an $^{15}N$-labeled protein diet starting immediately after weaning which continued for the next 10 weeks. The $^{15}N$-labeled diet was generated by combining spirulina biomass $^{15}N$-labeled (Cambridge Isotopes) with protein-free diet powder (Harlan TD 93328) in a 1:2 (wt/wt) ratio and an appropriate amount of $H_2O$ to generate a dough. This dough is then cut into 2-cm thick pellets and dried at 60° C. for 2-4 h and then at 35° C. overnight using an Excalibur food dehydrator. These $^{15}N$-labeled food pellets are then used to replace normal chow. After 10 weeks the $^{15}N$-labeled animals were subjected to halothane by inhalation until unresponsive, and the brains were quickly removed and frozen with liquid nitrogen. Brains were determined to be 95% labeled by mass spectrometry with $^{15}N$ and used for quantitative analysis. Brains were homogenized in 50 mM Tris pH 8.0 and prepared according to standard protocols to generate the soluble and membrane proteomes.

1(P)(c). Sample Preparation for ABPP-SILAC/SILAM.

The light and heavy proteomes were adjusted to a final protein concentration of 1.0 mg/mL and were labeled with 7 μM of FP-biotin (500 μL, total reaction volume) for 1.5 h at 25° C. After incubation, light and heavy proteomes were mixed in 1:1 ratio, and the membrane proteomes were additionally solubilized with 1% Triton-X. The proteomes were desalted over PD-10 desalting columns (GE Healthcare) and FP-labeled proteins were enriched with avidin beads. The beads were washed with 1% SDS in PBS (1×), PBS (3×), and $H_2O$ (3×), then resuspended in 6M urea, reduced with DTT for 15 minutes at 60° C., and alkylated with iodoacetamide for 30 minutes at 25° C. in the dark. On-bead digestions were performed for 12 h at 37° C. with trypsin (Promega; 4 μL, of 0.5 μg/μL) in the presence of 2 mM $CaCl_2$. Peptide samples were acidified to a final concentration of 5% formic acid, pressure-loaded on to a biphasic (strong cation exchange/reverse phase) capillary column and analyzed as described below.

1(P)(d). Sample Preparation for ABPP-MudPIT.

Proteomes of whole brain lysates were adjusted to a final protein concentration of 1.0 mg/mL and were labeled with 7 μM of FP-biotin (500 μL, total reaction volume) for 1.5 h at 25° C. Enrichment of FP-labeled proteins was performed as previously described. After enrichment the avidin beads were washed with 1% SDS in PBS (1×), PBS (3×), and $H_2O$ (3×). Beads were resuspended in 6M urea, reduced with DTT for 15 minutes at 60° C., and alkylated with iodoacetamide for 30 minutes at 25° C. in the dark. On-bead digestions were performed for 12 h at 37° C. with trypsin (Promega; 4 μL, of 0.5 μg/μL) in the presence of 2 mM $CaCl_2$. Peptide samples were acidified to a final concentration of 5% formic acid, pressure-loaded on to a biphasic (strong cation exchange/reverse phase) capillary column and analyzed as previously described using an Agilent 1100-series quaternary pump and Thermo Finnigan LTQ-MS.

1(P)(e). Sample Preparation for SILAC-Based N-Terminal Labeling.

The soluble light and heavy proteomes were adjusted to a final protein concentration of 1.0 mg/mL and were mixed in 1:1 ratio. 50 mM Ammonium bicarbonate buffer was added, the disulfides were reduced with DTT, and free cysteines alkylated with iodoacetamide. 30% Ammonium hydroxide was added, followed by lysine guanidination with large excess of O-methylisourea for 30 minutes at 65° C. The proteomes were concentrated and desalted with Amersham Biosciences PD-10 desalting columns. NHS-biotin was added as DMSO solution (10 mM final concentration) and the proteomes were warmed to 40° C. for 2 h. After desalting, the biotinylated proteins were enriched over avidin beads, and washed with 1% SDS in PBS (1×), PBS (3×), and $H_2O$ (3×). On-bead digestions were performed for 12 h at 37° C. with trypsin (Promega; 4 μL of 0.5 μg/μL) in the presence of 2 mM $CaCl_2$. Peptide samples were acidified to a final concentration of 5% formic acid, pressure-loaded on to a biphasic (strong cation exchange/reverse phase) capillary column and analyzed as described below.

1(P)(f). Sample Preparation for Unenriched SILAC.

The samples were prepared following the procedure for N-terminal labeling experiments, but without addition of NHS-biotin and enrichment over agarose beads. Trypsin digestions were performed in solution for 12 h at 37° C.

1(P)(g). Sample Preparation for Identification of Site of LYPLA1 Labeling by AA26-9.

Purified, recombinant mouse LYPLA1 (50 μM) was incubated with DMSO or AA26-9 (100 μM final) for 30 minutes at 37° C. The reactions were diluted with PBS (150 μL) and urea was added to 6 M final concentration. The disulfide bonds were reduced with DTT, and free cysteines alkylated with iodoacetamide. The samples were diluted again with 50 mM ammonium bicarbonate (300 μL) and subjected to trypsin digestion overnight at 37° C. The next day, the peptide samples were acidified to a final concentration of 5% formic acid and a 20 μL aliquot was pressure loaded onto a 100 μm (inner diameter) fused silica capillary column with a 5 μm tip that contained 10 cm C18 resin (aqua 5 μm, Phenomenex). LC-MS/MS analysis was performed on an Thermo Scientific LTQ Orbitrap ion trap mass spectrometer coupled to an Agilent 1100 series HPLC. Peptides were eluted from the column using a 125 minutes gradient of 5%-100% Buffer B (Buffer B: 20% water, 80% acetonitrile, 0.1% formic acid).

1(P)(h). LC-MS/MS Analysis.

Digested and acidified peptide mixtures were analyzed by two-dimensional liquid chromatography (2D-LC) separation in combination with tandem mass spectrometry using an Agilent 1100-series quaternary pump and Thermo Scientific LTQ ORBITRAP® ion trap mass spectrometer. Peptides were eluted in a 5-step MudPIT experiment using 0%, 25%, 50%, 80%, and 100% salt bumps of 500 mM aqueous ammonium acetate (12-step experiment for N-terminal labeling MudPIT) and data were collected in data-dependent acquisition mode with dynamic exclusion turned on (60 s, repeat of 1). Specifically, one full MS (MS1) scan (400-1800 m/z) was followed by 7 MS2 scans of the most abundant ions. The MS2 spectra data were extracted from the raw file using RAW Xtractor (version 1.9.1; publicly available at the website fields.scripps.edu/?q=content/download). MS2 spectra data were searched using the SEQUEST algorithm (Version 3.0) against the latest version of the mouse IPI database concatenated with the reversed database for assessment of false-discovery rates. SEQUEST searches allowed for variable oxidation of methionine (+16), static modification of cysteine residues (+57 due to alkylation), and no enzyme specificity. The resulting MS2 spectra matches were assembled into protein identifications and filtered using DTASelect (version 2.0.41) using the -trypstat option, which applies different statistical models for the analysis of tryptic, half-tryptic, non-tryptic peptides. DTASelect 2.0 uses a quadratic discriminant analysis to achieve a user-defined maximum peptide false positive rate; the default parameters (maximum false positive rate of 5%) was used for the search; however, the actual false positive rate was much lower (1%).

For ABPP-MudPIT only proteins for which 5 or more spectral counts were identified on average in the control samples were considered for comparative analysis. Specifically, probe-labeled proteins were further identified by their presence in FP-treated samples with a spectral number at least 5-fold or greater than that observed in "no probe" control runs (experiments performed as described above, but without inclusion of biotinylated FP). Spectral counts are reported as the average of three samples with the standard error of the mean (SEM).

SILAC and SILAM ratios were quantified using an improved version of the in-house software as described in reference. The program was modified to allow users to flexibly define chemical compositions of both "light" and "heavy" amino acids used in current experiment so that extracted ion chromatograms of "light" and "heavy" peptides can be correctly generated. For SILAM experiments, the predicted pattern of the isotopic envelope of the target peptide takes into account the actual $^{15}N$ enrichment percentage and it increases the accuracy of the "envelope correlation score" to filter false-positive peptide identification and quantification.

Ex. 1(Q)

DAGL Inhibition Studies

1(Q)(a). Materials.

Pharmacological studies were conducted in C57BL/6 mice unless indicated otherwise. Daglb$^{+/+}$, Daglb$^{+/-}$, and Daglb$^{-/-}$ mice were on a mixed genetic background of C57BL/6 and 129/SvEv and were obtained from Taconic. Pla2g4a$^{+/+}$ and Pla2g4a$^{-/-}$ mice on a BALB/c background were obtained from Joseph Bonventre's laboratory at Brigham and Women's Hospital. FP-rhodamine and FP-biotin were synthesized according to a previously described protocol. All triazole-urea compounds were synthesized in the laboratory. All other chemicals and reagents were purchased from Sigma. All deuterated lipid standards and substrates were purchased from Cayman Chemicals. The Mouse Inflammatory Cytokines Single-Analyte ELISARRAY® kit was purchased from Qiagen. Neuro2A and HEK293T cells were obtained from ATCC. Full-length cDNAs encoding serine hydrolases were purchased from Open Biosystems.

1(Q)(b). Metabolite Measurements.

Metabolites were quantified by either selected reaction monitoring (SRM) of each metabolite using an Agilent G6410B Triple-Quad instrument or untargeted metabolomic analysis (substrate assays) using an Agilent 1100 series LC-MSD SL instrument. Liquid chromatography (LC) separation was achieved with a Gemini reverse-phase C18 column (50 mm, 4.6 mm with 5 µm diameter particles, Phenomonex) together with a pre-column (C18, 3.5 µm, 2 mm×20 mm). For analysis of diacylglycerols (DAGs) a Luna C5 column (50 mm×4.60 mm with 5 µm diameter particles) from Phenomenex was used. Mobile phase A was made of 95:5 v/v $H_2O$:MeOH, and mobile phase B was composed of 60:35:5 v/v/v i-PrOH:MeOH:$H_2O$. Ammonium hydroxide (0.1%) and formic acid (0.1%) was included to assist in ion formation in negative and positive ionization modes, respectively. For analysis of DAGs, 5 mM ammonium formate was also used in addition to 0.1% formic acid to assist in positive ionization and $NH_4+$ adduct formation. For metabolite measurements, cells were resuspended in 1 mL of a 1% NaCl solution and added to 3 mL of a 2:1 v/v $CHCl_3$:MeOH doped with 1 nmol of the following internal standards: $d_5$-2-arachidonoylglycerol (2-AG), $d_8$-arachidonic acid (AA), and $d_8$-1-stearoyl-2-arachidonoylglycerol (SAG). The mixture was vortexed and then centrifuged (1,400×g, 3 min). The organic layer was removed, $CHCl_3$ was added until the final volume was again 4 ml, and the extraction was repeated. The combined organic extracts were dried under a stream of N2 and resolubilized in 2:1 v/v $CHCl_3$:MeOH (120 µl). 30 µL of resolubilized lipids were injected for positive mode (MAGs and DAGs) and negative mode (free fatty acids and eicosanoids) measurements.

For targeted analysis in positive mode, the flow rate for each run started at 0.1 mL/min with 0% B. At 5 min, the solvent was changed immediately to 60% B with a flow rate of 0.4 mL/min and increased linearly to 100% B over 15 min. This was followed by an isocratic gradient of 100% B for 8 min at 0.5 mL/min before equilibrating for 3 min at 0% B at 0.5 mL/min. For targeted analysis in negative mode, the flow rate for each run started at 0.1 mL/min with 0% B. At 3 min, the flow rate was increased by 0.4 mL/min with a linear increase of solvent B to 100% over 17 min. This was followed by isocratic gradient of 100% B for 7 min at 0.5 mL/min before equilibrating for 3 min with 0% B at 0.5 mL/min. For measurement of hydrolysis products in enzyme substrate assays (positive mode), the flow rate for each run started at 0.1 mL/min with 0% B. At 5 min, the solvent was changed immediately to 100% B with a flow rate of 0.4 mL/min. This was followed by an isocratic gradient of 100% B for 5 min at 0.5 mL/min before equilibrating for 5 min with 0% B at 0.5 mL/min.

The following parameters (MS) were used to measure the indicated metabolites by SRM (precursor ion, product ion, collision energy in V, polarity): C20:4 MAG or 2-AG (379, 287, 8, positive), $d_5$-2-AG (384, 287, 5, positive), C18:0/C20:4 DAG or SAG (662, 341, 15, positive), $d_8$-SAG (671, 671, 0, positive), C18:1/C20:4 DAG (660, 341, 15, positive), C16:0/C20:4 DAG (634, 341, 15, positive), C14:0/C20:4 DAG (606, 341, 15, positive), arachidonic acid or AA (303, 303, 0, negative), $d_8$-AA (311, 267, 5, negative), PGE2 (351, 271, 10, negative), and PGD2 (351, 271, 10, negative). MS analysis was performed with an electrospray ionization source with the following parameters: drying gas temperature=350° C., drying gas flow rate=11 L/min, and the nebulizer pressure=35 psi. Prostaglandin SRM parameters were based on previously reported methods and transitions. Metabolites targeted by SRM were quantified by measuring the area under the peak in comparison with the internal standards. For metabolites where isotopic internal standards were not used, external standard curves with the internal standard versus metabolite standard were generated. In DAGL substrate assays, formation of the hydrolysis product, 2-AG was followed by measuring the area under the peak for 2-AG in comparison to the 1-monopentadecanoin standard ion.

1(Q)(c). DAGL Hydrolysis Assay.

The activity of DAGL-alpha (DAGLA) and DAGL-beta (DAGLB) was determined using recombinant VS-tagged protein overexpressed in HEK293T cells as previously described with some minor modifications. HEK293T-DAGLA or HEK293T-DAGLB membrane lysates were diluted to 2 mg/mL or 0.3 mg/mL (70 µL sample volume) respectively, in DAGL solution (5 mM $CaCl_2$, 100 mM NaCl, 50 mM HEPES). Lysates were treated with DMSO or compound for 30 min at 37° C. The substrate was prepared by sonicating 1-stearoyl-2-arachidonoylglycerol (SAG) in DAGL solution (5 mM CaCl$_2$, 100 mM NaCl, 50 mM HEPES)+0.005% and 0.5% Triton X-100 for DAGLA and DAGLB, respectively. The substrate was added to the sample reaction (30 μL, 500 μM final concentration of SAG), sonicated for 5 sec, and then incubated for 30 min at 37° C. The reaction was quenched by adding 300 μL of 2:1 v/v CHCl$_3$: MeOH, doped with 1 nmol of 1-monopentadecanoin standard, vortexed and then centrifuged (1,400×g, 3 min) to separate the phases. The organic phase was subjected to LC-MS analysis and 2-AG was quantified as described above.

1(Q)(d). Gel-Based Competitive ABPP.

Gel-based competitive ABPP experiments were performed as previously described. Proteomes (1 mg/mL) were treated with either FP-rhodamine or HT-01 (1 μM final concentration) in a 50 μL total reaction volume. After 30 min at 37° C., the reactions were quenched with SDS-PAGE loading buffer. After separation by SDS-PAGE (10% acrylamide), samples were visualized by in-gel fluorescence scanning using a flatbed fluorescent scanner (Hitachi FMBioIIe).

1(Q)(e). ABPP-SILAC Sample Preparation.

The soluble and membrane fractions were isolated by centrifugation (100K×g, 45 min) and the protein concentration for each fraction was adjusted to 2 mg/mL with DPBS. The light and heavy proteomes were labeled with the activity-based affinity probe FP-biotin (500 μL total reaction volume, 10 μM final concentration) for 2 h at 25° C. After incubation, light and heavy proteomes were mixed in 1:1 ratio, and the membrane proteomes were additionally solubilized with 1% Triton-X100. Samples were desalted over PD10 columns (GE Healthcare) in DPBS, and biotinylated proteins enriched with streptavidin beads (50 μL beads; conditions: 1 h, 25° C., 0.5% SDS in DPBS). The beads were washed with 1% SDS in DPBS (1×), 6 M urea (1×), and DPBS (2×), then resuspended in 6 M urea (150 μL), reduced with 5 mM TCEP for 20 min, and alkylated with 10 mM iodoacetamide for 30 min at 25° C. in the dark. The urea concentration was reduced to 2 M with 2× volume DPBS. On-bead digestions were performed for 12 h at 37° C. with sequence-grade modified trypsin (Promega; 2 μg) in the presence of 2 mM CaCl$_2$. Peptide samples were acidified to a final concentration of 5% (v/v) formic acid and stored at −80° C. prior to analysis.

1(Q)(f). ABPP-MudPIT Sample Preparation.

Peritoneal macrophage proteomes were adjusted to a final protein concentration of 2 mg/mL and labeled with FP-biotin (500 μL total reaction volume, 10 μM final concentration) for 2 hours at 25° C. After incubation the proteomes were additionally solubilized with 1% Triton-X100. Samples were desalted over PD10 columns (GE Healthcare) in DPBS, and biotinylated proteins enriched with streptavidin beads (50 μL beads; conditions: 1 h, 25° C., 0.5% SDS in DPBS). The beads were washed with 1% SDS in DPBS (1×), 6 M urea (1×), and DPBS (2×), then resuspended in 6 M urea (150 μL), reduced with 5 mM TCEP for 20 minutes, and alkylated with 10 mM iodoacetamide for 30 minutes at 25° C. in the dark. The urea concentration was reduced to 2 M with 2× volume DPBS. On-bead digestions were performed for 12 h at 37° C. with sequence-grade modified trypsin (Promega; 2 μg) in the presence of 2 mM CaCl$_2$. Peptide samples were acidified to a final concentration of 5% (v/v) formic acid and stored at −80° C. prior to analysis.

1(Q)(g). Determination of IC$_{50}$ Values.

For gel-based competitive ABPP studies, proteomes from cells treated in situ with inhibitor for 4 h at 37° C. at the indicated concentrations (n=3) were labeled with HT-01 (1 μM) for 30 min at 37° C. After quenching, SDS-PAGE, and in-gel visualization, the percentage of enzyme activity remaining was determined by measuring the integrated optical intensity of the bands using IMAGER® software. For LC-MS substrate assays, the percentage of enzyme activity remaining was determined by comparing the specific activity (amount of 2-AG formed per min per mg of proteome) of inhibitor with DMSO-treated samples. The IC$_{50}$ values were determined from a dose-response curve generated using GraphPad PRISM® software.

1(Q)(h). LC-MS/MS Analysis of SILAC and In Vivo Samples.

Samples were analyzed by multidimensional liquid chromatography tandem mass spectrometry (MudPIT) using an Agilent 1200-series quaternary pump and Thermo Scientific LTQ-Orbitrap ion trap mass spectrometer as previously described. Peptides were eluted in a 5-step MudPIT experiment using 0%, 25%, 50%, 80%, and 100% salt bumps of 500 mM aqueous ammonium acetate and data were collected in data-dependent acquisition mode with dynamic exclusion turned on (20 s, repeat of 1). Specifically, one full MS (MS1) scan (400-1800 m/z) was followed by 30 MS2 scans of the most abundant ions. The MS2 spectra data were extracted from the raw file using RAW Xtractor (version 1.9.9.2; publicly available at the website fields.scripps.edu/download-s.php. MS2 spectra data were searched using the ProLuCID algorithm (publicly available at the website fields.s-cripps.edu/downloads.php) against the latest version of the mouse IPI database concatenated with the reversed database for assessment of false-discovery rates. ProLucid searches allowed for static modification of cysteine residues (+57.02146 due to alkylation), methionine oxidation (+15.9949), mass shifts of labeled amino acids (+10.0083 R, +8.0142K) and no enzyme specificity. The resulting MS2 spectra matches were assembled into protein identifications and filtered using DTASelect (version 2.0) using the -modstat, -mass, and -trypstat options (applies different statistical models for the analysis of high resolution masses, peptide digestion state, and methionine oxidation state respectively). Ratios of heavy/light (test compound/DMSO) peaks were calculated using in-house software and normalized at the peptide level to the average ratio of all non-serine hydrolase peptides. Reported ratios represent the mean of all unique, quantified peptides per protein and do not include peptides that were >3 standard deviations from the median peptide value. Proteins with less than three peptides per protein ID were not included in the analysis.

For LC-MS/MS analysis of in vivo samples digested and acidified peptide mixtures were analyzed by two-dimensional liquid chromatography/tandem mass spectrometry (MudPIT) using an Agilent 1200-series quaternary pump and Thermo Scientific LTQ ion trap mass spectrometer. Spectral counts were calculated for all serine hydrolases with an average of 4 or more spectral counts in the DMSO control samples except ABHD6, which was included even if signal intensities were below the cutoff. Spectral counts are reported as the average of three samples with the standard error of the mean (SEM).

Ex. 1(R)

Structural Assignment of Substituted Triazole Urea Regioisomers

In all reactions the major regioisomeric product showed an upfield $^1$H-NMR shift of the triazole ring proton and slower migration on the TLC plate relatively to the minor isomer. Single crystals of the minor isomer of compound AA80-1 and the major isomer of the structurally closely related compound KT117 were obtained from a saturated acetonitrile solution and the relative configuration was determined by X-ray crystallography. Accordingly, the major regioisomers were assigned as 2,4-triazole ureas (N2-carbamoyl) and the minor products as the 1,4-triazole ureas (N1-carbamoyl).

Ex. 1(S)

Structural Assignment of Unsubstituted Triazole Urea Regioisomers

In all reactions, the two triazole ring protons of the major product formed two doublets in the $^1$H-NMR spectrum with an integration of one each, as expected for an unsymmetrical, unsubstituted triazole urea. The two triazole ring protons for the minor isomer formed a singlet with an integration of two, as expected for a symmetrical, unsubstituted triazole urea. Accordingly, the major products were assigned as N1-carbamoyl triazole ureas, and the minor products as the N2-carbamoyl triazole ureas.

Example 2

Synthetic Methods

Ex. 2(A)

General Synthetic Methods

All reagents were purchased from Sigma-Aldrich, Acros, Fisher, Fluka, or Maybridge and used without further purification, except where noted. Dry solvents were obtained by passing commercially available pre-dried, oxygen-free formulations through activated alumina columns. All reactions were carried out under a nitrogen atmosphere using oven-dried glassware unless otherwise noted. Flash chromatography was performed using 230-400 mesh silica gel. NMR spectra were recorded in CDCl$_3$ or d$_6$-DMSO on a Varian Inova-400 spectrometer and were referenced to trimethylsilane (TMS) or the residual solvent peak. Chemical shifts are reported in ppm relative to TMS and J values are reported in Hz. High resolution mass spectrometry (HRMS) experiments were performed at The Scripps Research Institute Mass Spectrometry Core on an Agilent mass spectrometer using electrospray ionization-time of flight (ESI-TOF).

Ex. 2(B)

General Procedure 1. Synthesis of Carbamoyl Chlorides from Secondary Amines

Amine (1 equiv.) was dissolved in dry CH$_2$Cl$_2$ (10 mL/mmol amine) and cooled to 0° C. Triphosgene (0.6 equiv.) was added and the reaction was stirred for 10 minutes at 0° C. and for further 15 minutes at room temperature. The reaction was carefully quenched by dropwise addition of sat. aq. NaHCO$_3$, diluted with CH$_2$Cl$_2$, and washed with brine. The organic phase was dried over Na$_2$SO$_4$ and the solvent was removed under reduced pressure (water bath temperature <30° C.). The crude carbamoyl chloride was used for the next step without further purification.

Ex. 2(C)

General Procedure 2. One-Pot Synthesis of NH-1,2,3-Triazoles

NH-1,2,3-Triazoles were prepared following a slightly modified procedure of Fokin et al. A mixture of 37% HCHO (10 equiv.), glacial AcOH (1.5 equiv), and THF (1 mL/mmol alkyne) was stirred for 15 min. Sodium azide was added (1.5 equiv.), followed by the alkyne (1 equiv.). The mixture was stirred for 10 minutes and sodium ascorbate (0.2 equiv.) was added, followed by CuSO$_4$ solution (200 mg/mL H$_2$O; 5 mol %). The reaction was stirred for 24 h at room temperature (at 60° C. for tertiary alcohol triazoles). The solvents were removed and the residue was re-dissolved in 3:1 MeOH/2N NaOH (1 mL/mmol alkyne). After stirring for 24 h at room temperature, the solvents were azeotropically removed and the residue was purified by silica gel chromatography (15:85:1 MeOH/CH$_2$Cl$_2$/NEt$_3$) to yield the desired NH-1,2,3-triazole.

Ex. 2(D)

General Procedure 3. Synthesis of Triazole Ureas from Carbamoyl Chlorides

Mixture of triazole (1.2 equiv.), carbamoyl chloride (1 equiv.), and 4-DMAP (cat.) in 5:1 THF/NEt$_3$ (2 mL/mmol carbamoyl chloride) was stirred for 10 h at 60° C. The solvents were removed to yield the desired triazole urea, typically as a mixture of regioisomers, i.e., N2-carbamoylated (i.e. 2,4-regioisomer) and N1-carbamoylated (1,4-regioisomer), in N2:N1 ratios in the range of about 1.5:1 to about 3:1 for 4-substituted triazoles, and N2:N1 ratios of about 1:3 to 1:5 for unsubstituted triazoles. The N1- and N2-carbamoyl-1,2,3-triazoles were separated by silica gel chromatography (3:1 hexanes/ethyl acetate->ethyl acetate) and the major isomers (in some cases both isomers) were characterized.

Example 3

Synthesis of Activity-Based Probes AA6-10

A series of activity-based probes was prepared, as shown in FIG. 19 (probes AA6 through AA10).

Ex. 3(A)

N-Benzyl-2-(2-(2-(Propynyloxy)Ethoxy)Ethoxy) Ethyl Amine (27)

2-[2-(2-Chloroethoxy) ethoxy]ethanol 26 (1 g, 5.9 mmol) was dissolved in DMF (15 mL), and propargyl bromide (1.3 mL, 11.8 mmol) was added. The reaction was cooled to 0° C., and sodium hydride (60% dispersion, 356 mg, 8.9 mmol) was added and stirred for 4 h at 65° C. The reaction was quenched with 0.5 M aq. HCl, and extracted 3× with EtOAc. The combined organic phases were dried over Na$_2$SO$_4$. The residue was purified by silica gel chromatography (hexanes/ethyl acetate 9:1->3:1) to afford the alkyne (1.2 g, 5.6 mmol, 94%).

Alkyne (525 mg, 2.54 mmol) was dissolved in DMF (10 mL), and benzyl amine (1.66 mL, 15.24 mmol) was added. The reaction was cooled to 0° C., and K$_2$CO$_3$ (3.5 g, 25.4 mmol) was added, followed by the addition of cat. amount of tetrabutylammonium iodide (TBAI). The reaction was stirred for 10 h at 100° C. The solvent was removed and the residue was purified by silica gel chromatography (CH$_2$Cl$_2$->20% MeOH and 1% NEt$_3$ in CH$_2$Cl$_2$) to give the amine 27 (628 mg, 2.26 mmol, 89%). $^1$H-NMR (400 MHz, CDCl$_3$): δ=7.40-7.23 (m, 5H), 4.23 (dd, J=1.4, 2.4 Hz, 2H), 3.81-3.51 (m, 12H), 2.88-2.81 (m, 2H), 2.40 (m, 1H). HRMS (m/z): calcd for C$_{16}$H$_{24}$NO$_3$ [M+H]$^+$: 278.1751. found: 278.1747.

Ex. 3(B)

Probe AA6 (1)

Amine 27 (320 mg, 1.15 mmol) was dissolved in $CH_2Cl_2$ (8 mL), and triethylamine (1 mL) was added, followed by the addition of p-nitrophenyl chloroformate (301 mg, 1.5 mmol). The reaction was stirred for 10 h at room temperature. The solvents were removed and the residue was purified by silica gel chromatography (3:1 hexanes-to-ethyl acetate->1:1 hexanes/ethyl acetate) to give carbamate AA6 (422 mg, 0.95 mmol, 83%). $^1$H-NMR (400 MHz, $CDCl_3$): δ=8.27-8.23 (m, 2H), 7.42-7.24 (m, 7H), 4.80 (s, 1H), 4.69 (s, 1H), 4.21 (m, 2H), 3.73-3.58 (m, 12H), 2.40 (m, 1H). HRMS (m/z): calcd for $C_{23}H_{27}N_2O_7$ $[M+H]^+$: 443.1813. found: 443.1819.

Ex. 3(C)

N-Benzyl-2-(2-(2-(propynyloxy)ethoxy)ethoxy)ethyl aminocarbonyl chloride

N-Benzyl-2-(2-(2-(propynyloxy)ethoxy)ethoxy)ethyl aminocarbonyl chloride was prepared from amine 27 (20 mg, 0.072 mmol) following General Procedure 1. The crude carbamoyl chloride was used directly for the next step.

Ex. 3(D)

Probe AA7 (2)

Following the General Procedure 3, crude carbamoyl chloride (from 0.072 mmol amine 27) was reacted with imidazole (6 mg, 0.088 mmol) to yield probe AA7 (16 mg, 0.043 mmol, 60% over 2 steps). $^1$H-NMR (400 MHz, $CDCl_3$): δ=8.49 (bs, 1H), 7.51-7.27 (m, 7H), 4.78 (t, J=19 Hz, 2H), 4.19 (m, 2H), 3.72-3.53 (m, 12H), 2.40 (m, 1H). HRMS (m/z): calcd for $C_{20}H_{26}N_3O_4$ $[M+H]^+$: 372.1918. found: 372.1922.

Ex. 3(E)

Probe AA8 (3)

Following the General Procedure 3, crude carbamoyl chloride (from 0.072 mmol amine 27) was reacted with 1H-1,2,3-triazole (6 mg, 0.088 mmol) to yield probe AA8 (15 mg, 0.040 mmol, 56% over 2 steps). $^1$H-NMR (400 MHz, $CDCl_3$): δ=7.80 (bs, 1H), 7.70 (bs, 1H), 7.48-7.22 (m, 5H), 4.89 (m, 2H), 4.17 (m, 2H), 3.84-3.52 (m, 12H), 2.40 (m, 1H). HRMS (m/z): calcd for $C_{19}H_{25}N_4O_4$ $[M+H]^+$: 373.1870. found: 373.1873.

Ex. 3(F)

Probe AA9 (4)

Following the General Procedure 3, crude carbamoyl chloride (from 0.072 mmol amine 27) was reacted with commercially available phenyl triazole (6 mg, 0.088 mmol) to yield probe AA9 (21 mg, 0.047 mmol, 65% over 2 steps). $^1$H-NMR (400 MHz, $CDCl_3$): δ=8.05 (s, 1H), 7.85-7.79 (m, 2H), 7.47-7.26 (m, 8H), 4.95 (m, 2H), 4.18 (m, 2H), 3.80-3.51 (m, 12H), 2.40 (m, 1H). HRMS (m/z): calcd for $C_{25}H_{29}N_4O_4$ $[M+H]^+$: 449.2183. found: 449.2180.

Ex. 3(G)

Probe AA10 (5)

Following the General Procedure 3, crude carbamoyl chloride (from 0.072 mmol amine 27) was reacted with commercially available 1H-1,2,3-triazolo[4,5-b]pyridine (11 mg, 0.088 mmol) to yield probe AA10 (12 mg, 0.028 mmol, 39% over 2 steps). $^1$H-NMR (400 MHz, $CDCl_3$): δ=8.78 (m, 1H), 8.47 (m, 1H), 7.59-7.28 (m, 6H), 5.06 (m, 2H), 4.22 (m, 2H), 3.90-3.63 (m, 12H), 2.40 (m, 1H). HRMS (m/z): calcd for $C_{22}H_{26}N_5O_4$ $[M+H]^+$: 424.1979. found: 424.1985.

Example 4

Figure 20:
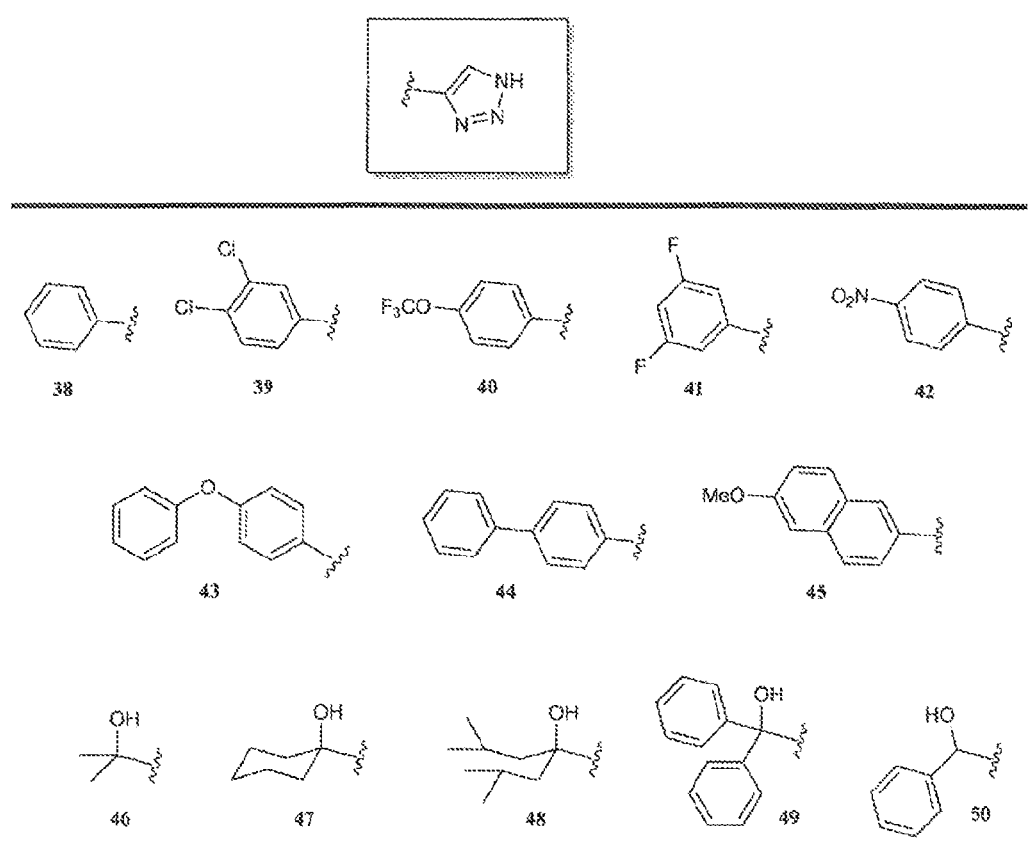
FIG. 20 provides structures of some representative substituted 1,2,3-triazole compounds useful in the preparation of triazole ureas as described herein.

Synthesis of 2-substituted NH-1,2,3-Triazoles (for structures see FIG. 20)

A series of 2-substituted NH-1,2,3-triazoles was prepared, as shown in FIG. 20. These triazole compounds are useful intermediates for the preparation of 1,2,3-triazole urea compounds, e.g., as described herein in Example 5.

Ex. 4(A)

Triazole 38

Triazole 38 was purchased from American Custom Chemicals (ACC) Corporation.

Ex. 4(B)

Triazole 39

Following the General Procedure 2, (3,4-dichloro)phenyl acetylene (462 mg, 2.7 mmol) was reacted with sodium azide (260 mg, 4 mmol) to obtain triazole 39 (457 mg, 2.1 mmol, 79%). $^1$H-NMR (400 MHz, $d_6$-DMSO): δ=8.45 (s, 1H), 7.98-7.46 (m, 3H). HRMS (m/z): calcd for $C_8H_6Cl_2N_3$ $[M+H]^+$: 213.9933. found: 213.9931.

Ex. 4(C)

Triazole 40

Following the General Procedure 2, (4-trifluoromethoxy) phenyl acetylene (500 mg, 2.7 mmol) was reacted with sodium azide (260 mg, 4 mmol) to obtain triazole 40 (531 mg, 2.3 mmol, 86%). $^1$H-NMR (400 MHz, $d_6$-DMSO): δ=8.13 (s, 1H), 7.55-7.41 (m, 2H), 6.92-6.85 (m, 2H). HRMS (m/z): calcd for $C_9H_7F_3N_3$ $[M+H]^+$: 230.0536. found: 230.0540.

Ex. 4(D)

Triazole 41

Following the General Procedure 2, (3,5-difluoro)phenyl acetylene (372 mg, 2.7 mmol) was reacted with sodium azide (260 mg, 4 mmol) to obtain triazole 41 (405 mg, 2.2 mmol, 83%). $^1$H-NMR (400 MHz, $d_6$-DMSO): δ=8.07 (s, 1H), 7.20-7.11 (m, 2H), 6.95-6.87 (m, 1H). HRMS (m/z): calcd for $C_8H_6F_2N_3$ $[M+H]^+$: 182.0524. found: 182.0527.

Ex. 4(E)

Triazole 42

Following the General Procedure 2, (4-nitro)phenyl acetylene (397 mg, 2.7 mmol) was reacted with sodium azide (260 mg, 4 mmol) to obtain triazole 42 (370 mg, 1.9 mmol, 72%). $^1$H-NMR (400 MHz, $d_6$-DMSO): δ=8.26 (s, 1H), 7.91-7.80

Ex. 4(F)

Triazole 43

Following the General Procedure 2, (4-phenyloxy)phenyl acetylene (524 mg, 2.7 mmol) was reacted with sodium azide (260 mg, 4 mmol) to obtain triazole 43 (532 mg, 2.2 mmol, 83%). $^1$H-NMR (400 MHz, $d_6$-DMSO): δ=8.03 (s, 1H), 7.95-7.82 (m, 4H), 7.35-7.13 (m, 5H). HRMS (m/z): calcd for $C_{14}H_{12}N_3O$ $[M+H]^+$: 238.0975. found: 238.0978.

Ex. 4(G)

Triazole 44

Following the General Procedure 2, (4-phenyl)phenyl acetylene (481 mg, 2.7 mmol) was reacted with sodium azide (260 mg, 4 mmol) to obtain triazole 44 (525 mg, 2.4 mmol, 88%). $^1$H-NMR (400 MHz, $d_6$-DMSO): δ=8.26 (s, 1H), 7.88-7.27 (m, 9H). HRMS (m/z): calcd for $C_{14}H_{12}N_3$ $[M+H]^+$: 222.1026. found: 222.1028.

Ex. 4(H)

Triazole 45

Following the General Procedure 2, (6-methoxy)naphthyl acetylene (492 mg, 2.7 mmol) was reacted with sodium azide (260 mg, 4 mmol) to obtain triazole 45 (517 mg, 2.3 mmol, 85%). The analytical data were in agreement with those reported in the literature[12].

Ex. 4(I)

Triazole 46

Following the General Procedure 2, 2-methyl-3-butyn-2-ol (227 mg, 2.7 mmol) was reacted with sodium azide (260 mg, 4 mmol) to obtain triazole 46 (213 mg, 1.7 mmol, 62%). $^1$H-NMR (400 MHz, $d_6$-DMSO): δ=7.74 (s, 1H), 1.45 (bs, 6H). HRMS (m/z): calcd for $C_5H_{10}N_3O$ $[M+H]^+$: 128.0818. found: 128.0821.

Ex. 4(J)

Triazole 47

Following the General Procedure 2, 1-ethynyl-1-cyclohexanol (335 mg, 2.7 mmol) was reacted with sodium azide (260 mg, 4 mmol) to obtain triazole 47 (257 mg, 1.5 mmol, 57%). $^1$H-NMR (400 MHz, $d_6$-DMSO): δ=7.72 (s, 1H), 1.82-1.21 (m, 10H). HRMS (m/z): calcd for $C_8H_{14}N_3O$ $[M+H]^+$: 168.1131. found: 168.1130.

Ex. 4(K)

Triazole 48

Following the General Procedure 2, 4-ethynyl-2,6-dimethyl-4-heptanol (454 mg, 2.7 mmol) was reacted with sodium azide (260 mg, 4 mmol) to obtain triazole 48 (365 mg, 1.7 mmol, 64%). $^1$H-NMR (400 MHz, $d_6$-DMSO): δ=7.73 (s, 1H), 1.84-1.53 (m, 6H), 0.92 (bs, 6H), 0.74 (bs, 6H). HRMS (m/z): calcd for $C_{11}H_{22}N_3O$ $[M+H]^+$: 212.1757. found: 212.1759.

Ex. 4(L)

Triazole 49

Following the General Procedure 2, 1,1-diphenyl-2-propyn-1-ol (562 mg, 2.7 mmol) was reacted with sodium azide (260 mg, 4 mmol) to obtain triazole 49 (495 mg, 2.0 mmol, 73%). $^1$H-NMR (400 MHz, $d_6$-DMSO): δ=7.82 (s, 1H), 7.54-7.27 (m, 10H). HRMS (m/z): calcd for $C_{15}H_{14}N_3O$ $[M+H]^+$: 252.1131. found: 252.1135.

Ex. 4(M)

Triazole 50

Following the General Procedure 2,1-phenyl-2-propyn-1-ol (357 mg, 2.7 mmol) was reacted with sodium azide (260 mg, 4 mmol) to obtain triazole 50 (364 mg, 2.1 mmol, 77%). $^1$H-NMR (400 MHz, $d_6$-DMSO): δ=7.82 (s, 1H), 7.52-7.31 (m, 5H), 5.64 (bs, 1H). HRMS (m/z): calcd for $C_9H_{10}N_3O$ $[M+H]^+$: 176.0818. found: 176.0814.

Example 5

Figure 3:
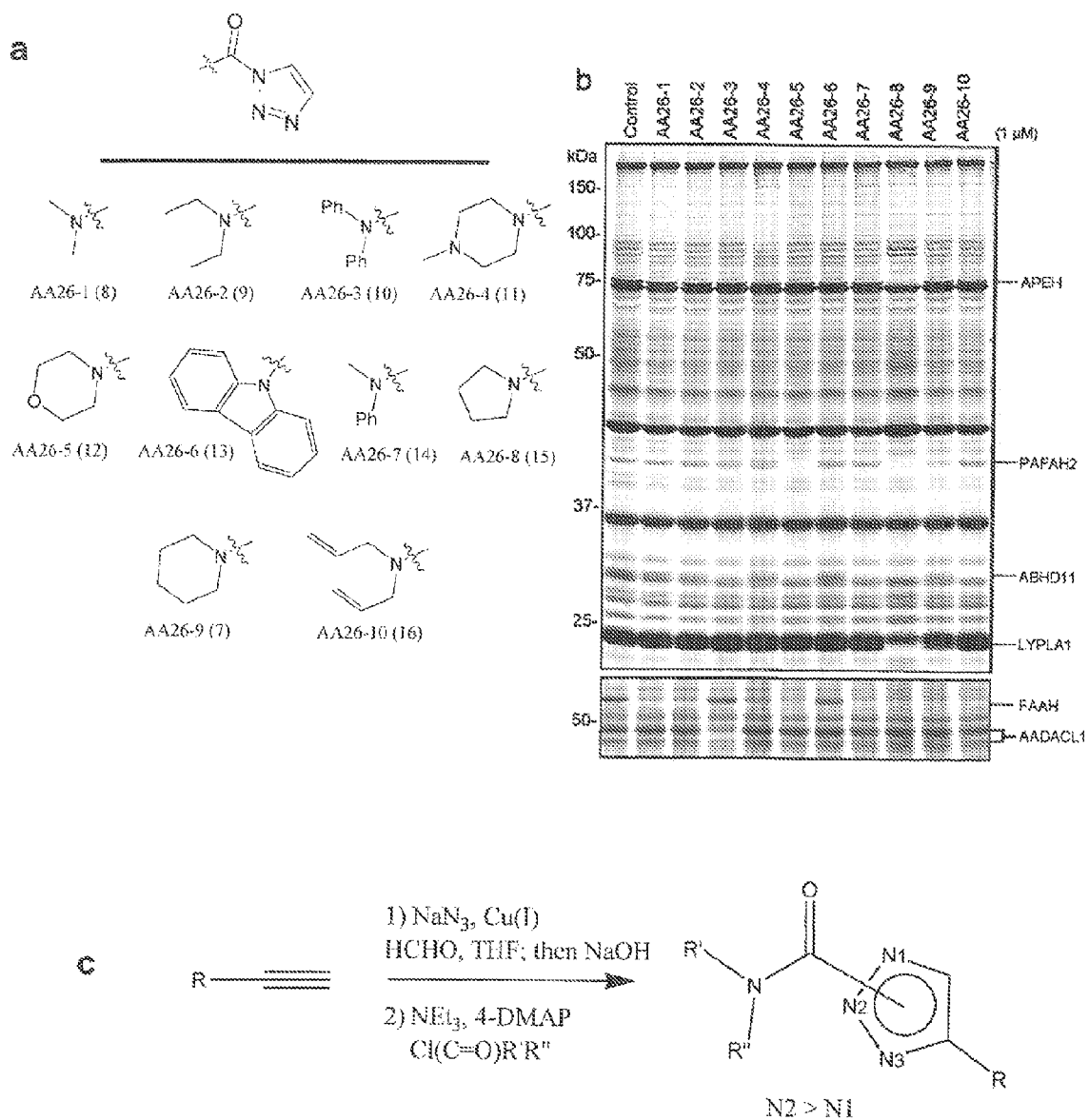
FIG. 3 illustrates rapid optimization of triazole urea inhibitors by click chemistry-enabled synthesis and competitive ABPP. (a) Structures of ten 1,2,3-triazole ureas (AA26-1-AA26-10) with distinct carbamoyl substituents combined with a uniform, unsubstituted 1,2,3-triazole leaving group. (b) Reactivity profiles for AA26-1-AA26-10 in vitro. Soluble and membrane fractions of mouse T-cells were incubated with inhibitors (1 µM) for 30 minutes at 37° C., after which the samples were analyzed by competitive gel-based ABPP. (c) A general click chemistry-based route for the synthesis of substituted 1,2,3-triazole ureas. (d) Structures of representative pyrrolidine and piperidine compounds with functionalized 1,2,3-triazole leaving groups. (e) Competitive ABPP results for functionalized 1,2,3-triazole urea inhibitors in mouse T-cells in vitro (treated with inhibitors at the indicated concentrations for 30 minutes at 37° C.). Inhibitors AA39-2, AA74-1, and AA44-2 each inhibited only a single SH target in the T-cell proteome (highlighted with boxes).
Figure 3:
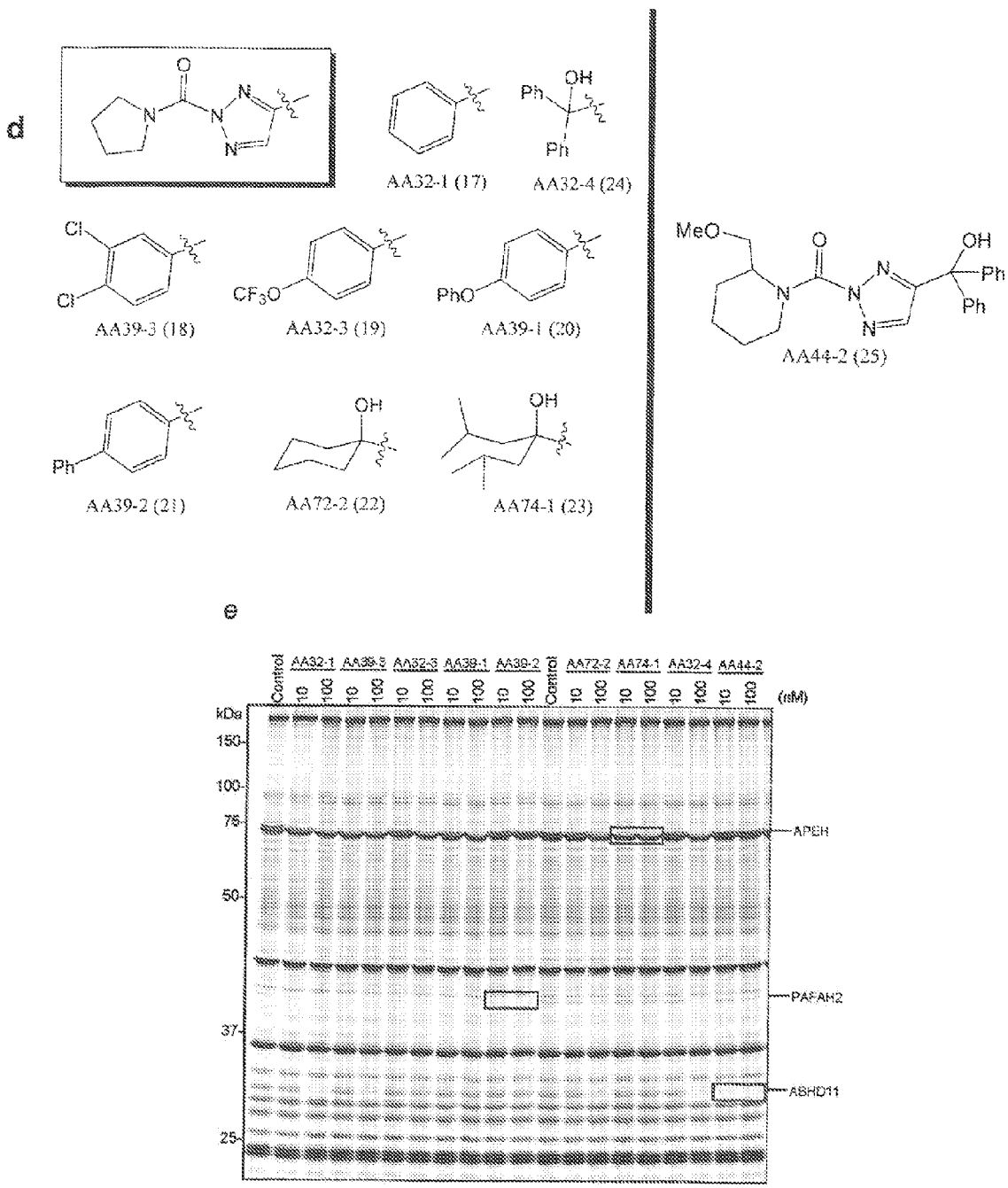

Synthesis of Triazole Urea Inhibitors (See FIG. 3 and FIG. 12 for Inhibitor Structures)

An additional series of triazole urea compounds was prepared to further evaluate enzyme selectivity of the inhibitors.

Ex. 5(A)

2-(Methoxymethyl)piperidinecarbonyl chloride 2-(Methoxymethyl)piperidinecarbonyl chloride was synthesized from 2-(Methoxymethyl)piperidine following the General Procedure 1. All other carbamoyl chlorides were purchased from Sigma-Aldrich.

Ex. 5(B)

AA26-1 (8)

Following the General Procedure 3, dimethylcarbamoyl chloride (108 mg, 1 mmol) was reacted with NH-1,2,3-triazole (83 mg, 1.2 mmol) to obtain AA26-1 (129 mg, 0.92 mmol, 92%). $^1$H-NMR (400 MHz, CDCl$_3$): δ=7.83 (s, 1H), 7.73 (s, 1H), 3.36 (s, 3H), 3.23 (s, 3H). HRMS (m/z): calcd for $C_5H_9N_4O$ $[M+H]^+$: 141.0771. found: 141.0774.

Ex. 5(C)

AA26-2 (9)

Following the General Procedure 3, diethylcarbamoyl chloride (136 mg, 1 mmol) was reacted with NH-1,2,3-triazole (83 mg, 1.2 mmol) to obtain AA26-2 (157 mg, 0.94 mmol, 94%). $^1$H-NMR (400 MHz, CDCl$_3$): δ=7.81 (s, 1H), 7.73 (s, 1H), 3.59 (s, 4H), 1.33 (m, 6H). HRMS (m/z): calcd for $C_7H_{13}N_4O$ [M+H]$^+$: 169.1084. found: 169.1086.

Ex. 5(D)

AA26-3 (10)

Following the General Procedure 3, diphenylcarbamoyl chloride (232 mg, 1 mmol) was reacted with NH-1,2,3-triazole (83 mg, 1.2 mmol) to obtain AA26-3 (230 mg, 0.87 mmol, 87%). $^1$H-NMR (400 MHz, CDCl$_3$): δ=7.60 (s, 1H), 7.57 (s, 1H), 7.36-7.16 (m, 10H). HRMS (m/z): calcd for $C_{15}H_{13}N_4O$ [M+H]$^+$: 265.1084. found: 265.1087.

Ex. 5(E)

AA26-4 (11)

Following the General Procedure 3, 4-methyl-1-piperazinecarbonyl chloride (199 mg, 1 mmol) was reacted with NH-1,2,3-triazole (83 mg, 1.2 mmol) to obtain AA26-4 (135 mg, 0.69 mmol, 69%). $^1$H-NMR (400 MHz, CDCl$_3$): δ=7.65 (s, 1H), 7.50 (s, 1H), 3.77-3.63 (m, 4H), 2.47 (m, 7H). HRMS (m/z): calcd for $C_8H_{14}N_5O$ [M+H]$^+$: 196.1193. found: 196.1195.

Ex. 5(F)

AA26-5 (12)

Following the General Procedure 3, 4-morpholinecarbonyl chloride (150 mg, 1 mmol) was reacted with NH-1,2,3-triazole (83 mg, 1.2 mmol) to obtain AA26-5 (171 mg, 0.94 mmol, 94%). $^1$H-NMR (400 MHz, CDCl$_3$): δ=7.84 (s, 1H), 7.75 (s, 1H), 4.02-3.80 (m, 8H). HRMS (m/z): calcd for $C_7H_{1N14}O_2$ [M+H]$^+$: 183.0877. found: 183.0877.

Ex. 5(G)

AA26-6 (13)

Following the General Procedure 3, carbazole-9-carbonyl chloride (230 mg, 1 mmol) was reacted with NH-1,2,3-triazole (83 mg, 1.2 mmol) to obtain AA26-6 (212 mg, 0.81 mmol, 81%). $^1$H-NMR (400 MHz, CDCl$_3$): δ=8.09-8.05 (m, 4H), 7.41-7.22 (m, 6H). HRMS (m/z): calcd for $C_{15}H_{1N14}O_2$ [M+H]$^+$: 263.0927. found: 263.0930.

Ex. 5(H)

AA26-7 (14)

Following the General Procedure 3, N-methyl-N-phenylcarbamoyl chloride (170 mg, 1 mmol) was reacted with NH-1,2,3-triazole (83 mg, 1.2 mmol) to obtain AA26-7 (175 mg, 0.86 mmol, 86%). $^1$H-NMR (400 MHz, CDCl$_3$): δ=7.53-7.47 (bs, 4H), 7.28-6.99 (m, 3H), 3.50 (s, 3H). HRMS (m/z): calcd for $C_{10}H_{1N14}O$ [M+H]$^+$: 203.0927. found: 203.0922.

Ex. 5(I)

AA26-8 (15)

Following the General Procedure 3, 1-pyrrolidinecarbonyl chloride (134 mg, 1 mmol) was reacted with NH-1,2,3-triazole (83 mg, 1.2 mmol) to obtain AA26-8 (153 mg, 0.92 mmol, 92%). $^1$H-NMR (400 MHz, CDCl$_3$): δ=7.83 (s, 1H), 7.73 (s, 1H), 3.76 (m, 4H), 2.03-1.99 (m, 4H). HRMS (m/z): calcd for $C_7H_{1N14}O$ [M+H]$^+$: 167.0927. found: 167.0932.

Ex. 5(J)

AA26-9 (7)

Following the General Procedure 3, 1-piperidinecarbonyl chloride (148 mg, 1 mmol) was reacted with NH-1,2,3-triazole (83 mg, 1.2 mmol) to obtain AA26-9 (175 mg, 0.97 mmol, 97%). $^1$H-NMR (400 MHz, CDCl$_3$): δ=7.82 (s, 1H), 7.73 (s, 1H), 3.76-3.54 (m, 4H), 1.74-1.57 (m, 6H). HRMS (m/z): calcd for $C_8H_{13}N_4O$ [M+H]$^+$: 181.1084. found: 181.1083.

Ex. 5(K)

AA26-10 (16)

Following the General Procedure 3, diallylcarbamyl chloride (160 mg, 1 mmol) was reacted with NH-1,2,3-triazole (83 mg, 1.2 mmol) to obtain AA26-10 (183 mg, 0.95 mmol, 95%). $^1$H-NMR (400 MHz, CDCl$_3$): δ=7.82 (s, 1H), 7.72 (s, 1H), 5.99-5.89 (m, 2H), 5.27 (m, 4H), 4.27-4.09 (m, 4H). HRMS (m/z): calcd for $C_9H_{13}N_4O$ [M+H]$^+$: 193.1084. found: 193.1082.

Ex. 5(L)

AA32-1 (17)

Following the General Procedure 3, 1-pyrrolidinecarbonyl chloride (40 mg, 0.3 mmol) was reacted with triazole 38 (52 mg, 0.36 mmol) to obtain AA32-1 (62 mg, 0.26 mmol, 87%). $^1$H-NMR (400 MHz, CDCl$_3$): δ=8.08 (s, 1H), 7.90-7.83 (m, 2H), 7.47-7.36 (m, 3H), 4.08 (t, J=6.5 Hz, 1H), 3.95 (t, J=6.5 Hz, 1H), 3.76 (m, 2H), 1.99 (m, 4H). HRMS (m/z): calcd for $C_{13}H_{15}N_4O$ [M+H]$^+$: 243.1240. found: 243.1241.

Ex. 5(M)

AA32-2 (28)

Following the General Procedure 3, 1-pyrrolidinecarbonyl chloride (40 mg, 0.3 mmol) was reacted with triazole 41 (65 mg, 0.36 mmol) to obtain AA32-2 (69 mg, 0.25 mmol, 82%). $^1$H-NMR (400 MHz, CDCl$_3$): δ=8.06 (s, 1H), 7.43-7.06 (m, 2H), 6.68-6.47 (m, 1H), 4.08 (m, 1H), 3.93 (m, 1H), 3.77 (m, 2H), 2.03 (m, 4H). HRMS (m/z): calcd for $C_{13}H_{13}F_2N_4O$ [M+H]$^+$: 279.1052. found: 279.1057.

Ex. 5(N)

AA32-3 (19)

Following the General Procedure 3, 1-pyrrolidinecarbonyl chloride (40 mg, 0.3 mmol) was reacted with triazole 40 (82 mg, 0.36 mmol) to obtain AA32-3 (74 mg, 0.23 mmol, 75%). $^1$H-NMR (400 MHz, CDCl$_3$): δ=7.97 (s, 1H), 7.86-7.76 (m, 2H), 7.21 (m, 2H), 3.99 (t, J=6.2 Hz, 1H), 3.85 (t, J=6.2 Hz, 1H), 3.68 (m, 2H), 1.93 (m, 4H). HRMS (m/z): calcd for $C_{14}H_{14}F_3N_4O_2$ [M+H]$^+$: 327.1063. found: 327.1065.

Ex. 5(O)

AA32-4 (24)

Following the General Procedure 3, 1-pyrrolidinecarbonyl chloride (40 mg, 0.3 mmol) was reacted with triazole 49 (91 mg, 0.36 mmol) to obtain AA32-4 (64 mg, 0.18 mmol, 61%). $^1$H-NMR (400 MHz, CDCl$_3$): δ=7.49 (s, 1H), 7.30-7.18 (m, 10H), 3.97 (t, J=6.4 Hz, 1H), 3.78 (t, J=6.4 Hz, 1H), 3.65 (m, 2H), 1.91 (m, 4H). HRMS (m/z): calcd for C$_{20}$H$_{2N14}$O$_2$ [M+H]$^+$: 349.1659. found: 349.1662.

Ex. 5(P)

AA34-1 (35)

Following the General Procedure 3, 1-morpholinecarbonyl chloride (45 mg, 0.3 mmol) was reacted with triazole 38 (52 mg, 0.36 mmol) to obtain AA34-1 (71 mg, 0.28 mmol, 92%). $^1$H-NMR (400 MHz, CDCl$_3$): δ=8.02 (s, 1H), 7.81-7.73 (m, 2H), 7.42-7.37 (m, 3H), 3.77 (m, 8H). HRMS (m/z): calcd for C$_{13}$H$_{15}$N$_4$O$_2$ [M+H]$^+$: 259.1190. found: 259.1191.

Ex. 5(Q)

AA34-2 (36)

Following the General Procedure 3, 1-morpholinecarbonyl chloride (45 mg, 0.3 mmol) was reacted with triazole 41 (65 mg, 0.36 mmol) to obtain AA34-2 (77 mg, 0.26 mmol, 87%). $^1$H-NMR (400 MHz, CDCl$_3$): δ=8.01 (s, 1H), 7.33 (m, 2H), 6.80-6.73 (m, 1H), 3.78 (m, 8H). HRMS (m/z): calcd for C$_{13}$H$_{13}$F$_2$N$_4$O$_2$ [M+H]$^+$: 295.1001. found: 295.1007.

Ex. 5(R)

AA34-3 (37)

Following the General Procedure 3, 1-morpholinecarbonyl chloride (45 mg, 0.3 mmol) was reacted with triazole 40 (82 mg, 0.36 mmol) to obtain AA34-3 (85 mg, 0.25 mmol, 82%). $^1$H-NMR (400 MHz, CDCl$_3$): δ=8.01 (s, 1H), 7.85-7.76 (m, 2H), 7.23 (m, 2H), 3.78 (m, 8H). HRMS (m/z): calcd for C$_{14}$H$_{14}$F$_3$N$_4$O$_3$ [M+H]$^+$: 343.1013. found: 343.1018.

Ex. 5(S)

AA39-1 (20)

Following the General Procedure 3, 1-pyrrolidinecarbonyl chloride (40 mg, 0.3 mmol) was reacted with triazole 43 (85 mg, 0.36 mmol) to obtain AA39-1 (82 mg, 0.25 mmol, 82%). $^1$H-NMR (400 MHz, CDCl$_3$): δ=8.01 (s, 1H), 7.93-7.62 (m, 4H), 7.35-7.09 (m, 5H), 4.04 (m, 1H), 3.89 (m, 1H), 3.72 (m, 2H), 1.96 (m, 4H). HRMS (m/z): calcd for C$_{19}$H$_{19}$N$_4$O$_2$ [M+H]$^+$: 335.1503. found: 335.1507.

Ex. 5(T)

AA39-2 (21)

Following the General Procedure 3, 1-pyrrolidinecarbonyl chloride (40 mg, 0.3 mmol) was reacted with triazole 44 (80 mg, 0.36 mmol) to obtain AA39-2 (83 mg, 0.26 mmol, 87%) as a 2:1 mixture of N2-carbamoyl and N1-carbamoyl regioisomers, respectively.

5(T)(a). AA39-2 (1,4-Isomer; N1-Carbamoyl).

R$_f$ value: 0.7 in Hex/EtOAc 1:1. $^1$H-NMR (400 MHz, CDCl$_3$): δ=8.53 (s, 1H), 7.86-7.41 (m, 9H), 4.04 (m, 1H), 3.97 (m, 1H), 3.75 (m, 2H), 1.98 (m, 4H). $^{13}$C-NMR (100 MHz, CDCl$_3$): δ=154.5, 145.2, 142.7, 139.4, 129.8, 129.5, 128.8, 128.4, 127.6, 127.3, 120.2, 53.3, 26.8. HRMS (m/z): calcd for C$_{19}$H$_{19}$N$_4$O [M+H]$^+$: 319.1553. found: 319.1551.

5(T)(b). AA39-2 (2,4-Isomer; N2-Carbamoyl):

Rf value 0.6 in Hex/EtOAc 1:1. $^1$H-NMR (400 MHz, CDCl$_3$): δ=8.10 (s, 1H), 7.90-7.29 (m, 9H), 4.07 (m, 1H), 3.94 (m, 1H), 3.73 (m, 2H), 2.01 (m, 4H). $^{13}$C-NMR (100 MHz, CDCl$_3$): δ=154.4, 146.3, 141.1, 140.9, 129.6, 129.4, 128.5, 128.4, 127.8, 127.5, 121.4, 53.7, 25.3. HRMS (m/z): calcd for C$_{19}$H$_{19}$N$_4$O [M+H]$^+$: 319.1553. found: 319.1556.

Ex. 5(U)

AA39-3 (18)

Following the General Procedure 3, 1-pyrrolidinecarbonyl chloride (40 mg, 0.3 mmol) was reacted with triazole 39 (77 mg, 0.36 mmol) to obtain AA39-3 (85 mg, 0.27 mmol, 91%). $^1$H-NMR (400 MHz, CDCl$_3$): δ=8.02 (s, 1H), 7.65-7.34 (m, 2H), 7.17-7.01 (m, 1H), 4.12 (m, 1H), 3.96 (m, 1H), 3.82 (m, 2H), 2.05 (m, 4H). HRMS (m/z): calcd for C$_{13}$H$_{13}$Cl$_2$N$_4$O [M+H]$^+$: 311.0461. found: 311.0463.

Ex. 5(V)

AA39-4 (29)

Following the General Procedure 3, 1-pyrrolidinecarbonyl chloride (40 mg, 0.3 mmol) was reacted with triazole 42 (68 mg, 0.36 mmol) to obtain AA39-4 (71 mg, 0.25 mmol, 83%). $^1$H-NMR (400 MHz, CDCl$_3$): δ=8.15 (s, 1H), 7.85-7.56 (m, 2H), 7.51-7.37 (m, 2H), 4.14 (m, 1H), 3.97 (m, 1H), 3.84 (m, 2H), 2.05 (m, 4H). HRMS (m/z): calcd for C$_{13}$H$_{14}$N$_5$O$_3$ [M+H]$^+$: 288.1091. found: 288.1092.

Ex. 5(W)

AA39-5 (30)

Following the General Procedure 3, 1-pyrrolidinecarbonyl chloride (40 mg, 0.3 mmol) was reacted with triazole 45 (81 mg, 0.36 mmol) to obtain AA39-5 (74 mg, 0.23 mmol, 77%). $^1$H-NMR (400 MHz, CDCl$_3$): δ=8.15 (m, 1H), 8.04 (s, 1H), 7.91-7.67 (m, 3H), 7.33-7.04 (m, 2H), 4.05 (m, 1H), 3.89 (m, 1H), 3.81 (s, 3H), 3.71 (m, 2H), 1.95 (m, 4H). HRMS (m/z): calcd for C$_{18}$H$_{19}$N$_4$O$_2$ [M+H]$^+$: 323.1503. found: 323.1500.

Ex. 5(X)

AA40-2 (32)

Following the General Procedure 3, 1-piperidinecarbonyl chloride (44 mg, 0.3 mmol) was reacted with triazole 43 (85 mg, 0.36 mmol) to obtain AA40-2 (92 mg, 0.26 mmol, 88%). $^1$H-NMR (400 MHz, CDCl$_3$): δ=8.03 (s, 1H), 7.91-7.64 (m, 4H), 7.36-7.12 (m, 5H), 3.74-3.57 (m, 4H), 1.77-1.59 (m, 6H). HRMS (m/z): calcd for C$_{20}$H$_{2N14}$O$_2$ [M+H]$^+$: 349.1659. found: 349.1665.

Ex. 5(Y)

AA40-3 (33)

Following the General Procedure 3, 1-piperidinecarbonyl chloride (44 mg, 0.3 mmol) was reacted with triazole 45 (81 mg, 0.36 mmol) to obtain AA40-3 (81 mg, 0.24 mmol, 80%). $^1$H-NMR (400 MHz, CDCl$_3$): δ=8.12 (m, 1H), 7.99 (s, 1H), 7.90-7.63 (m, 3H), 7.32-7.13 (m, 2H), 3.82 (s, 3H), 3.72-3.58

(m, 4H), 1.74-1.55 (m, 6H). HRMS (m/z): calcd for $C_{19}H_{2N14}O_2$ [M+H]$^+$: 337.1659. found: 337.1656.

Ex. 5(Z)

AA44-2 (25)

Following the General Procedure 3, crude 2-(methoxymethyl) piperidinecarbonyl chloride (153 mg, 0.8 mmol) was reacted with triazole 49 (241 mg, 0.96 mmol) to obtain AA44-2 (140 mg, 0.34 mmol, 43% over 2 steps) as a 3:1 mixture of N2-carbamoyl and N1-carbamoyl regioisomers, respectively.

5(Z)(a). AA44-2 (1,4-Isomer):
$R_f$ value: 0.6 in Hex/EtOAc 1:1. $^1$H-NMR (400 MHz, CDCl$_3$): δ=7.77 (s, 1H), 7.45-7.36 (m, 10H), 3.58-3.02 (m, 8H), 1.19-0.93 (m, 6H). $^{13}$C-NMR (100 MHz, CDCl$_3$): δ=151.8, 146.4, 134.6, 130.2, 128.3, 126.7, 123.3, 91.2, 76.6, 60.5, 60.3, 49.3, 26.9, 25.7, 23.1. HRMS (m/z): calcd for $C_{23}H_{27}N_4O_3$ [M+H]$^+$: 407.2078. found: 407.2080.

5(Z)(b). AA44-2 (2,4-Isomer):
$R_f$ value: 0.5 in Hex/EtOAc 1:1. $^1$H-NMR (400 MHz, CDCl$_3$): δ=7.55 (s, 1H), 7.30-7.21 (m, 10H), 3.70-3.22 (m, 8H), 1.26-1.04 (m, 6H). $^{13}$C-NMR (100 MHz, CDCl$_3$): δ=152.5, 144.2, 131.2, 128.5, 127.1, 126.4, 123.1, 90.7, 74.4, 60.8, 60.5, 48.1, 27.6, 25.9, 23.4. HRMS (m/z): calcd for $C_{23}H_{27}N_4O_3$ [M+H]$^+$: 407.2078. found: 407.2083.

Ex. 5(AA) AA47-1 (34)

Following the General Procedure 3, 1-piperidinecarbonyl chloride (44 mg, 0.3 mmol) was reacted with triazole 50 (63 mg, 0.36 mmol) to obtain AA47-1 (64 mg, 0.23 mmol, 75%). δ=7.63 (s, 1H), 7.40-7.23 (m, 5H), 6.91 (d, J=3.4 Hz, 1H), 3.68-3.35 (m, 4H), 1.62-1.46 (m, 6H). HRMS (m/z): calcd for $C_{15}H_{19}N_4O_2$ [M+H]$^+$: 287.1503. found: 287.1506.

Ex. 5(AB)

AA72-1 (31)

Following the General Procedure 3, 1-pyrrolidinecarbonyl chloride (67 mg, 0.5 mmol) was reacted with triazole 46 (76 mg, 0.6 mmol) to obtain AA72-1 (78 mg, 0.35 mmol, 70%). $^1$H-NMR (400 MHz, CDCl$_3$): δ=7.46 (s, 1H), 3.89 (t, J=6.0 Hz, 1H), 3.80 (t, J=6.0 Hz, 1H), 3.64 (m, 2H), 1.89 (m, 4H), 1.53 (bs, 6H). HRMS (m/z): calcd for $C_{10}H_{17}N_4O_2$ [M+H]$^+$: 225.1346. found: 225.1341.

Ex. 5(AC)

AA72-2 (22)

Following the General Procedure 3, 1-pyrrolidinecarbonyl chloride (67 mg, 0.5 mmol) was reacted with triazole 47 (100 mg, 0.6 mmol) to obtain AA72-2 (77 mg, 0.29 mmol, 58%). δ=7.56 (s, 1H), 3.99 (t, J=6.1 Hz, 1H), 3.86 (t, J=6.1 Hz, 1H), 3.71 (m, 2H), 2.04-1.34 (m, 14H). HRMS (m/z): calcd for $C_{13}H_{2N14}O_2$ [M+H]$^+$: 265.1659. found: 265.1661.

Ex. 5(AD)

AA74-1 (23)

Following the General Procedure 3, 1-pyrrolidinecarbonyl chloride (67 mg, 0.5 mmol) was reacted with triazole 48 (127 mg, 0.6 mmol) to obtain AA74-1 (98 mg, 0.32 mmol, 64%) as a 3:1 mixture of 2,4 and 1,4 regioisomers.

5(AD)(a). AA74-1 (1,4-Isomer):
$R_f$ value: 0.7 in Hex/EtOAc 1:2. $^1$H-NMR (400 MHz, CDCl$_3$): δ=8.16 (s, 1H), 4.05 (m, 1H), 3.92 (m, 1H), 3.82 (m, 2H), 2.07-1.89 (m, 10H), 1.01 (s, 3H), 0.99 (s, 3H), 0.80 (s, 3H), 0.79 (s, 3H). $^{13}$C-NMR (100 MHz, CDCl$_3$): δ=154.1, 127.5, 125.6, 77.7, 58.2, 50.9, 26.7, 25.5, 23.8. HRMS (m/z): calcd for $C_{16}H_{29}N_4O_2$ [M+H]$^+$: 309.2285. found: 309.2287.

5(AD)(b). AA74-1 (2,4-Isomer):
$R_f$ value: 0.6 in Hex/EtOAc 1:2. $^1$H-NMR (400 MHz, CDCl$_3$): δ=7.71 (s, 1H), 4.03 (t, J=6.5 Hz, 1H), 3.83 (t, J=6.5 Hz, 1H), 3.73 (m, 2H), 2.04-1.77 (m, 10H), 0.93 (s, 3H), 0.91 (s, 3H), 0.72 (s, 3H), 0.71 (s, 3H). $^{13}$C-NMR (100 MHz, CDCl$_3$): δ=155.3, 127.2, 123.8, 74.9, 52.8, 52.1, 25.6, 24.5, 24.2. HRMS (m/z): calcd for $C_{16}H_{29}N_4O_2$ [M+H]$^+$: 309.2285. found: 309.2291.

Ex. 5(AE)

AA80-1

Following the General Procedure 3, 1-pyrrolidinecarbonyl chloride (200 mg, 1.5 mmol) was reacted with 4-bromophenyl triazole (403 mg, 1.8 mmol) to obtain AA80-1 (390 mg, 1.21 mmol, 81%) as a 1.7:1 mixture of 2,4 and 1,4 regioisomers.

5(AE)(a). AA80-1 (1,4-Isomer):
$R_f$ value: 0.7 in Hex/EtOAc 1:1. $^1$H-NMR (400 MHz, CDCl$_3$): δ=8.49 (s, 1H), 7.77-7.57 (m, 4H), 4.06 (m, 2H), 3.75 (m, 2H), 2.02 (m, 4H). $^{13}$C-NMR (100 MHz, CDCl$_3$): δ=154.8, 146.3, 132.4, 129.5, 128.2, 128.0, 122.3, 54.6, 25.9. HRMS (m/z): calcd for $C_{13}H_{13}BrN_4O$ [M+H]$^+$: 321.0346. found: 321.0351. The regiochemistry of this isomer was determined by single crystal X-ray crystalography.

5(AE)(b). AA80-1 (2,4-Isomer):
$R_f$ value: 0.6 in Hex/EtOAc 1:1. $^1$H-NMR (400 MHz, CDCl$_3$): δ=8.04 (s, 1H), 7.76-7.58 (m, 4H), 3.91 (m, 2H), 3.76 (m, 2H), 2.00 (m, 4H). $^{13}$C-NMR (100 MHz, CDCl$_3$): δ=154.9, 148.2, 132.2, 129.1, 128.7, 128.3, 122.2, 55.1, 25.6. HRMS (m/z): calcd for $C_{13}H_{13}BrN_4O$ [M+H]$^+$: 321.0346. found: 321.0345.

Ex. 5(AF)

KT117

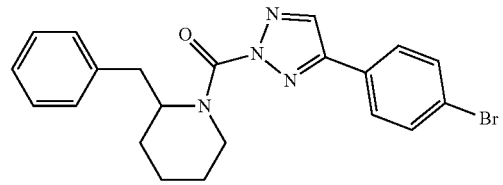

KT117

Following the General Procedure 3, 2-benzylpiperidinecarbonyl chloride (200 mg, 1.5 mmol) was reacted with 4-bromophenyl triazole (403 mg, 1.8 mmol), and the (2,4-isomer) was separated and characterized: $R_f$ value: 0.5 in Hex/EtOAc 2:1. $^1$H-NMR (400 MHz, CDCl$_3$): δ=8.01 (s, 1H), 7.74-7.57 (m, 4H), 7.29-7.07 (m, 5H), 4.61 (bs, 2H), 3.30 (m, 1H), 3.18 (m, 1H), 3.02 (m, 1H), 1.91-1.61 (m, 6H). $^{13}$C-NMR (100 MHz, CDCl$_3$): δ=150.1, 148.3, 138.4, 131.2, 129.5, 128.5, 128.3, 127.0, 123.9, 59.5, 51.1, 36.4, 27.1, 26.9, 25.9. HRMS (m/z): calcd for $C_{21}H_{21}BrN_4O$ [M+H]$^+$: 425.0972. found: 425.0975. The regiochemistry of this isomer was determined by single crystal X-ray crystalography.

Example 6

Synthesis of Compounds for DAGL Inhibition Studies (See FIG. 21 for Structures)

Several triazole urea materials were prepared for investigation of DAGL selectivity. Unless otherwise specified, chromatographic separations were performed using silica gel column chromatography in which the amount of silica gel is specified in grams, or using preparative silica gel thin layer chromatography (pTLC). The solvents used for the chromatographic separations also are specified.

Ex. 6(A)

KT116

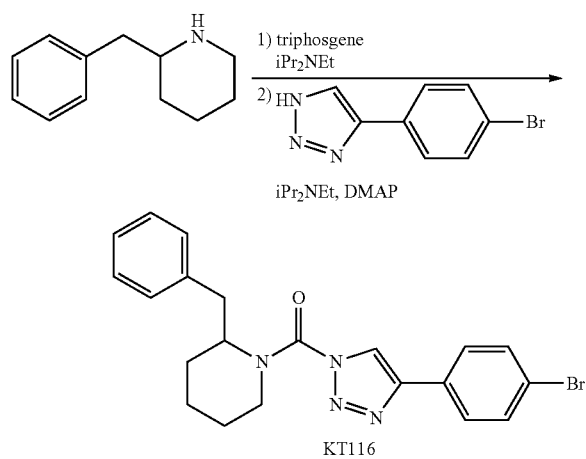

A solution of 2-benzyl piperidine (0.32 g, 1.8 mmol) in THF (15 mL) was treated with iPr$_2$NEt (0.95 mL, 5.4 mmol) and triphosgene (0.27 g, 0.9 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The intermediate was dissolved in THF (20 mL), and iPr$_2$NEt (0.95 mL, 5.4 mmol), DMAP (218 mg, 1.8 mmol) and 4-(4-bromophenyl)-1H-1,2,3-triazole (0.40 g, 1.8 mmol) were added to the solution. The mixture was stirred for 2 h at 60° C. and poured into saturated aqueous NH$_4$Cl solution. The mixture was extracted with ethyl acetate, washed with H$_2$O and brine, dried over Na$_2$SO$_4$ and concentrated under reduced pressure. Chromatography (70 g; ethyl acetate:hexane=1:6-1:5) afforded the 1,4-triazole urea KT116 (320 mg, 42%) as a top spot. $^1$H NMR (CDCl$_3$, 400 MHz) δ=7.72-7.54 (m, 4H), 7.45-6.89 (m, 6H), 5.29 (br, 1H), 4.34 (brd, 1H, J=13.5 Hz), 3.42-3.10 (m, 2H), 2.67 (br, 1H), 2.04-1.60 (m, 6H). $^{13}$C NMR (CDCl$_3$, 150 MHz) δ=150.95, 146.21, 138.82, 132.96, 130.02, 129.57, 129.53, 128.11, 127.43, 123.33, 121.44, 58.25, 41.77, 37.49, 29.79, 26.18, 19.73. HRMS calculated for $C_2H_{22}BrN_4O$ [M+H]$^+$ 425.0971. found 425.0976.

Ex. 6(B)

KT109

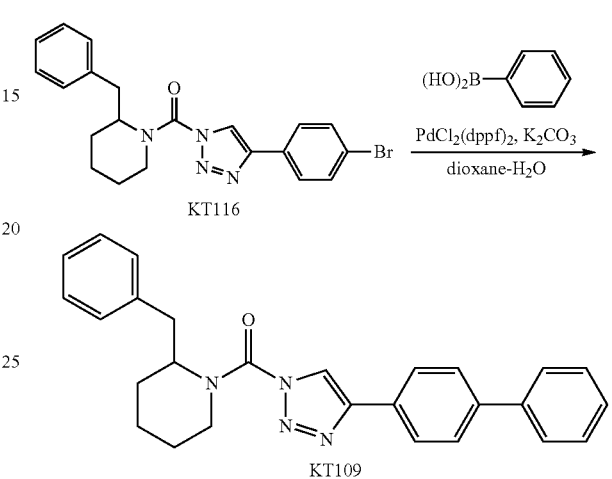

A solution of KT116 (30 mg, 0.071 mmol) in dioxane (2 mL) and H$_2$O (0.1 mL) was treated with phenyl boronic acid (16 mg, 0.13 mmol), K$_2$CO$_3$ (30 mg, 0.22 mmol) and PdCl$_2$(dppf) (8 mg, 0.011 mmol), and the reaction mixture was stirred for 2 h at 80° C. under N$_2$. The mixture was poured into H$_2$O and extracted with ethyl acetate. The organic layer was washed with H$_2$O and brine, dried over Na$_2$SO$_4$ and concentrated under reduced pressure. The residue was purified by pTLC (ethyl acetate:hexane=1:4) to afford KT109 (23 mg, 77%). $^1$H NMR (CDCl$_3$, 400 MHz) δ=7.86 (br, 2H), 7.70-7.65 (m, 4H), 7.50-7.35 (m, 3H), 7.30-6.90 (m, 5H), 4.87 (br, 1H), 4.37 (brd, 1H, J=13.7 Hz), 3.40-3.20 (m, 2H), 2.71 (br, 1H), 2.03-1.65 (m, 6H). $^{13}$C NMR (CDCl$_3$, 150 MHz) δ=150.20, 146.96, 142.13, 141.35, 138.83, 130.04, 129.73, 129.59, 129.51, 128.47, 128.41, 127.88, 127.47, 127.02, 121.36, 58.26, 41.80, 37.51, 29.66, 26.24, 19.75. HRMS calculated for $C_{27}H_{27}N_4O$ [M+H]$^+$ 423.2179. found 423.2178.

Ex. 6(C)

KT172

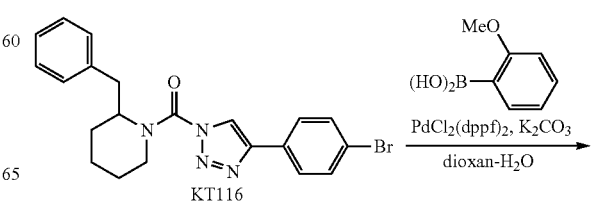

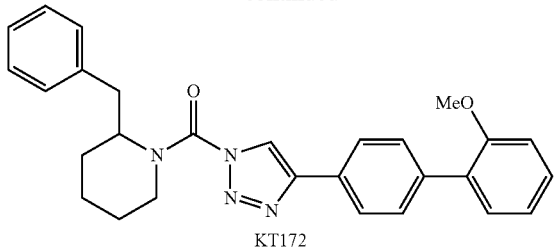

KT172

A solution of KT116 (30 mg, 0.071 mmol) in dioxane (2 ml) and H₂O (0.1 mL) was treated with phenyl boronic acid (17 mg, 0.13 mmol), K₂CO₃ (30 mg, 0.22 mmol) and PdCl₂(dppf) (8 mg, 0.011 mmol), and the reaction mixture was stirred for 2 h at 80° C. under N₂. The mixture was poured into H₂O and extracted with ethyl acetate. The organic layer was washed with H₂O and brine, dried over Na₂SO₄ and concentrated under reduced pressure. The residue was purified by pTLC (ethyl acetate:hexane=1:4) to afford KT172 (27 mg, 85%). ¹H NMR (CDCl₃, 400 MHz) δ=7.84 (br, 2H), 7.63 (d, 2H, J=8.4 Hz), 7.50-6.95 (m, 9H), 4.87 (br, 1H), 4.37 (brd, 1H, J=13.8 Hz), 3.42-3.10 (m, 2H), 2.71 (br, 1H), 2.03-1.65 (m, 6H). ¹³C NMR (CDCl₃, 150 MHz) δ=157.36, 150.25, 147.20, 138.82, 131.61, 130.92, 130.87, 130.03, 129.75, 129.59, 129.10, 127.49, 126.29, 121.78, 112.13, 58.21, 56.46, 41.79, 37.47, 29.69, 26.25, 19.76. HRMS calculated for C₂₈H₂₉N₄O₂ [M+H]⁺ 453.2285. found 453.2297.

Ex. 6(D)

KT179

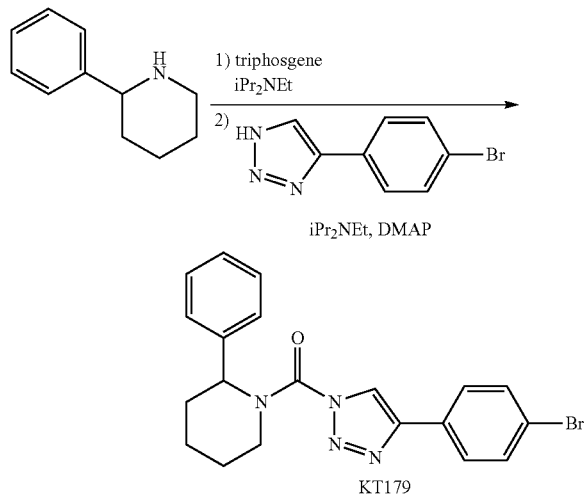

A solution of 2-benzyl piperidine (0.42 g, 2.6 mmol) in THF (8 mL) was treated with iPr₂NEt (1.4 mL, 7.8 mmol) and triphosgene (0.39 g, 1.3 mmol), and the reaction mixture was stirred for 30 min at 4° C. The mixture was poured into H₂O and extracted ethyl acetate. The organic layer was washed with H₂O and brine, dried over Na₂SO₄ and concentrated under reduced pressure. The intermediate was dissolved in THF (10 mL), and iPr₂NEt (1.4 mL, 7.8 mmol), DMAP (0.32 g, 2.6 mmol) and 4-(4-bromophenyl)-1H-1,2,3-triazole (0.60 g, 2.6 mmol) were added to the solution. The mixture was stirred for 2 h at 60° C. and poured into saturated aqueous NH₄Cl solution. The mixture was extracted with ethyl acetate, washed with H₂O and brine, dried over Na₂SO₄ and concentrated under reduced pressure. Chromatography (60 g; ethyl acetate:hexane=1:6) afforded 1,4-triazole urea KT179 (450 mg, 42%) as a top spot. ¹H NMR (CDCl₃, 400 MHz) δ=8.40 (s, 1H), 7.75 (d, 2H, J=8.5 Hz), 7.58 (d, 2H, J=8.5 Hz), 7.43-7.26 (m, 5H), 5.91 (br, 1H), 4.36 (brd, 1H, J=13.6 Hz), 3.18 (m, 1H), 2.52 (brd, 1H, J=14.2 Hz), 2.15 (m, 1H), 1.90-1.60 (m, 4H). ¹³C NMR (CDCl₃, 150 MHz) δ=150.15, 146.74, 138.66, 133.03, 129.85, 129.41, 128.27, 128.08, 127.42, 123.55, 122.01, 28.68, 26.67, 20.16. HRMS calculated for C₂₀H₂₀BrN₄O [M+H]⁺ 411.0815. found 411.0802.

Ex. 6(E)

KT195

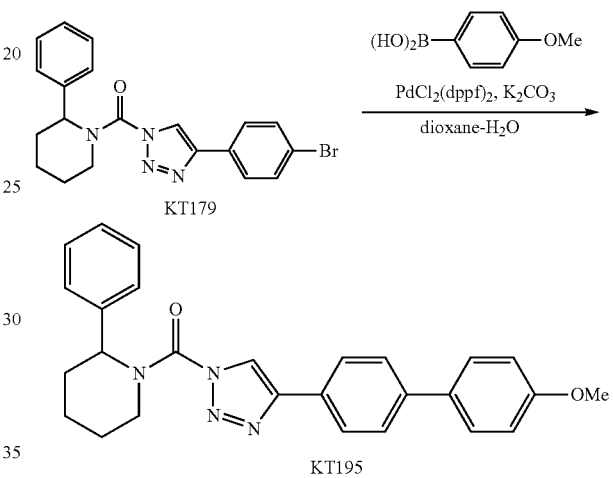

A solution of KT179 (100 mg, 0.24 mmol) in dioxane (4 mL) and H₂O (0.4 mL) was treated with 4-methoxyphenyl boronic acid (55 mg, 0.37 mmol), K₂CO₃ (100 mg, 0.72 mmol) and PdCl₂(dppf) (18 mg, 0.024 mmol), and the reaction mixture was stirred for 2 h at 80° C. under N₂. The mixture was poured into H₂O and extracted with ethyl acetate. The organic layer was washed with H₂O and brine, dried over Na₂SO₄ and concentrated under reduced pressure. Chromatography (50 g; ethyl acetate:hexane=1:5-1:4) afforded KT195 (70 mg, 66%). ¹H NMR (CDCl₃, 400 MHz) δ=8.42 (s, 1H), 7.93 (d, 2H, J=8.3 Hz), 7.65 (d, 2H, J=8.3 Hz), 7.58 (d, 2H, J=8.8 Hz), 7.43-7.26 (m, 5H), 7.00 (d, 2H, J=8.8 Hz), 5.94 (br, 1H), 4.78 (brd, 1H, J=13.8 Hz), 3.19 (brt, 1H, J=13.8 Hz), 2.54 (brd, 1H, J=13.8 Hz), 2.16 (m, 1H), 1.91-1.60 (m, 4H). ¹³C NMR (CDCl₃, 150 MHz) δ=160.24, 150.34, 147.54, 141.91, 138.76, 133.80, 129.84, 128.91, 128.75, 128.04, 128.02, 127.46, 127.15, 121.71, 115.16, 56.24, 28.69, 26.70, 20.20. HRMS calculated for C₂₇H₂₇N4O₂ [M+H]⁺ 439.2128. found 439.2128.

Ex. 6(F)

HT01

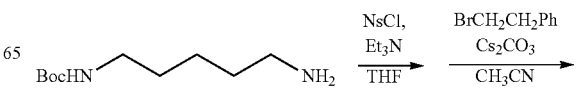

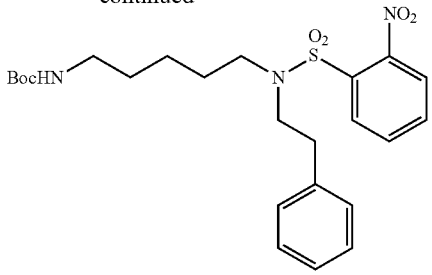

A solution of N-Boc-cadaverine (0.50 g, 2.48 mmol) in THF (10 mL) was treated with o-nitrophenylsulfonyl chloride (0.55 g, 2.48 mmol) and Et$_3$N (0.51 mL, 3.71 mmol), and the mixture was stirred for 1 h at room temperature. The mixture was poured into H$_2$O and extracted with ethyl acetate. The organic layer was washed with H$_2$O and brine, dried over Na$_2$SO$_4$ and concentrated under reduced pressure. The residue was dissolved in CH$_3$CN (20 ml), and Cs$_2$CO$_3$ (2.40 g, 7.43 mmol) and phenethylbromide (0.69 g, 3.71 mmol) was added. The mixture was stirred for 2 h at 80° C. The mixture was poured into H$_2$O and extracted with ethyl acetate. The organic layer was washed with H$_2$O and brine, dried over Na$_2$SO$_4$ and concentrated under reduced pressure. Chromatography (50 g; ethyl acetate:hexane=1:2) afforded sulfonamide (1.1 g, 91%). $^1$H NMR (CDCl$_3$, 300 MHz) δ=7.96 (m, 1H), 7.30-7.15 (m, 5H), 4.50 (br, 1H), 3.50 (m, 2H), 3.33 (t, 2H, J=7.5 Hz), 3.07 (q, 2H, J=6.7 Hz), 2.84 (m, 2H), 1.65-1.38 (m, 4H), 1.44 (s, 9H), 1.34-1.20 (m, 2H). $^{13}$C NMR (CDCl$_3$, 100 MHz) δ=156.33, 148.38, 138.39, 133.98, 133.74, 131.96, 131.03, 129.13, 128.97, 127.03, 124.53, 79.48, 49.15, 47.96, 40.63, 35.48, 29.98, 28.79, 28.10, 24.04. HRMS calculated for C$_{24}$H$_{34}$N$_3$O$_6$S [M+H]$^+$ 492.2163. found 492.2169.

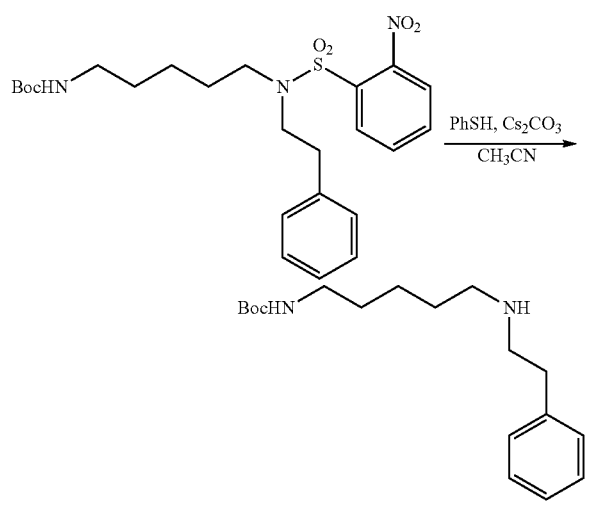

A solution of the sulfonamide (0.70 g, 1.43 mmol) in CH$_3$CN (15 mL) was treated with Cs$_2$CO$_3$ (1.40 g, 4.29 mmol) and benzenethiol (0.22 mL, 2.14 mmol), and the mixture was stirred overnight at room temperature. The mixture was extracted with CH$_2$Cl$_2$, and the organic layer was dried over Na$_2$SO$_4$ and concentrated under reduced pressure. Chromatography (30 g; CH$_2$Cl$_2$/MeOH 10/1—CH$_2$Cl$_2$/MeOH/nPrNH$_2$=100/10/5) afforded amine (0.30 g, 69%). $^1$H NMR (CDCl$_3$, 300 MHz) δ=7.33-7.17 (m, 5H), 4.56 (br, 1H), 2.93-2.80 (m, 4H), 2.64 (t, 2H, J=7.3 Hz), 2.43 (br, 1H), 1.57-1.40 (m, 4H), 1.43 (s, 9H), 1.37-1.25 (m, 2H). $^{13}$C NMR (CDCl$_3$, 100 MHz) 156.36, 140.23, 129.06, 128.84, 126.55, 79.38, 51.42, 49.92, 40.83, 36.49, 30.28, 29.81, 29.80, 24.86. HRMS calculated for C$_{18}$H$_{31}$N$_2$O$_2$ [M+H]$^+$ 307.2380. found 307.2380.

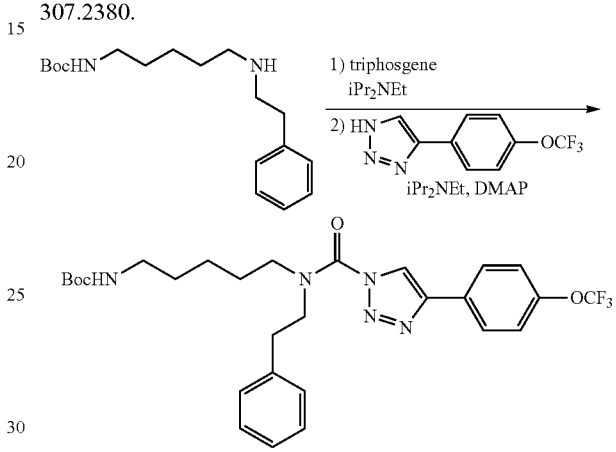

A solution of the amine (78 mg, 0.25 mmol) in THF (3 mL) was treated with iPr$_2$NEt (0.13 mL, 0.76 mmol) and triphosgene (38 mg, 0.13 mmol), and the reaction mixture was stirred for 30 min at 4° C. The mixture was poured into H$_2$O and extracted ethyl acetate. The organic layer was washed with H$_2$O and brine, dried over Na$_2$SO$_4$ and concentrated under reduced pressure. The intermediate was dissolved in THF (4 mL), and iPr$_2$NEt (0.13 mL, 0.76 mmol), DMAP (30 mg, 0.25 mmol) and 4-(4-trifluoromethoxyphenyl)-1H-1,2,3-triazole (57 mg, 0.25 mmol) were added to the solution. The mixture was stirred for 2 h at 60° C. and poured into saturated aqueous NH$_4$Cl solution. The mixture was extracted with ethyl acetate, washed with H$_2$O and brine, dried over Na$_2$SO$_4$ and concentrated under reduced pressure. Chromatography (30 g; ethyl acetate:hexane=1:3) afforded 1,4-triazole urea (51 mg, 37%) as a top spot. $^1$H NMR (CDCl$_3$, 300 MHz) δ=8.41-7.80 (m, 3H), 7.40-7.10 (m, 7H), 4.57 (br, 1H), 4.03-3.50 (m, 4H), 3.20-2.95 (m, 4H), 1.84-1.20 (m, 6H), 1.44 (s, 9H). $^{13}$C NMR (CDCl$_3$, 150 MHz) δ=156.90, 150.16, 146.09, 138.55, 129.78, 129.60, 129.21, 128.37, 128.17, 127.49, 122.32, 122.16, 121.86, 121.30 (q, J=257.5 Hz, OCF$_3$), 80.05, 52.14, 50.05, 41.16, 35.95, 30.66, 29.28, 27.76, 24.84. HRMS calculated for C$_{28}$H$_{35}$F$_3$N$_5$O$_4$ [M+H]$^+$ 562.2636. found 562.2628.

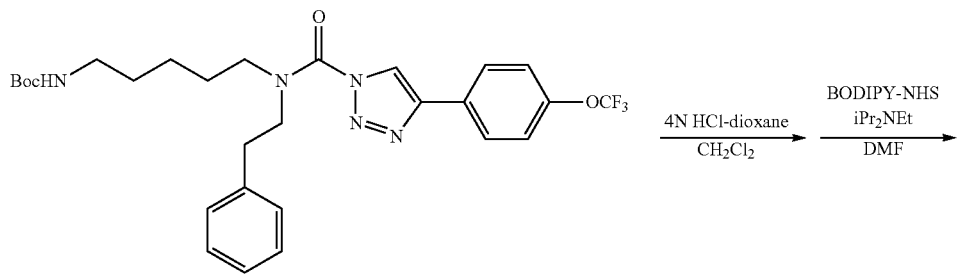

-continued

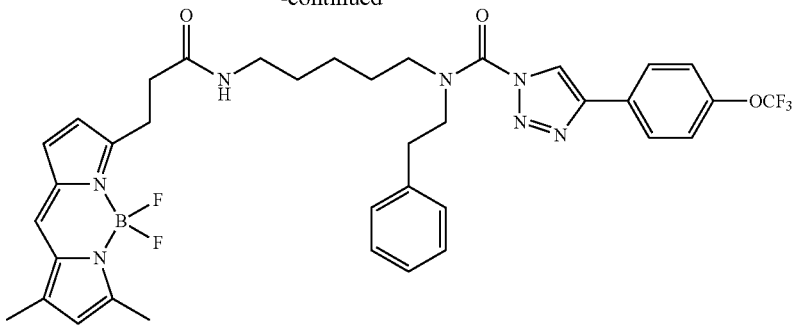

HT01

A solution of the urea (7.2 mg, 12.8 μmmol) in CH$_2$Cl$_2$ (0.5 mL) was treated with 4N HCl-dioxane (0.5 mL), and the mixture was stirred for 3 h at room temperature. The solvent was evaporated and the residue was dissolved in DMF (0.8 mL). iPr$_2$NEt (7 μL, 38.6 umol) and BODIPY-NHS (5.0 mg, 12.8 μmol) was added to the solution, and the mixture was stirred overnight at room temperature. The mixture was poured into H$_2$O and extracted with ethyl acetate. The organic layer was washed with H$_2$O and brine, dried over Na$_2$SO$_4$ and concentrated under reduced pressure. pTLC (ethyl acetate: hexane=3:1) afforded HT01 (6 mg, 64%). $^1$H NMR (CDCl$_3$, 400 MHz) δ=8.42-7.80 (m, 3H), 7.32-7.10 (m, 7H), 7.26 (s, 1H), 6.88 (d, 1H, J=3.9 Hz), 6.28 (br, 1H), 6.10 (s, 1H), 5.84 (br, 1H), 3.96 (br, 1H), 3.72 (m, 1H), 3.59-3.48 (m, 2H), 3.30-2.93 (m, 6H), 2.63 (t, 2H, J=7.5 Hz), 2.50 (s, 3H), 2.23 (s, 3H), 1.78-1.20 (m, 6H). $^{13}$C NMR (CDCl$_3$, 150 MHz) δ=172.56, 161.07, 158.26, 150.14, 146.08, 144.80, 138.56, 135.96, 134.22, 129.78, 129.61, 129.18, 128.16, 127.49, 124.70, 122.90, 122.05, 121.85, 121.31, 121.32 (q, J=257.5 Hz, OCF$_3$), 118.37, 52.10, 49.87, 40.06, 36.90, 35.92, 29.86, 27.67, 25.83, 24.80, 15.81, 12.17. HRMS calculated for C$_{37}$H$_4$OBF$_5$N$_7$O$_3$ [M+H]$^+$ 736.3200. found 736.3204.

Ex. 6(G)

KT182

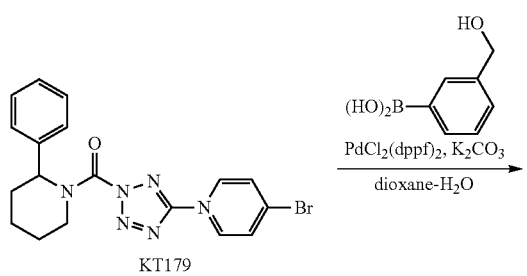

-continued

A solution of urea KT179 (0.70 g, 1.7 mmol) in dioxane (30 ml) and H$_2$O (3 mL) was treated with 3-hydroxymethylphenyl boronic acid (0.39 g, 2.6 mmol), K$_2$CO$_3$ (0.70 g, 5.1 mmol) and PdCl$_2$(dppf) (62 mg, 0.085 mmol), and the reaction mixture was stirred for 2 h at 80° C. under N$_2$. The mixture was poured into H$_2$O and extracted with ethyl acetate. The organic layer was washed with H$_2$O and brine, dried over Na$_2$SO$_4$ and concentrated under reduced pressure. Chromatography (150 g; ethyl acetate:hexane=1:1) afforded KT182 (0.55 g, 74%). $^1$H NMR (CDCl$_3$, 300 MHz) δ=8.44 (s, 1H), 7.96 (d, 2H, J=8.3 Hz), 7.70 (d, 2H, J=8.3 Hz), 7.65 (s, 1H), 7.58 (m, 1H), 7.48-7.25 (m, 7H), 5.93 (br, 1H), 4.78 (br, 2H), 4.38 (brd, 1H, J=13.5 Hz), 3.19 (m, 1H), 2.53 (brd, 1H, J=14.1 Hz), 2.16 (m, 1H), 1.90-1.65 (m, 4H). HRMS calculated for C27H27N4O2 [M+H]$^+$ 439.2128. found 439.2116.

Ex. 6(H)

KT203

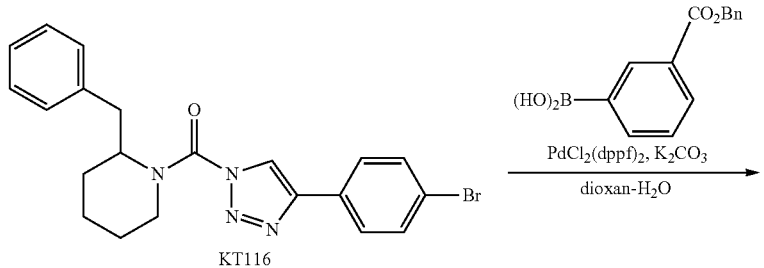

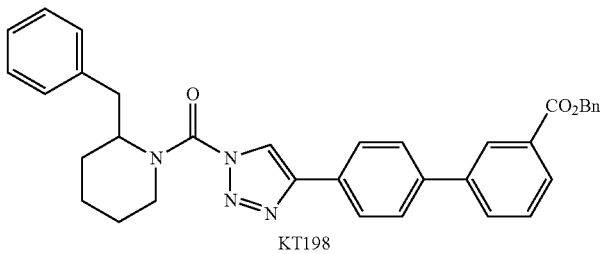

KT198

A solution of urea KT116 (1.2 g, 2.9 mmol) in dioxane (40 ml) and H$_2$O (4 mL) was treated with 3-carboxybenzylphenyl boronic acid (1.1 g, 4.4 mmol), K$_2$CO$_3$ (1.2 g, 8.7 mmol) and PdCl$_2$(dppf) (0.11 g, 0.15 mmol), and the reaction mixture was stirred for 2 h at 80° C. under N$_2$. The mixture was poured into H$_2$O and extracted with ethyl acetate. The organic layer was washed with H$_2$O and brine, dried over Na$_2$SO$_4$ and concentrated under reduced pressure. Chromatography (150 g; ethyl acetate:hexane=1:3) afforded KT198 (1.6 g, quant.). $^1$H NMR (CDCl$_3$, 300 MHz) δ=8.36 (s, 1H), 8.08 (d, 1H, J=7.5 Hz), 7.89 (br, 2H), 7.84 (d, 1H, J=7.3 Hz), 7.71 (d, 2H, J=8.4 Hz), 7.56-7.33 (m, 6H), 7.30-6.90 (m, 5H), 5.42 (s, 2H), 4.86 (br, 1H), 4.37 (d, 1H, J=13.3 Hz), 3.48-2.69 (m, 3H), 2.05-1.65 (m, 6H). HRMS calculated for C$_{35}$H$_{32}$N$_4$O$_3$ [M+H]$^+$ 557.2547. found 557.2552.

A solution of KT198 (1.6 g, 2.9 mmol) in THF (30 mL) was treated with 10% Pd—C (0.30 g) and the mixture was stirred for overnight at room temperature under N$_2$. The mixture was passed through celite and the filtrate was concentrated under reduced pressure. Crystallization from ethyl acetate and hexane afforded KT203 (1.2 g, 89%). $^1$H NMR (CDCl$_3$, 300 MHz) δ=8.41 (s, 1H), 8.12 (d, 1H, J=7.8 Hz), 7.95-7.84 (m, 3H), 7.73 (d, 2H, J=8.3 Hz), 7.59 (t, 1H, J=7.8 Hz), 7.50-6.95 (m, 5H), 5.30 (br, 1H), 4.37 (brd, 1H, J=13.8 Hz), 3.48-2.60 (m, 3H), 2.05-1.65 (m, 6H). HRMS calculated for C$_{28}$H$_{27}$N$_4$O$_3$ [M+H]$^+$ 467.2078. found 467.2077.

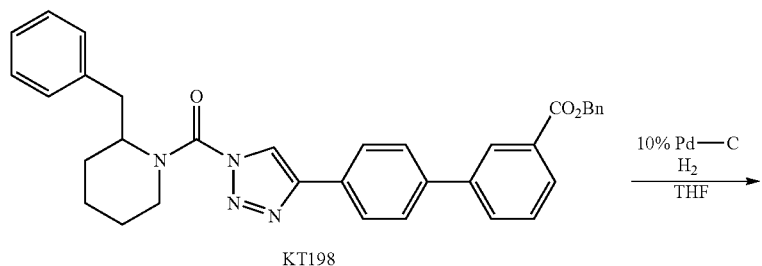

KT198

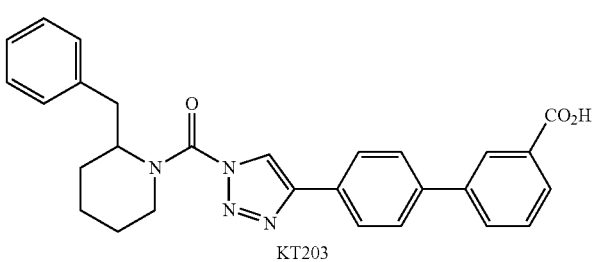

KT203

Ex. 6(I)

KT206

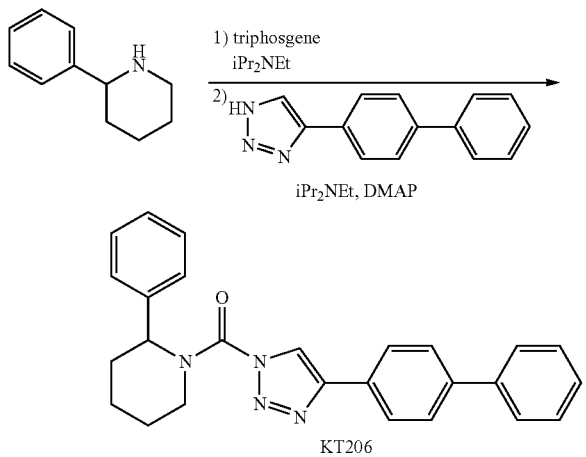

KT206

A solution of 2-phenyl piperidine (1.0 g, 6.2 mmol) in THF (20 mL) was treated with iPr$_2$NEt (3.2 ml, 18.6 mmol) and triphosgene (0.92 g, 3.1 mmol), and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The intermediate was dissolved in THF (30 mL), and iPr$_2$NEt (3.2 mL, 18.6 mmol), DMAP (0.23 g, 1.9 mmol) and 4-([1,1'-biphenyl]-4-yl)-1H-1,2,3-triazole (1.4 g, 6.2 mmol) were added to the solution. The mixture was stirred for 2 h at 60° C. and poured into saturated aqueous NH$_4$Cl solution. The mixture was extracted with ethyl acetate, washed with H$_2$O and brine, dried over Na$_2$SO$_4$ and concentrated under reduced pressure. Chromatography (200 g; ethyl acetate:hexane=1:6-1:5) afforded 1,4-triazole urea KT206 (0.85 g, 34%) as a top spot. $^1$H NMR (CDCl$_3$, 300 MHz) δ=8.44 (s, 1H), 7.96 (d, 2H, J=8.4 Hz), 7.70 (d, 2H, J=8.4 Hz), 7.66-7.63 (m, 2H), 7.48-7.26 (m, 8H), 5.29 (br, 1H), 4.38 (brd, 1H, J=13.7 Hz), 3.19 (m, 1H), 2.54 (brd, 1H, J=14.3 Hz), 2.16 (m, 1H), 1.92-1.63 (m, 4H). HRMS calculated for C$_{26}$H$_{25}$N$_4$O [M+H]$^+$ 409.2023. found 409.2020.

Ex. 6(J)

AA 43-2

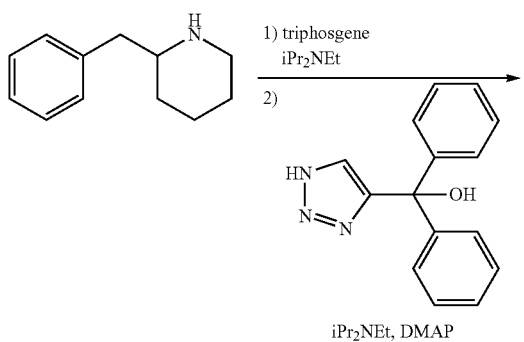

A solution of 2-benzyl piperidine in THF was treated with iPr$_2$NEt and triphosgene, and the reaction mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The intermediate was dissolved in THF, and iPr$_2$NEt, DMAP and hydroxydiphenylmethyl-1H-1,2,3-triazole were added to the solution to afford triazole urea AA43-2. $^1$H NMR (CDCl$_3$, 400 MHz) δ 7.50-6.73 (m, 15H), 4.77 (br, 1H), 4.30 (d, 1H, J=13.5 Hz), 3.59 (s, 1H), 3.41-2.56 (m, 3H), 2.00-1.56 (m, 6H).

Ex. 6(K)

KLH25

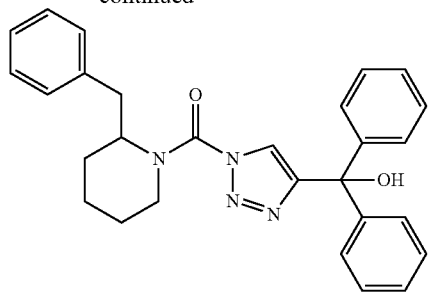

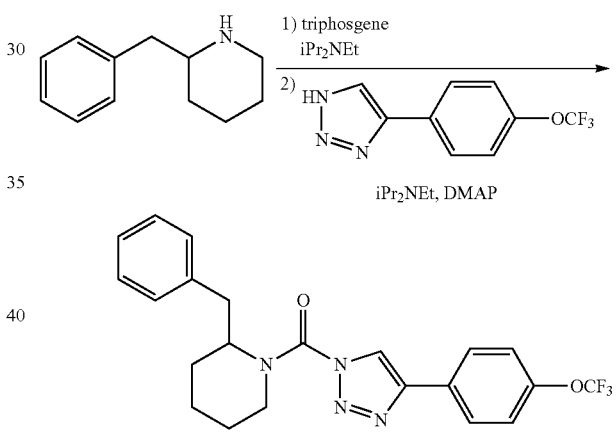

A solution of 2-benzyl piperidine (23 mg, 0.13 mmol) in THF (1 mL) was treated with iPr$_2$NEt (68 µL, 0.39 mmol) and triphosgene (20 mg, 0.067 mmol), and the reaction mixture was stirred for 30 min at 4° C. The mixture was poured into H$_2$O and extracted ethyl acetate. The organic layer was washed with H$_2$O and brine, dried over Na$_2$SO$_4$ and concentrated under reduced pressure. The intermediate was dissolved in THF (20 ml), and iPr$_2$NEt (68 µL, 0.39 mmol), DMAP (16 mg, 0.13 mmol) and 4-(4-trifluoromethoxyphenyl)-1H-1,2,3-triazole (0.40 g, 1.8 mmol) were added to the solution. The mixture was stirred for 2 h at 60° C. and poured into saturated aqueous NH$_4$Cl solution. The mixture was extracted with ethyl acetate, washed with H$_2$O and brine, dried over Na$_2$SO$_4$ and concentrated under reduced pressure. pTLC (ethyl acetate:hexane=1:4) afforded KLH25 (12 mg, 21%) as a top spot. $^1$H NMR (CDCl$_3$, 400 MHz) δ 7.72-7.54 (m, 2H), 7.45-6.89 (m, 7H), 5.29 (br, 1H), 4.34 (brd, 1H, J=13.5 Hz), 3.42-3.10 (m, 2H), 2.67 (br, 1H), 2.04-1.60 (m, 6H). $^{13}$C NMR (CDCl$_3$, 150 MHz) δ 150.07, 145.98, 138.82, 130.02, 129.57, 129.33, 128.01, 127.44, 122.28, 121.53, 121.32 (q, J=257.5 Hz, OCF$_3$), 58.29, 41.82, 37.51, 29.74, 26.17, 19.72. HRMS calculated for C$_{22}$H$_{22}$F$_3$N$_4$O$_2$ [M+H]$^+$ 431.1689. found 431.1691.

Ex. 6(L)

HT02 Alkynylated Probe

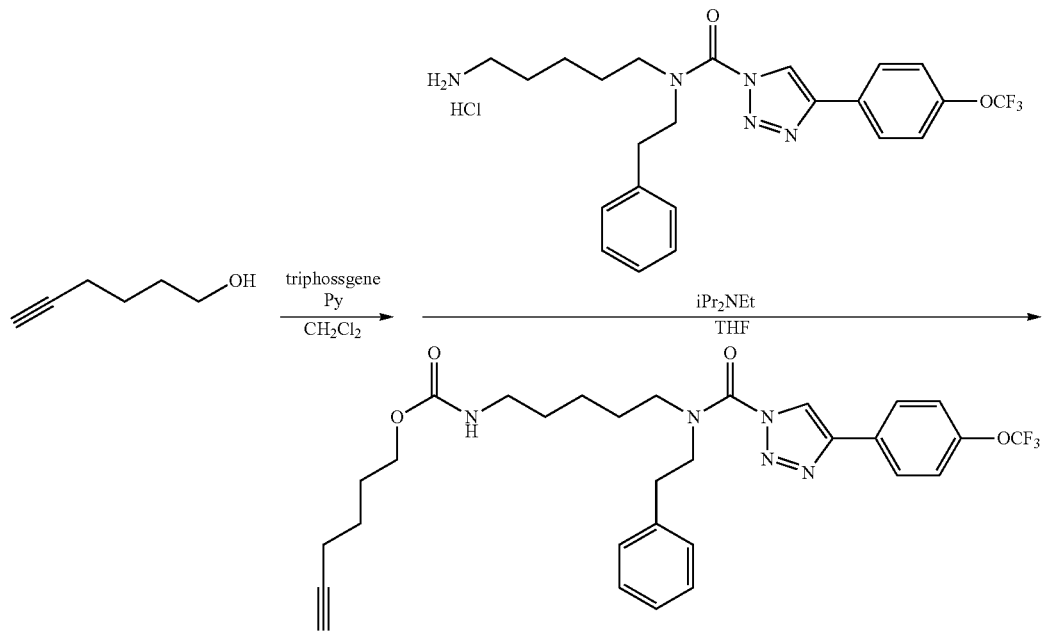

A solution of 5-hexyn-1-ol (10 mg, 0.10 mmol) in CH$_2$Cl$_2$ (2 mL) was treated with triphosgene (30 mg, 0.10 mmol) and pyridine (8 μL, 0.10 mmol), and the mixture was stirred for 30 min at 4° C. The mixture was poured into H$_2$O and extracted with ethyl acetate. The organic layer was washed with H$_2$O and brine, dried over Na$_2$SO$_4$ and concentrated under reduced pressure. The residue was dissolved in THF (1 mL), and amine HCl (14 μmol) and iPr$_2$NEt (10 μL) were added to the solution. After stirring for 1 h at room temperature, the mixture was poured into H$_2$O and extracted with ethyl acetate. The organic layer was washed with H$_2$O and brine, dried over Na$_2$SO$_4$ and concentrated under reduced pressure. pTLC (ethyl acetate:hexane=1:3) afforded HT02 (8 mg, 98%). $^1$H NMR (CDCl$_3$, 300 MHz) δ 8.42-7.80 (m, 3H), 7.40-7.10 (m, 7H), 4.70 (br, 1H), 4.15-3.50 (m, 6H), 3.25-2.95 (m, 4H), 2.22 (td, 2H, J=7.0, 2.6 Hz), 1.95 (t, 1H, J=2.6 Hz), 1.65-1.20 (m, 10H).

Ex. 6(M)

HT03 Biotinylated Probe

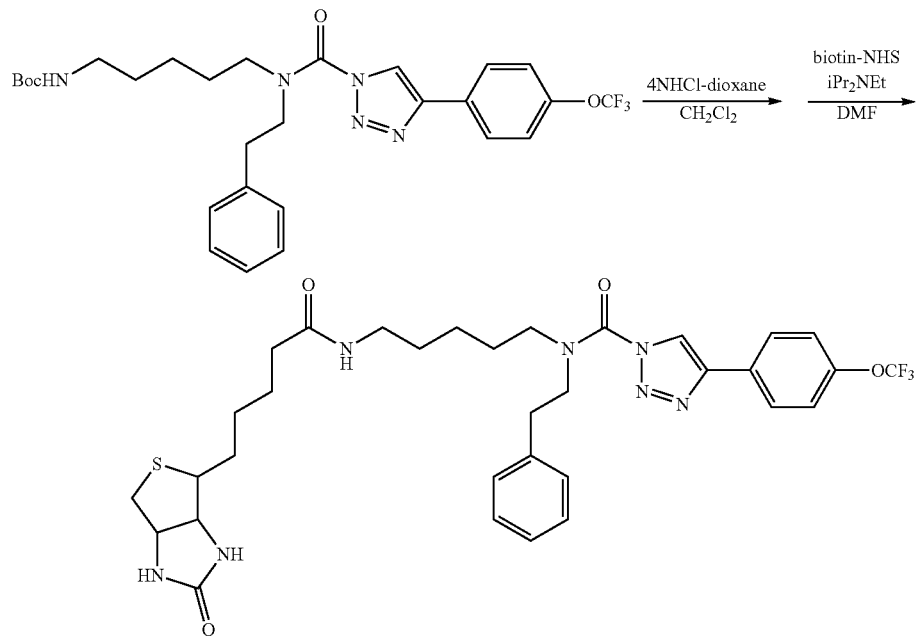

A solution of the urea (13 mg, 23 μmol) in CH$_2$Cl$_2$ (0.6 mL) was treated with 4NHCl-dioxane (0.6 mL), and the mixture was stirred for 3 h at room temperature. The solvent was evaporated and the residue was dissolved in DMF (1 mL). iPr$_2$NEt (12 μL, 69 umol) and biotin-NHS (8 mg, 23 μmol) was added to the solution, and the mixture was stirred for 2 h at room temperature. The mixture was poured into H$_2$O and extracted with ethyl acetate. The organic layer was washed with H$_2$O and brine, dried over Na$_2$SO$_4$ and concentrated under reduced pressure. Et$_2$O (1 mL) was added and the mixture was sonicated. The supernatant was removed and this procedure was repeated twice to afford HT03 (10 mg, 63%). $^1$H NMR (CDCl$_3$, 300 MHz) δ 8.43-7.80 (m, 3H), 7.35-7.05 (m, 7H), 6.25-6.03 (m, 2H), 5.30 (s, 1H), 4.48 (m, 1H), 4.29 (m, 1H), 4.00-3.50 (m, 4H), 3.30-2.80 (m, 6H), 2.70 (d, 1H, J=13.0 Hz), 2.18 (t, J=7.4 Hz), 1.80-1.20 (m, 10H).

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the disclosure have been discussed, the above specification is illustrative and not restrictive. Many variations will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

We claim:

1. A compound represented by:

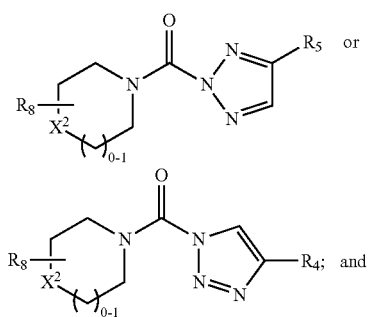

pharmaceutically acceptable salts thereof;
wherein:
X$^2$ is CH$_2$;
R$^8$ is benzyl;
R$^4$ is selected from the group consisting of H, phenyl (optionally substituted by a member of the group consisting of cyano, hydroxyl, nitro, C$_{1-6}$ alkyl (optionally substituted by one, two, or three halogens, cyano, or hydroxyl), C$_{2-6}$alkenyl (optionally substituted by one, two, or three halogens), C$_{3-6}$alkynyl (optionally substituted by one, two, or three halogens), C$_{3-6}$cycloalkyl, C$_{1-6}$alkoxy (optionally substituted by one, two, or three halogens), —COOH, —C(O)—O—C$_{1-6}$alkyl, R$^a$R$^b$N—, R$^a$R$^b$N—SO$_2$—, R$^a$R$^b$N—C(O)—, C$_{1-6}$alkyl-C(O)NR$^a$—, R$^a$—S(O)$_v$—NR$^b$— (wherein v is 0, 1 or 2), or R$^a$—S(O)$_v$— (wherein v is 0, 1 or 2), biphenyl (optionally substituted by R$^c$), phenyloxyphenyl (optionally substituted by R$^c$), naphthyl (optionally substituted by R$^c$), or C$_{1-6}$alkyl (optionally substituted by one, two, or three substituents each independently selected from hydroxyl, halo, and phenyl (optionally substituted by R$^c$));

R$^5$ is selected from the group consisting of H, phenyl (optionally substituted by R$^c$), biphenyl (optionally substituted by R$^c$), phenyloxyphenyl (optionally substituted by R$^c$), naphthyl (optionally substituted by R$^c$), or C$_{1-6}$alkyl (optionally substituted by one, two, or three substituents each independently selected from hydroxyl, cyano, halo, and phenyl (optionally substituted by R$^c$));

R$^a$ and R$^b$ may be independently selected, for each occurrence, from the group consisting of hydrogen and C$_{1-3}$alkyl; wherein C$_{1-3}$alkyl may optionally be substituted by one or more substituents selected from fluorine, cyano, oxo and hydroxyl;

or R$^a$ and R$^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

R$^c$ is selected from the group consisting of halogen, cyano, hydroxyl, nitro, C$_{1-6}$alkyl (optionally substituted by one, two, or three halogens, cyano, or hydroxyl), C$_{2-6}$alkenyl (optionally substituted by one, two, or three halogens), C$_{3-6}$alkynyl (optionally substituted by one, two, or three halogens), C$_{3-6}$cycloalkyl, C$_{1-6}$alkoxy (optionally substituted by one, two, or three halogens), —COOH, —C(O)—O—C$_{1-6}$alkyl, R$^a$R$^b$N—, R$^a$R$^b$N—SO$_2$—, R$^a$R$^b$N—C(O)—, C$_{1-6}$alkyl-C(O)NR$^a$—, R$^a$—S(O)$_v$—NR$^b$— (wherein v is 0, 1 or 2), or R$^a$—S(O)$_v$— (wherein v is 0, 1 or 2).

2. The triazole compound of claim 1, wherein R$^4$ or R$^5$ is 4-phenyloxyphenyl.

3. The triazole compound of claim 1, wherein R$^4$ is phenyl or naphthyl optionally substituted by a moiety selected from the group consisting of halo, hydroxyl, NO$_2$, C$_{1-6}$alkyl (optionally substituted by one, two, or three substituents each independently selected from hydroxyl, cyano, or halo), and C$_{1-6}$alkoxy (optionally substituted by one, two, or three halo groups, R$^5$ is phenyl optionally substituted by a moiety selected from the group consisting of hydroxyl, NO$_2$, C$_{1-6}$alkyl (optionally substituted by one, two, or three substituents each independently selected from hydroxyl, cyano, or halo), and C$_{1-6}$alkoxy (optionally substituted by one, two, or three halo groups), or R$^5$ is naphthyl optionally substituted by a moiety selected from the group consisting of halo, hydroxyl, NO$_2$, C$_{1-6}$alkyl (optionally substituted by one, two, or three substituents each independently selected from hydroxyl, cyano, or halo), and C$_{1-6}$alkoxy (optionally substituted by one, two, or three halo groups).

4. The triazole compound of claim 1, wherein the compounds are represented by:

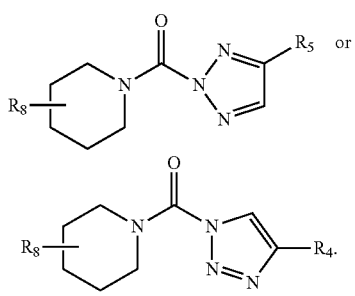

5. The triazole compound of claim 1, wherein $R^4$ is H.
6. The triazole compound of claim 1, wherein $R^5$ is H.
7. A compound represented by the following formula where w is 1, and $R^{11}$ is H:

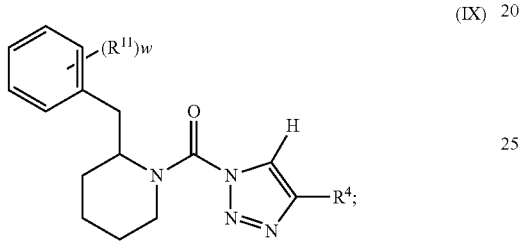

(IX)

$R^4$ is selected from the group consisting of H, halo, cyano, carboxyl, —C(O)—O—$C_{1-6}$alkyl, $R^a R^b N$—, $R^a R^b N$—$SO_2$—, $R^a R^b N$—C(O)—, $C_{1-6}$alkyl-C(O)$NR^a$—, $R^a$—S(O)$_v$—$NR^b$— (wherein v is 0, 1 or 2), $R^a$—S(O)$_v$— (wherein v is 0, 1 or 2), $C_{1-6}$alkyl (optionally substituted by one, two, or three substituents each independently selected from group consisting of halogen, hydroxyl, $C_{1-6}$alkoxy, carboxyl, cyano, and phenyl (optionally substituted by one, two or three moieties independently selected from $R^c$)), $C_{3-6}$cycloalkyl (optionally substituted by one, two or three substituents independently selected from the group consisting of halogen, cyano, hydroxyl, and $C_{1-6}$alkyl), phenyl (optionally substituted by one, two or three moieties independently selected from $R^d$), naphthyl (optionally substituted by one, two or three moieties independently selected from $R^d$), $C_{2-6}$alkenyl, and $C_{2-6}$alkynyl;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo, and hydroxyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^a R^b N$—, $R^a R^b N$—$SO_2$—, $R^a R^b N$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2); and $R^d$ is selected from the group consisting of phenyl (optionally substituted by $R^c$), phenyloxy (optionally substituted by $R^c$), halogen cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$alkynyl (optionally substituted by one, two, or three halogens), $C_{3-6}$cycloalkyl, $C_{1-6}$alkoxy (optionally substituted by one, two, or three halogens), —COOH, —C(O)—O—$C_{1-6}$alkyl, $R^a R^b N$—, $R^a R^b N$—$SO_2$—, $R^a R^b N$—C(O)—, $C_{1-6}$alkyl-C(O)$NR^a$—, $R^a$—S(O)$_v$—$NR^b$— (wherein v is 0, 1 or 2), or $R^a$—S(O)$_v$— (wherein v is 0, 1 or 2).

8. The triazole compound of claim 7 wherein $R^4$ is phenyl, optionally substituted with one, two, or three substituents each independently selected from the group consisting of: $C_{1-6}$alkyl, $C_{1-6}$hydroxyalkyl, $C_{1-6}$alkoxy, halogen, and hydroxyl.

9. A compound selected from the group consisting of compounds represented by:

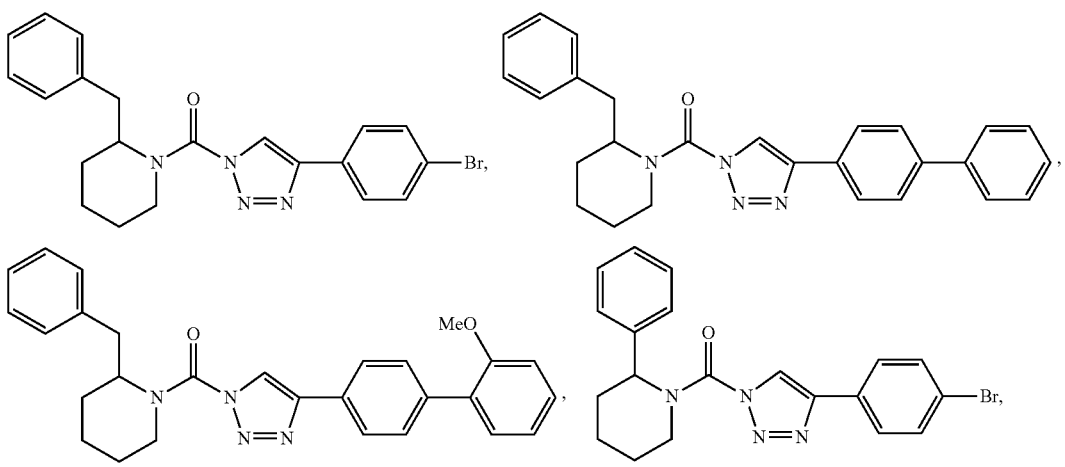

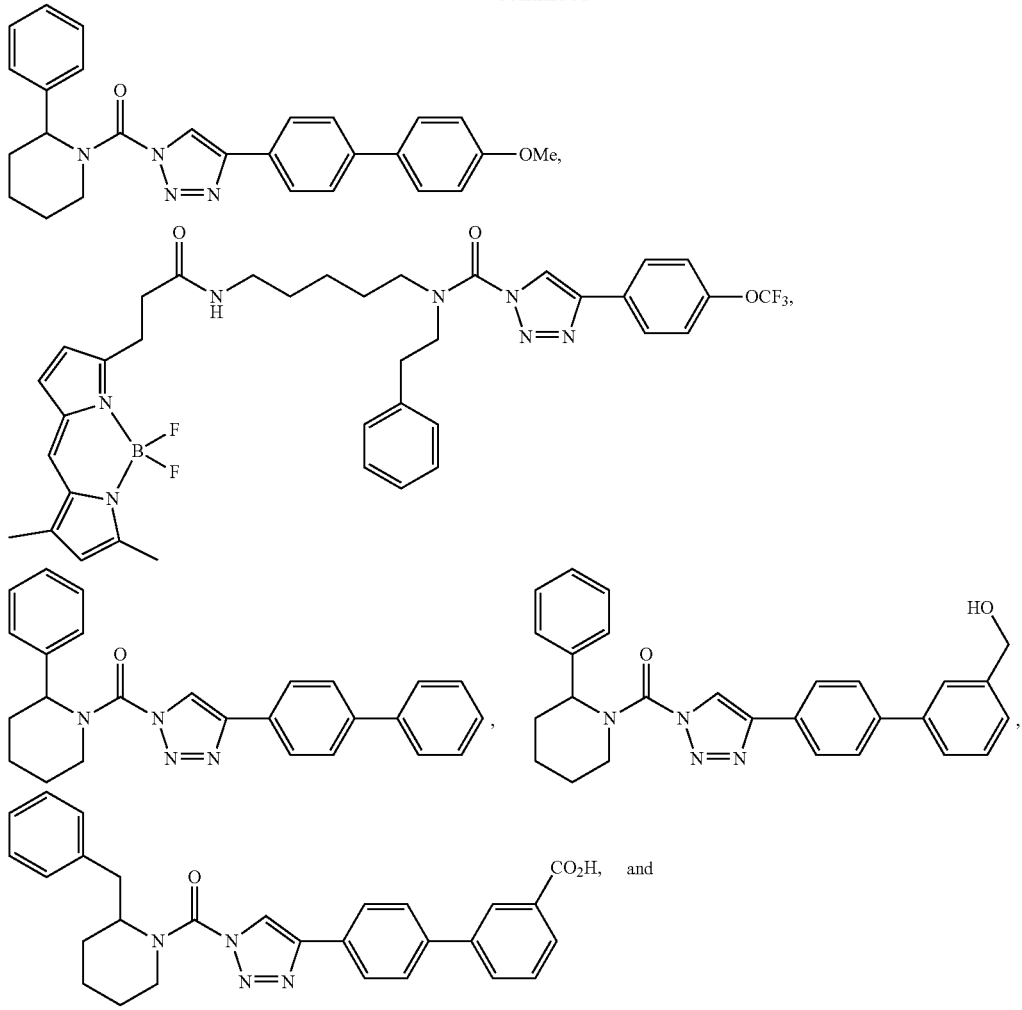
pharmaceutically acceptable salts thereof.
10. A pharmaceutical composition comprising a compound of claim 1 and a pharmaceutically acceptable carrier.
11. The compound of claim 1, wherein the compound is
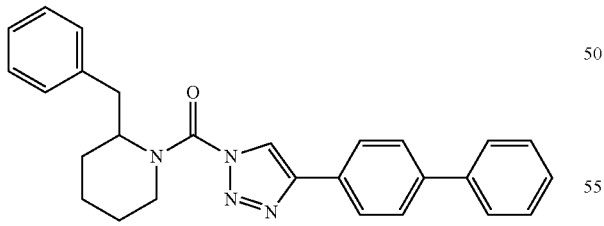
or a pharmaceutically acceptable salt thereof.
* * * * *